United States Patent
Bezwada

(10) Patent No.: US 10,689,330 B2
(45) Date of Patent: Jun. 23, 2020

(54) AMINO ACID DERIVATIVES AND ABSORBABLE POLYMERS THEREFROM

(71) Applicant: BEZWADA BIOMEDICAL, LLC, Hillsborough, NJ (US)

(72) Inventor: Rao S. Bezwada, Hillsborough, NJ (US)

(73) Assignee: Bezwada Biomedical, LLC, Hillsborough, NJ (US)

( * ) Notice: Subject to any disclaimer, the term of this patent is extended or adjusted under 35 U.S.C. 154(b) by 0 days.

(21) Appl. No.: 16/775,564

(22) Filed: Jan. 29, 2020

(65) Prior Publication Data

US 2020/0165192 A1 May 28, 2020

Related U.S. Application Data

(60) Continuation of application No. 15/850,006, filed on Dec. 21, 2017, now Pat. No. 10,550,072, which is a continuation of application No. 14/639,098, filed on Mar. 4, 2015, now abandoned, and a continuation of application No. 14/979,782, filed on Dec. 28, 2015, now Pat. No. 9,868,696, which is a continuation of application No. 14/639,098, filed on Mar. 4, 2015, now abandoned, which is a division of application No. 14/542,254, filed on Nov. 14, 2014, now Pat. No. 9,012,677, which is a continuation of application No. 13/886,611, filed on May 3, 2013, now Pat. No. 8,901,341, which is a continuation-in-part of application No. 13/358,188, filed on Jan. 25, 2012, now Pat. No. 8,461,372.

(60) Provisional application No. 61/441,983, filed on Feb. 11, 2011.

(51) Int. Cl.
| | |
|---|---|
| C07C 271/22 | (2006.01) |
| C07C 235/12 | (2006.01) |
| C08G 18/66 | (2006.01) |
| C08G 18/48 | (2006.01) |
| A61L 26/00 | (2006.01) |
| A61L 24/04 | (2006.01) |
| A61L 17/10 | (2006.01) |
| A61L 15/26 | (2006.01) |
| A61L 31/10 | (2006.01) |
| A61L 31/06 | (2006.01) |
| A61L 27/18 | (2006.01) |
| C08G 18/38 | (2006.01) |
| C08G 18/78 | (2006.01) |
| C08G 18/77 | (2006.01) |
| C07C 229/36 | (2006.01) |
| C07C 229/42 | (2006.01) |
| C07C 265/14 | (2006.01) |
| C07C 237/36 | (2006.01) |
| C07C 265/12 | (2006.01) |
| A61K 47/34 | (2017.01) |
| C07C 235/10 | (2006.01) |
| C08G 101/00 | (2006.01) |

(52) U.S. Cl.
CPC ............ *C07C 235/12* (2013.01); *A61K 47/34* (2013.01); *A61L 15/26* (2013.01); *A61L 17/10* (2013.01); *A61L 24/046* (2013.01); *A61L 26/0019* (2013.01); *A61L 27/18* (2013.01); *A61L 31/06* (2013.01); *A61L 31/10* (2013.01); *C07C 229/36* (2013.01); *C07C 229/42* (2013.01); *C07C 235/10* (2013.01); *C07C 237/36* (2013.01); *C07C 265/12* (2013.01); *C07C 265/14* (2013.01); *C08G 18/38* (2013.01); *C08G 18/48* (2013.01); *C08G 18/4837* (2013.01); *C08G 18/6607* (2013.01); *C08G 18/771* (2013.01); *C08G 18/7812* (2013.01); *A61L 2420/00* (2013.01); *C08G 2101/00* (2013.01); *Y10T 428/139* (2015.01); *Y10T 428/249921* (2015.04); *Y10T 442/10* (2015.04)

(58) Field of Classification Search
None
See application file for complete search history.

(56) References Cited

U.S. PATENT DOCUMENTS

| | | | |
|---|---|---|---|
| 4,999,417 | A | 3/1991 | Domb |
| 5,064,653 | A | 11/1991 | Sessions |
| 6,861,503 | B2 | 3/2005 | Shalaby |
| 7,772,352 | B2 | 8/2010 | Bezwada |
| 8,367,108 | B2 | 2/2013 | Bezwada |
| 8,551,519 | B2 | 10/2013 | Bezwada |
| 8,901,347 | B1 | 12/2014 | Bezwada |

(Continued)

FOREIGN PATENT DOCUMENTS

WO    2007047244 A2    4/2007

OTHER PUBLICATIONS

Ifkovits et al., Review: Photopolymerizable and Degradable Biomaterials for Tissue Engineering Applications. Tissue Engineering 2007, 13(10), 2369-85.

(Continued)

*Primary Examiner* — Marcos L Sznaidman
*Assistant Examiner* — Rayna Rodriguez
(74) *Attorney, Agent, or Firm* — Vance Intellectual Property, PC

(57) ABSTRACT

The present invention relates to the discovery of new class of hydrolysable amino acid derivatives and absorbable polyester amides, polyamides, polyepoxides, polyureas and polyurethanes prepared therefrom. The resultant absorbable polymers are useful for drug delivery, tissue engineering, tissue adhesives, adhesion prevention, bone wax formulations, medical device coatings, stents, stent coatings, highly porous foams, reticulated foams, wound care, cardiovascular applications, orthopedic devices, surface modifying agents and other implantable medical devices. In addition, these absorbable polymers should have a controlled degradation profile.

12 Claims, No Drawings

(56) References Cited

U.S. PATENT DOCUMENTS

| | | |
|---|---|---|
| 2008/0057127 A1 | 4/2008 | Bezwada |
| 2009/0069368 A1 | 3/2009 | Bono et al. |
| 2009/0098180 A1 | 4/2009 | Bezwada |
| 2009/0292029 A1 | 11/2009 | Bezwada |
| 2009/0319041 A1 | 12/2009 | Cannas et al. |
| 2014/0163253 A1 | 6/2014 | Bezwada |

OTHER PUBLICATIONS

PCT Written Opinion and International Search Report dated Nov. 30, 2012 for PCT/US2012/024641.

Bhattarai, N., et al., Nonisothermal crystallization and melting behavior of the copolymer derived from p-dioxanone and poly(ethylene glycol), European Polymer Journal 2003, 39, 1365-75.

Lutz, J-F. et. al., Synthesis and Properties of Copolymers with Tailored Sequence Distribution of Controlled/Living Radical Polymerization, Advances in Controlled/Lliving Radical Polymerization 2003, Chapter 19, 268-80.

AMINO ACID DERIVATIVES AND ABSORBABLE POLYMERS THEREFROM

This application claims a right of priority to U.S. Ser. No. 61/441,983, filed Feb. 11, 2011, and is a Continuation-in-Part of U.S. Ser. No. 13/358,188, filed Jan. 25, 2012. This priority filing is incorporated herein in its entirety. The text is found entirely in paragraph [0239], and in the text of this paragraph, and is not relied upon to support the current claims. Accordingly, this application (1) claims priority to or the benefit of an application filed before Mar. 16, 2013 and (2) does not contain a claim to a claimed invention that has an effective filing date on or after Mar. 16, 2013.

The present invention relates to the discovery of new class of hydrolysable amino acid derivatives and absorbable polyester amides, polyamides, polyepoxides, polyureas and polyurethanes prepared therefrom. The resultant absorbable polymers are useful for drug delivery, tissue engineering, tissue adhesives, adhesion prevention, bone wax formulations, medical device coatings, stents, stent coatings, foams, highly porous foams, reticulated foams, wound care, cardiovascular applications, orthopedic devices, surface modifying agents and other implantable medical devices. In addition, these absorbable polymers should have a controlled degradation profile.

Amino acids are the "building blocks" of the body. Besides building cells and repairing tissue, they form antibodies to combat invading bacteria & viruses; they are part of the enzyme & hormonal system; they build nucleoproteins (RNA & DNA); they carry oxygen throughout the body and participate in muscle activity. When a protein is broken down by digestion the result is 22 known amino acids. Eight are essential (cannot be manufactured by the body) the rest are non-essential (can be manufactured by the body with proper nutrition). Tyrosine is one of the non-essential amino acid. Tyrosine transmits nerve impulses to the brain; helps overcome depression; improves memory; increases mental alertness; and promotes the healthy functioning of the thyroid, adrenal, and pituitary glands.

U.S. Pat. No. 5,099,060 describes diphenolic monomers based on 3-(4-hydroxyphenyl) propionic acid and L-tyrosine alkyl esters (desaminotyrosyl-tyrosine alkyl esters). Subsequent related patents involve variations of this basic monomer structure. These monomers, although useful in many applications, have several limitations. The monomers are insoluble in water, and therefore the polymers made from them are not readily resorbable. In other words, the previously described polymers prepared from the previously described water-insoluble monomers will not have any weight loss while the degradation of the polymer backbone results in the loss of mechanical strength and reduction in the polymer molecular weight. The monomers also provide two phenolic hydroxyl groups, limiting the resulting polymers to be fully aromatic backbone structures, which may lead to good mechanical strength but slow degradation rate.

Poly(hydroxy acids), such as poly(glycolic acid) (PGA), poly(lactic acid) (PLA) and their copolymers are certainly the most widely investigated synthetic, degradable polymers due to their established record of safety and FDA approval. Poly(amino acids) derived from naturally occurring α-L-amino acids form another major group of degradable polymers. Despite their apparent potential as biomaterials, poly (amino acids) have actually found few practical applications. A major problem is that most of the poly(amino acids) are highly intractable (e.g., non-processible), which limits their utility.

Although several copolymers of hydroxy acids and amino acids have been prepared and evaluated from a biological perspective, their investigation as biomaterials has been rather limited. Helder et al., J. Biomed. Mater. Res., (24), 1005-1020 (1990) discloses the synthesis of glycine and DL-lactic acid copolymers and the resulting in vitro and in vivo degradation. The elegant synthesis of a copolymer derived from lactic acid and lysine was reported by Barrera et al., Macromolecules, (28), 425-432 (1995). The lysine residue was utilized to chemically attach a cell-adhesion promoting peptide to the copolymer. Other polymers of amino acids and hydroxy acids are disclosed by U.S. Pat. No. 3,773,737.

Polymers that are designed to degrade under physiological conditions are referred to as absorbable polymers. These polymers are sometimes also referred to as biodegradable, bioerodible, bioabsorbable, absorbable or hydrolyzable polymers. Synthetic absorbable polymers are generally classified into polyesters, polyorthoesters, polyanhydrides, polyesteramides, polyoxaesters.

Absorbable polymers are increasingly used in a wide range of biomedical applications including tissue engineering scaffolds, stents, stent coatings, foams, highly porous foams, reticulated foams, and adhesion prevention barriers. This increased utilization is, in part, a function of the transient nature of these polymers when used as biomedical implants or drug carriers. Medical devices made from bioabsorbable polymers can mitigate the inevitable and usually negative physiologic responses (e.g., fibrous encapsulation), which limit long-term device success. Hence, an array of absorbable polymers have been developed and studied in various biomedical applications. While significant research and development activity has been carried out on absorbable polymers, such polymers may suffer from performance deficiencies which are typically not fully recognized until new applications are identified and in-use testing has been carried out. As more uses for these materials are envisioned, an increased demand for absorbable polymers with new and improved properties targeted to address performance deficiencies may be expected to follow.

Of the synthetic absorbable polymers, polyesters find numerous applications in medical, surgical and controlled delivery applications and are the key components of a majority of absorbable medical devices, ranging from sutures, staples, orthopedic screws and implantable surgical devices to tissue engineering scaffolds.

In addition to polyesters, segmented polyurethane elastomers have also enjoyed wide use as biomaterials generally due to their excellent mechanical properties and desirable chemical versatility. While polyurethane polymers have certain useful properties, shaped articles based on these polymers are not typically absorbable and may therefore be unacceptable in circumstances that require bioabsorption. For example, certain biomedical applications, such as surgical devices including but not limited to monofilament and multifilament sutures, films, sheets, plates, clips, staples, pins, screws, stents, stent coatings, and the like, generally require the use of a material that is absorbable. Hence, the vast majority of research devoted to the development of biomedical polyurethanes has focused on long-term applications such as vascular grafts and pacemaker lead insulators.

Despite progress in the general development of polyurethanes and similar polymers for use in biomedical applications, relatively little research have been directed to developing absorbable polyurethanes for temporary, rather than longer-term implantation. See Fuller et al., U.S. Pat. No.

4,829,099; Beckmann et al., U.S. Patent Publication Nos. 2005/0013793, 2004/0170597, and 2007/0014755; Bruin et al., PCT Publication No. WO 95/26762; Woodhouse et al., U.S. Pat. No. 6,221,997; Cohn et al., U.S. Pat. No. 4,826,945, which generally discuss recent advances made in the field of absorbable polyurethanes.

Subsequent work by Bruin et al., PCT No. WO 95/26762, discloses the synthesis of crosslinked polyurethane networks incorporating lactide or glycolide and ε-caprolactone joined by a lysine-based diisocyanate. Bruin discloses that these polymers display good elastomeric properties and degrade within about 26 weeks in vitro and about 12 weeks in vivo (subcutaneous implantation in guinea pigs). Despite their disclosed desirable flexibility and degradation characteristics, these highly crosslinked polymers are not extensively used in some biomedical applications because in some cases they cannot be readily processed into surgical articles, for example, using standard techniques such as solution casting or melt processing, as is the case for the more typical linear, segmented polyurethanes.

Cohn et al., EP 295055 discloses a series of elastomeric polyester-polyether-polyurethane block copolymers intended for use as surgical articles. However, these polymers may be relatively stiff and may have low tensile strength, which may preclude their use as elastomeric biomaterials. Beckmann et al., U.S. Patent Publication No. 2005/0013793 describes polyurethane-based biodegradable adhesives from multi-isocyanate functional molecules and multifunctional precursor molecules with terminal groups selected from hydroxyl and amino groups. Woodhouse et al. discloses absorbable polyurethanes derived from amino acids. However, all these absorbable polyurethanes may suffer from one or more of the following drawbacks: (a) the very slow rate of formation of polyurethane which may be attributed to the low reactivity of the polyisocyanates, and (b) the lack of tunable physical and/or mechanical properties and/or controllable hydrolytic degradation profiles for biodegradable polyisocyanates or absorbable polyurethanes derived therefrom.

Bezwada (U.S. Patent Application Publication Nos. 20060188547, 20090292029, European Patent Publication No. EP 1937182 and WO 2007030464) discloses polyurethanes, the corresponding polyisocyanates, and preparations of their manufacture and use wherein the polyurethanes and/or polyisocyanates were reported to be absorbable.

Despite advancements in the art of producing polymeric materials and methods for making polymers suitable for use in drug delivery, tissue adhesives, adhesion prevention barrier, foams, highly porous foams, reticulated foams, bone wax formulations, stents, stent coatings, scaffolds, films, molded devices, and similar surgical articles, presently available polymers generally lack adequate performance properties desirable in surgical articles, for example, those related to bioabsorption, flex fatigue life, strength in use, flexibility and/or durability. Thus, there continues to be a need for new devices and polymers having tunable physical and/or biological properties, so that medical devices and surgical articles having a variety of end uses can be prepared. The present invention is directed, among other things, to absorbable drug delivery systems, tissue adhesives, adhesion prevention barrier, foams, highly porous foams, reticulated foams, stents, bone wax formulations, coatings including stent coatings, tissue engineering scaffolds, films, molded devices and/or flexible films with tunable physical and biological properties, and improving the processability of polyurethanes during molding and extrusion, surface properties of finished products.

SUMMARY OF THE INVENTION

Accordingly, the present invention is directed, in part, towards developing amino acid derivatives, and amine derivatives including isocyanates, amide diacids that can provide novel absorbable materials that are useful for drug delivery, tissue engineering, tissue adhesives, adhesion prevention, foams, highly porous foams, reticulated foams, stents, stent coatings, medical device coaings, bone wax formulations and other implantable medical devices.

In certain embodiments, the invention provides novel hydrolysable amines and isocyanates derived from nitrophenyl alanine and 3-nitrotyrosine that can provide polyamides, polyester amides, polyurethanes and the like which are absorbable and biocompatible. In certain embodiments, the invention provides novel and highly reactive isocyanates that can provide polyurethanes and other polymers which are absorbable and biocompatible.

In certain embodiments, the present invention provides novel amines and isocyanates derived from amino acids selected from tyrosine, 3-aminotyrosine, 3-chlorotyrosine, 3,5-dibromotyrosine, 3,5-diiodotyrosine, homotyrosine, 3-iodotyrosine, 3-nitrotyrosine, 2-tyrosine, 3-tyrosine, 4-hydroxy-3-nitrophenylalanine, 5-hydroxytryptophan, 3-nitro-4-hydroxyphenylalanine, thyronine, 3,4-dihydroxyphenylalanine, 4-hydroxyphenylglycine, 3-aminosalicylic acid; 4-aminosalicylic acid; and 5-aminosalicylic acid.

In certain embodiments, the invention provides diamine derivatives that can provide hydrophilic absorbable polyester amides that are biocompatible for absorbable sutures, staples clips, adhesion prevention barriers.

In certain embodiments, the invention provides novel polyurethanes, polyesters, polyester amides which are biodegradable and biocompatible for tissue engineering, drug delivery, tissue adhesives, adhesion prevention and other implantable medical devices.

In certain embodiments, the invention provides novel hydrolysable isocyanates for use in the formation of polyurethanes and other polymers.

In certain embodiments, the invention provides novel hydrolysable branched isocyanates with pendant long chain alkyl groups that are hydrophobic or pendant long chain PEG that are hydrophilic.

In certain embodiments, the invention provides amino acid derivatives wherein the release of drug and amino acid can be controlled.

In certain embodiments, the present invention provides NO and drug releasing amino acid derivatives wherein the rate of release of drug and nitric oxide along with the parent amino acid can be controlled.

Briefly stated, the present invention relates to the discovery of a new class of hydrolysable amines, hydrolysable isocyanates, hydrolysable amides, hydrolysable amide diacids, hydrolysable amino acid-drug, amino acid-drug-NO monomers and absorbable polyurethanes, polyureas, polyester amides and polyepoxides and blends thereof prepared therefrom. The resultant absorbable polymers are useful for drug delivery, tissue engineering, tissue adhesives, adhesion prevention, bone wax formulations, foams, highly porous foams, reticulated foams, stents, stent coatings, medical device coatings, surface modifying agents and other implantable medical devices. In addition, these absorbable polymers should have a controlled degradation profile.

In another embodiment of the present invention, absorbable polyesters, polyurethanes, polyureas and polyester amides of the present invention can be further polymerized with lactone monomers including but not limited to glycolide, lactide, caprolactone, p-dioxanone, TMC, δ-valerolactone, β-butyrolactone, morpholinedione, pivalolactone, ε-decalactone, 2,5-diketomorpholine and combinations thereof in order to control physical and biological properties.

DETAILED DESCRIPTION OF ILLUSTRATIVE EMBODIMENT

The present invention relates to the discovery of a new class of hydrolyzable isocyanates, hydrolysable amides, hydrolysable amino acid-drug and hydrolysable amino acid-drug-NO and absorbable polyester amides, polyurethanes, polyepoxides prepared therefrom. The absorbable polymers that result from polymerization of these absorbable isocyanates, amides, amide diacids are useful for, inter alia, drug delivery, tissue engineering, tissue adhesives, adhesion prevention, bone wax formulations, medical device coatings, foams, highly porous foams, reticulated foams, stents and stent coatings and other implantable medical devices. In addition, these absorbable polymers are expected to have a controllable degradation profile.

As employed above and throughout the disclosure, the terms defined below, unless otherwise indicated, shall be understood to have the defined meanings.

As used herein, the term "monomers" includes macromers, unless the context clearly indicates otherwise.

As used herein, unless otherwise defined "alkyl" refers to an optionally substituted, saturated straight, or branched hydrocarbon moiety having from about 1 to about 20 carbon atoms (and all combinations and subcombinations of ranges of carbon atoms and specific numbers of carbon atoms therein) (or, where so defined, 1 to about 36 carbons or 2 to 24 carbons), or with from about 1 to about 8 carbon atoms, herein referred to as "lower alkyl", or from about 1 to about 3 carbon atoms, such as methyl or ethyl. Alkyl groups include, but are not limited to, methyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, and 2,3-dimethylbutyl.

As used herein, the term "absorbable" refers to those classes of materials that readily hydrolyze and/or enzymatically degrade upon exposure to bodily tissue in a relatively short period of time, thus experiencing a significant weight loss in that short time period. A relatively short period of time shall be judged from the context. For example, in some contexts, the relatively short period may be two weeks to eight weeks, while in others it may be eight weeks to fifty two weeks or longer. Complete bioabsorption should take place within twelve months, or within nine months, or within six months. In this manner, the polymers derived from isocyanates of the invention may be fabricated into medical and surgical devices which are useful for a vast array of applications requiring complete or substantially complete absorption within the relatively short time periods set forth herein.

The biological properties of the absorbable polymers of the present invention used to form devices or parts thereof, as measured by its absorption rate and its breaking strength retention in vivo (BSR), can be varied to suit the needs of the particular application for which the fabricated medical device or component is intended. This can be conveniently accomplished by varying the ratio of components of the polymer chosen.

Depending on the formation route selected, these cleavable sites may be regular along the length of the chain extender, thereby giving the segmented polyurethane or polyester or the like a biodegradability which is, by some measure, predictable. Biodegradability is influenced by a number of factors, including crystallinity. The hydrophilicity of the polymer may also influence the degradability, that is, the extent to which water is accessible to the polymer matrix. The number of cleavage sites may also influence biodegradability. Generally speaking, the higher the number of sites, the greater the rate of degradation. Preferably, the cleavable site is an ester site and, more preferably, the cleavable ester site is derived from a hydroxy acid precursor. This provides segmented polyurethanes and polyesters or the like with cleavable sites that may be arranged to be recognizable by enzymes.

The polyester amides disclosed herein may be prepared by reacting amide acid of the present invention with diols in the presence of an organometallic catalyst at elevated temperatures. The organometallic catalyst is preferably a tin-based catalyst, e.g. stannous octoate and is present in the monomer mixture at a mole ratio of monomer-to-catalyst ranging from about 15,000 to about 80,000/1. The polymerization is typically carried out at a temperature ranging from about 120 to about 200 degree C., or about 160 to about 190 degree C., until the desired molecular weight and viscosity are achieved. The polyurethanes and other polymers disclosed herein may be prepared by reacting isocyanates of the present invention with branched chain extender or a chain extender and polyols of the present invention and/or generic polyols including polyethylene glycols, polyesterdiols and polyetherdiols. The polyamides disclosed herein may be prepared by reacting diamines of the present invention with diacids of the present invention and/or generic diacids including polyethylene diacids, polyesterdiacids and polyetherdiacids. The polyepoxides disclosed herein may be prepared by reacting diamines of the present invention with epoxides.

One of the beneficial properties of the polymers of the present invention is that the ester linkages are hydrolytically unstable, and therefore the polymer is absorbable because it readily breaks down into small segments when exposed to moist bodily tissue.

When any variable occurs more than one time in any constituent or in any formula, its definition in each occurrence is independent of its definition at every other occurrence. Combinations of substituents and/or variables are permissible only if such combinations result in stable compounds. Within the context of the present invention, compounds are stable if they do not degrade significantly prior to their intended use under normal conditions. In some instances, compounds of the invention may be designed or required to be bioabsorbed or biodegraded as part of their intended function. Absorbability and/or biodegradability, which may be an advantageous property of the present polymers, is not intended to mean that the polymeric compound are unstable.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form, except where such limit is clearly defined.

In one embodiment, the present invention introduces hydrolysable aromatic amines of formula A prepared by reacting functionalized amino acids i.e. amino acids functionalized with safe and biocompatible molecules (e.g., glycolic acid, lactic acid, caprolactone, and dioxanone) with aminophenol and amino benzoic acid. Bezwada US Patent Publication Numbers 2008/0057127A1, 2007/0135355A1 and 2009/0098180 A1 disclose functionalized amino acids along with their preparation and applications.

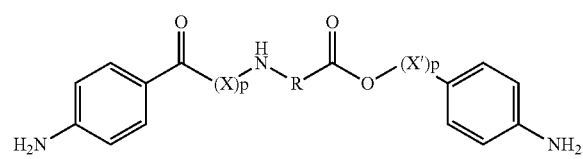

(A)

Wherein:
Each X is independently selected from:
—OCH₂CO— (glycolic ester moiety)
—OCH(CH₃)CO— (lactic ester moiety)
—OCH₂CH₂OCH₂CO— (dioxanone ester moiety)
—OCH₂CH₂CH₂CH₂CH₂CO— (caprolactone ester moiety);
—O(CH₂)$_y$CO— or, where y is one of the numbers 2, 3, 4, and 6-24 inclusive; or
—O(CH₂CH₂O)$_m$CH2CO—; where m is integer between 2-24 inclusive (together, the "X Options");
And wherein p is independently selected from 0 to 6 inclusive;
Each X' is independently selected from:
—CH₂COO— (glycolic moiety)
—CH(CH₃)COO— (lactic moiety)
—CH₂CH₂OCH₂COO— (dioxanone moiety)
—CH₂CH₂CH₂CH₂CH₂COO— (caprolactone moiety)
—(CH₂)$_y$COO— or, where y is one of the numbers 2, 3, 4, and 6-24 inclusive; or
—(CH₂CH₂O)$_m$CH2COO—; where m is integer between 2-24 inclusive (together, the "X' Options"); and,
R is a residue of an amino acid including but not limited to alanine, asparagine, aspartic acid, gamma amino butyric acid, glycine, glutamic acid, valine, lysine, isoleucine, leucine, tyrosine, ornithine, phenylalanine and sarcosine, 3-aminotyrosine, 3-chlorotyrosine, 3,5-dibromotyrosine, 3,5-diiodotyrosine, homotyrosine, 3-iodotyrosine, 3-nitrotyrosine, 2-tyrosine, 3-tyrosine, 4-hydroxy-3-nitrophenylalanine, 5-hydroxytryptophan, 3-nitro-4-hydroxyphenylalanine, thyronine, 3,4-dihydroxyphenylalanine, 4-hydroxyphenylglycine, 3-aminosalicylic acid; 4-aminosalicylic acid; and 5-aminosalicylic acid. The phrase "residue of an amino acid" refers to the chemical constituents of an amino acid except the amino and carbonyl/carboxylic acid moieties. These amino and carbonyl/carboxylic acid moieties are shown in the various structures illustrated herein appropriately adjacent to "R" or some other label for a residue of an amino acid. In certain embodiments, the amino acids are naturally occurring amino acids. In certain embodiments, the amino acids are natural constituents of mammalian protein, neurotransmitters or natural metabolic intermediate. In certain embodiments, the amino acids are natural constituents of mammalian protein.

In the structures shown in this application the aryl groups having an amino (or amino derived group) and a hydroxy (or hydroxy-derived group) or carboxy (or carboxy-derived group are typically illustrated in one orientation for simplicity (e.g., para), but these can be ortho, meta or para.

Structures of representative examples of absorbable amines of the formula (A) including but not limited to the following:

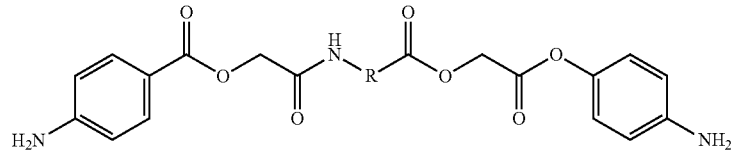

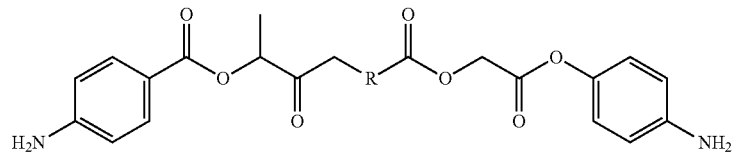

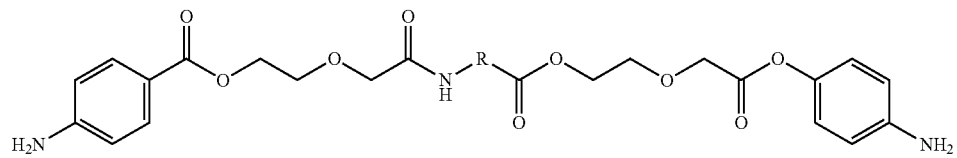

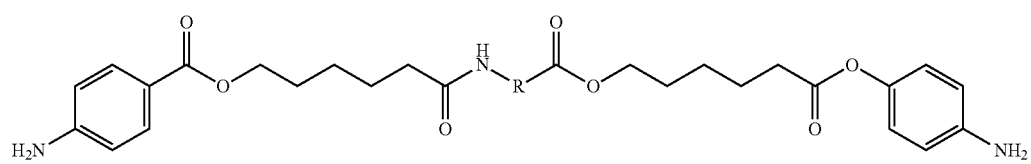

In all embodiments herein, preferably one or more occurrences of p is ≥1. In certain embodiments of these embodiments, one or more occurrences of p is ≥2.

In another embodiment, the present invention introduces hydrolysable aromatic isocyanates of formula B derived from hydrolysable amines of formula A

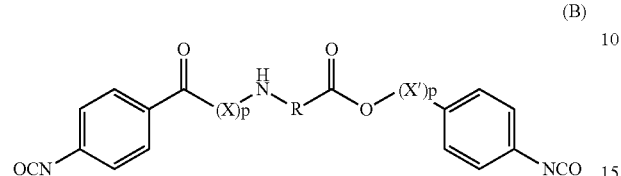

Wherein:
Each X is independently selected from the X Options;
Each X' is independently selected from the X' Options; and,
R is a residue of an amino acid.

Structures of representative examples of absorbable isocyanates of the formula (B) including but not limited to the following:

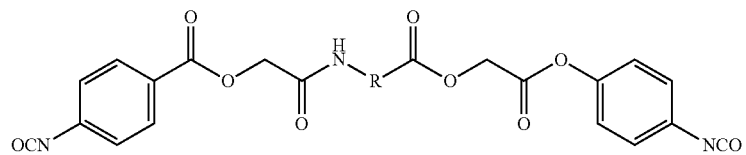

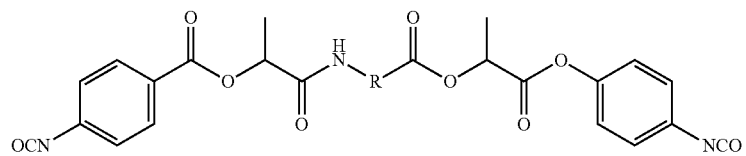

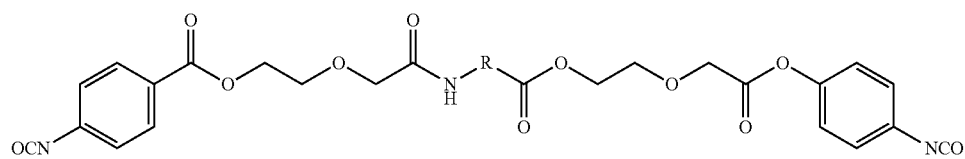

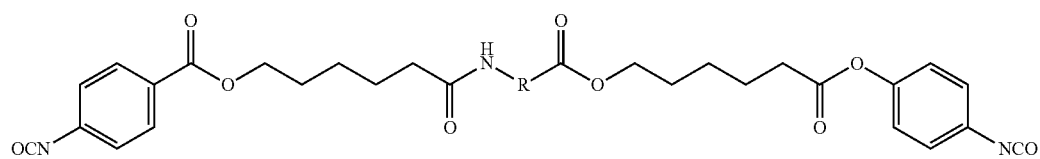

The present invention also provides biodegradable and biocompatible polyamides, polyester amides, polyureas, epoxy resins and polyurethanes derived from hydrolysable amines and isocyanates of formula A and B respectively. These polymers will have tunable mechanical and hydrolytic degradation properties and are expected to hydrolyze back to safe and biocompatible molecules including glycolic acid, lactic acid etc and parent amino acid.

In another embodiment the present invention also introduces hydrolysable aromatic amines of formula C prepared by reacting functionalized amino acids i.e. amino acids functionalized with safe and biocompatible molecules (e.g., glycolic acid, lactic acid, caprolactone, and dioxanone) with aminophenol. Bezwada US Patent Publication Number 2008/0057127A1, 2007/0135355A1 and 2009/0098180 A1 disclose these functionalized amino acids along with their preparation and applications.

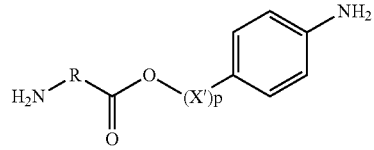

Wherein
Each X' is independently selected from the X' Options;
p is independently selected from 0 to 6 inclusive; and
R is a residue of an amino acid.

These amines of formula C upon hydrolysis will yield safe and biocompatible molecules along with the parent amino acid. Structures of representative examples of absorbable amines of the formula (C) including but not limited to the following:

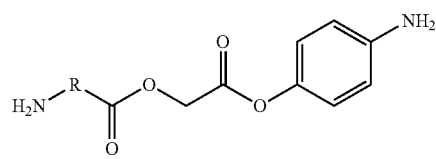

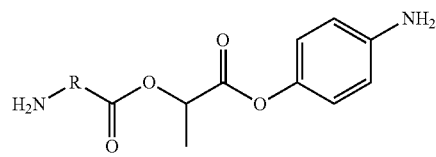

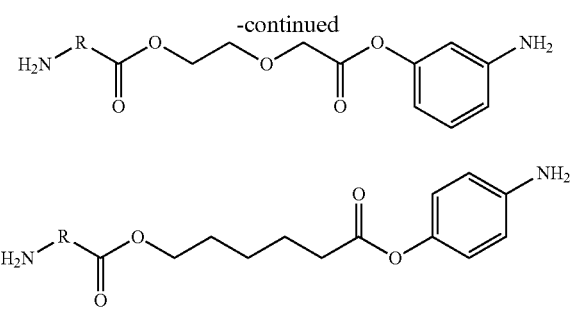

The present invention also introduces hydrolysable aromatic isocyanates of formula D

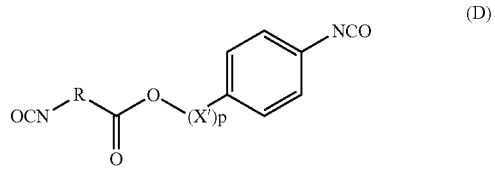

Wherein
Each X' is independently selected from the X Options;
p is independently selected from 0 to 6 inclusive; and,
R is a residue of an amino acid.

The isocyanates of formula (D) are expected to have differential rate of reactivity attributed to the presence of aliphatic and aromatic isocyanate moiety within the same molecule. Hence, these isocyanates will prove beneficial for forming prepolymers. Structures of representative examples of absorbable isocyanates of the formula (D) including but not limited to the following:

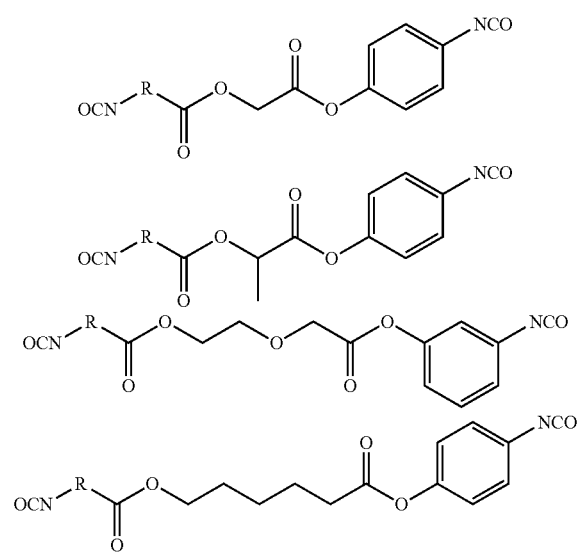

The present invention also provides absorbable polyamides, polyester amides, polyepoxides and polyurethanes derived from hydrolysable amines and isocyanates of formula C and D respectively. These polymers will have tunable mechanical and hydrolytic degradation properties and are expected to hydrolyze back to safe and biocompatible molecules including glycolic acid, lactic acid etc. and amino acid.

In another embodiment the present invention also introduces hydrolysable aliphatic amines of formula E prepared by reacting functionalized amino acids i.e. amino acids functionalized with safe and biocompatible molecules (e.g., glycolic acid, lactic acid, caprolactone, and dioxanone) with a linker molecule.

Wherein:

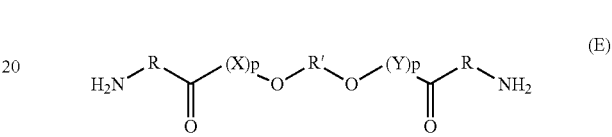

Each X is independently selected from the X Options;
And wherein p is independently selected from 0 to 6 inclusive;
Each Y is independently selected from:
—COCH$_2$O— (glycolic moiety)
—COCH(CH$_3$)O— (lactic moiety)
—COCH$_2$OCH$_2$CH$_2$O— (dioxanone moiety)
—COCH$_2$CH$_2$CH$_2$CH$_2$CH$_2$O— (caprolactone moiety)
—CO(CH$_2$)$_y$O— or, where y is one of the numbers 2, 3, 4, and 6-24 inclusive; or
—CO(CH$_2$CH$_2$O)$_m$CH$_2$O—; where m is integer between 2-24 inclusive (together, the "Y Options);
R is a residue of an amino acid; and
R' is a residue of a diol where in R' is alkyl, aryl or arylalkyl. (Such residue can be for example a residue of a PEG polyol.)

"Alkyl" with respect to R' or Rx (see below at formula W) in this and other embodiments means containing a primary (long) chain of 2 up to 24 chain atoms (not including H), where in the primary chain —CH$_2$— groups may be substituted with —O—, or —S—. Alkyl and aryl can be substituted with lower alkyl group(s) of C1 to C6. In certain embodiments, the alkyl of R' is of long chain of 2 to 6 atoms.

These amines of formula E upon hydrolysis will yield safe and biocompatible molecules including but not limited to glycolic acid, lactic acid, peg and alcohols along with the parent amino acid.

Structures of representative examples of absorbable amines of the formula (E) including but not limited to the following:

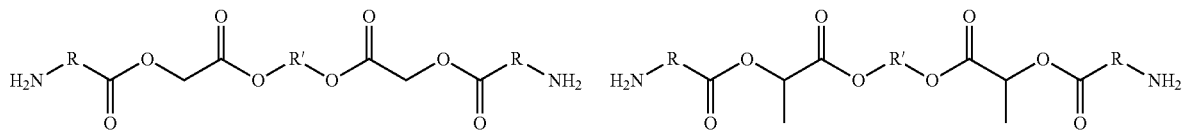

-continued

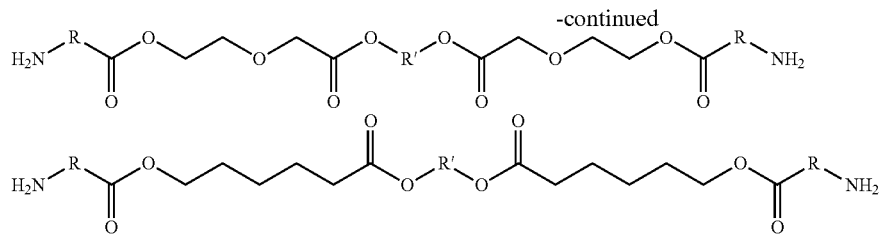

In yet another embodiment, the present invention also introduces hydrolysable isocyanates of Formula F derived from hydrolysable amines of formula E:

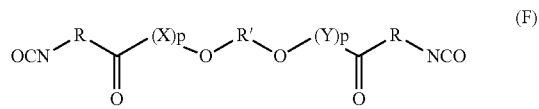

Wherein:
Each X is independently selected from the X Options;
And wherein p is independently selected from 0 to 6 inclusive;
Each Y is independently selected from the Y Options; and R is a residue of an amino acid; and
R' is a residue of a diol where in R' is alkyl, aryl or arylalkyl.

Structures of representative examples of absorbable isocyanates of the formula (F) including but not limited to the following:

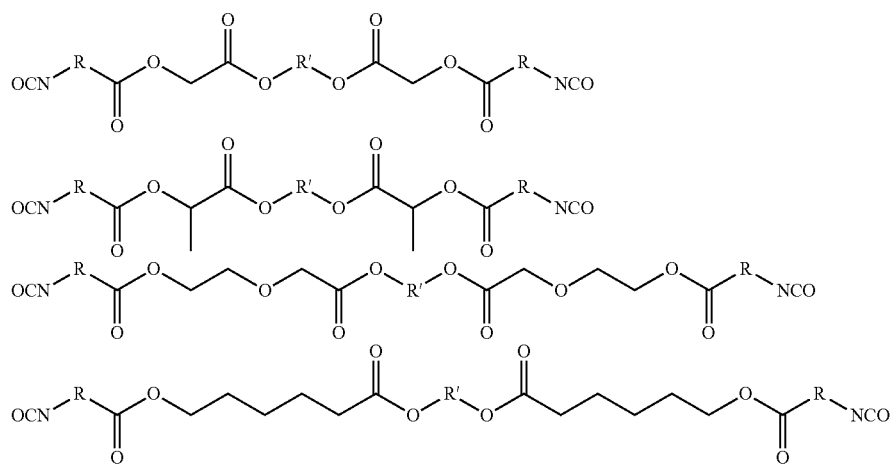

The present invention also provides absorbable polyamides, polyester amides, polyepoxides and polyurethanes derived from hydrolysable amines and isocyanates of formula E and F respectively. These polymers will have tunable mechanical and hydrolytic degradation properties and are expected to hydrolyze back to safe and biocompatible molecules including glycolic acid, lactic acid etc. and parent amino acid.

In one embodiment, the present invention introduces hydrolysable aromatic amines of formula G prepared by reacting functionalized nitrophenylalanine i.e. nitrophenylalanine functionalized with safe and biocompatible molecules (e.g. glycolic acid, lactic acid, caprolactone, and dioxanone) with amino benzoic acid. Bezwada US Patent Publication Numbers 2008/0057127A1, 2007/0135355A1 and 2009/0098180 A1 disclose these functionalized amino acids along with their preparation and applications.

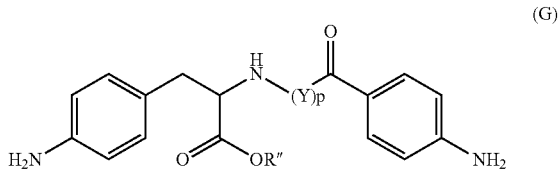

Wherein:
Each Y is independently selected from the Y Options; and, R" is alkyl, aryl or arylalkyl, or R" is a biologically active substance.

A biologically active substance in the context of the present invention is a substance that can act on a cell, virus, organ or organism, including but not limited to drugs (i.e. pharmaceuticals) or natural products, to create a change in the functioning of the cell, virus, organ or organism. In certain embodiments of the invention, the biologically active substances are organic molecules having molecular weight of about 600 or less, or to polymeric species such as proteins, nucleic acids, and the like. A biologically active substance can be a substance used in therapy of an animal, preferably a human. For use in the invention, a biologically active substance bears, or has a functional homolog that bears, one or more hydroxyl, amino or carboxylic acid substituents, including functional derivatives such as esters, amides, methyl ethers, glycosides and other derivatives that are apparent to those skilled in the art. Examples of biologically active compounds that can be used in the present invention include Capsaicin, Vitamin E, Resveratrol and isoflavonoids.

These amines of formula G upon hydrolysis will yield safe and biocompatible molecules along with the amino acid Structures of representative examples of absorbable amines of the formula (G) including but not limited to the following:

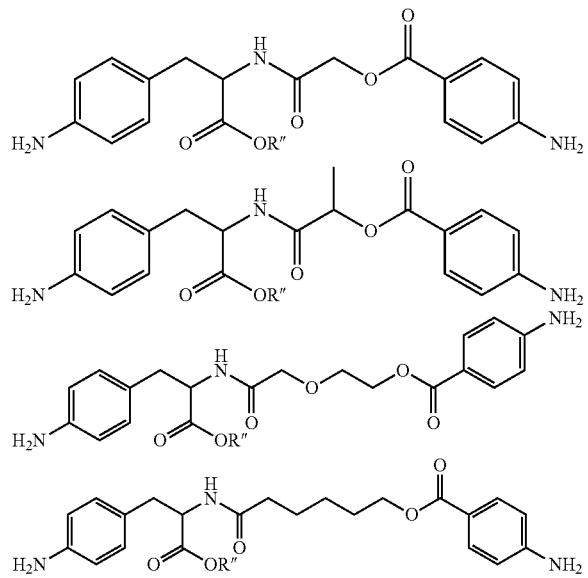

The present invention also provides hydrolysable isocyanates of general formula H derived from hydrolysable amines of formula G:

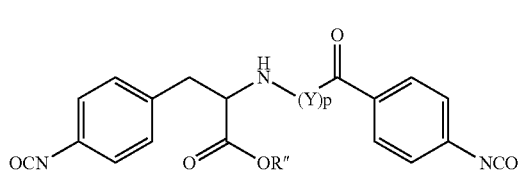

Wherein:
Each Y is independently selected from the Y Options;
And wherein p is indepently selected from 0 to 6 inclusive; and,
R" is alkyl, aryl or arylalkyl, or R" is a biologically active substance.

Structures of representative examples of absorbable isocyanates of the formula (H) includes the following

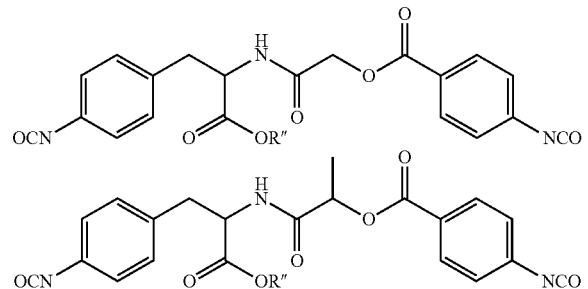

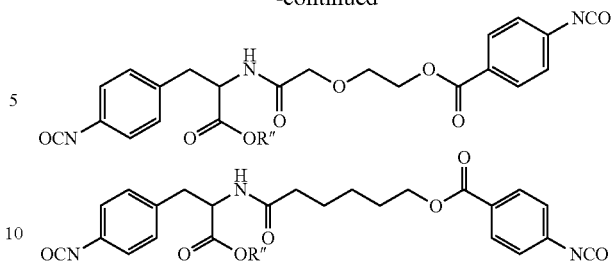

The present invention also provides absorbable polyamides, polyester amides, polyepoxides and polyurethanes derived from hydrolysable amines and isocyanates of formula G and H respectively. These polymers will have tunable mechanical and hydrolytic degradation properties and are expected to hydrolyze back to safe and biocompatible molecules including glycolic acid, lactic acid etc. and parent amino acid.

In yet another embodiment the present invention introduces multiarmed hydrolysable aromatic amines of formula I prepared by reacting functionalized nitrophenylalanine i.e. nitrophenylalanine functionalized with safe and biocompatible molecules (e.g., glycolic acid, lactic acid, caprolactone, and dioxanone) with amino benzoic acid and amino phenol.

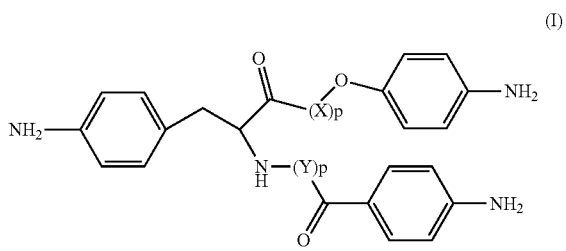

Wherein:
Each X is independently selected from the X Options;
And wherein p is independently selected from 0 to 6 inclusive; and
Each Y is independently selected from the Y Options.

Structures of representative examples of absorbable amines of the formula (I) including but not limited to the following:

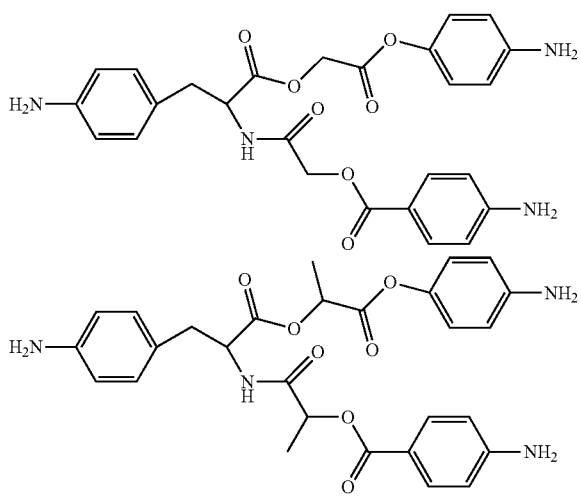

-continued

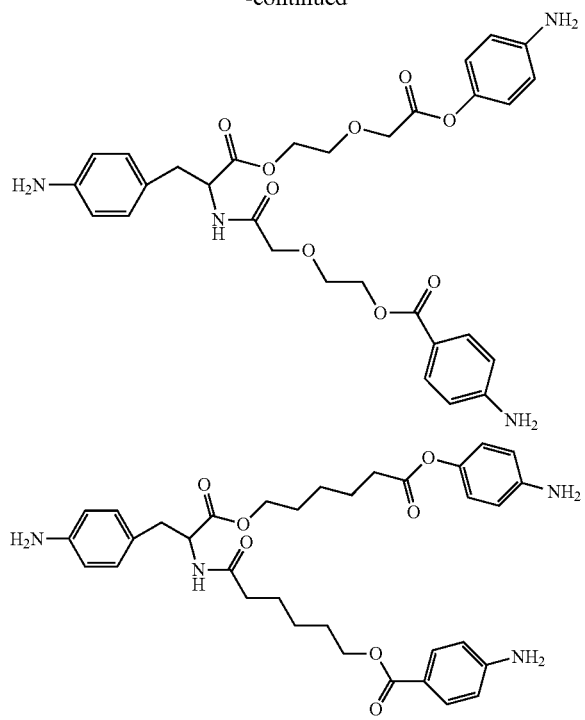

The present invention also introduces multiarmed hydrolysable aromatic isocyanates of formula J derived from hydrolysable amines of general formula I:

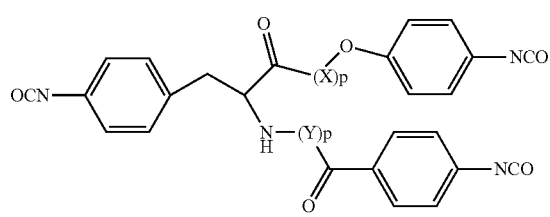

(J)

Wherein: Each X is independently selected from the X Options;

And wherein p is independently selected from 0 to 6 inclusive; and,

Each Y is independently selected from the Y Options.

Structures of representative examples of absorbable isocyanates of the formula (J) including but not limited to the following:

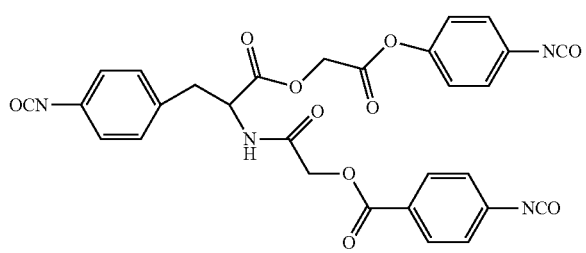

-continued

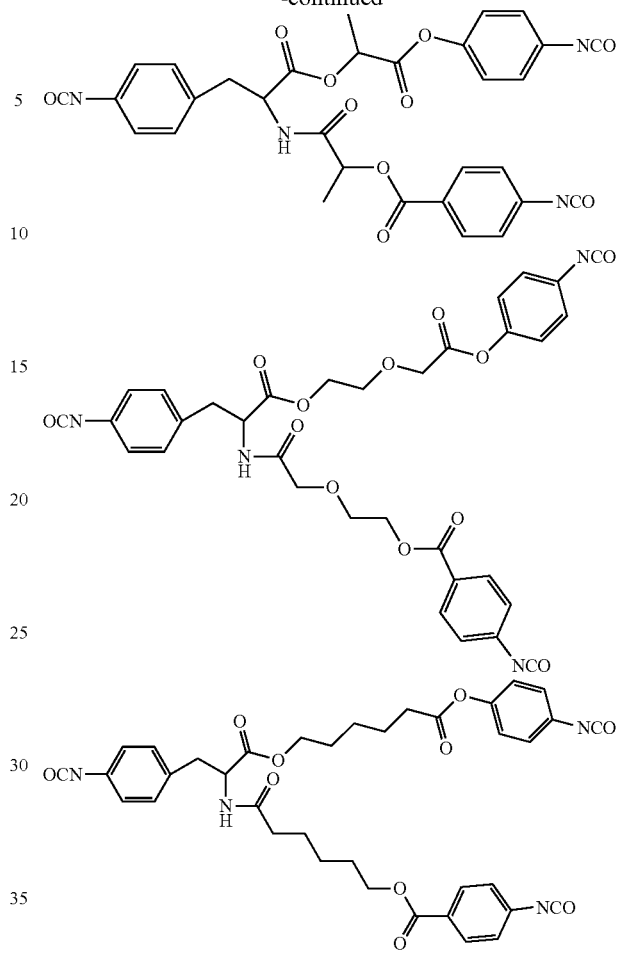

In another embodiment the present invention also introduces a drug and amino acid releasing monomers or macromers represented by general formula K prepared by reacting functionalized amino acids i.e. amino acids functionalized with safe and biocompatible molecules (e.g. glycolic acid, lactic acid, caprolactone, and dioxanone) with drug molecules. These monomers and macromers are expected to release safe and biocompatible molecules along with parent amino acids and drug molecules upon hydrolysis. These monomers and macromers are expected to be a potential candidates for site specific delivery of drugs and biologically active agents:

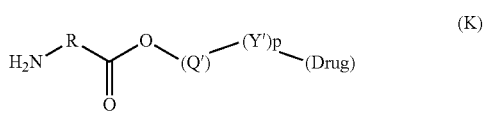

(K)

Where in
Each Y' is independently selected from the Y' Options;
—OCOCH$_2$— (glycolic moiety)
—OCOCH (CH$_3$)— (lactic moiety)
—OCOCH$_2$OCH$_2$CH$_2$— (dioxanone moiety)
—OCOCH$_2$CH$_2$CH$_2$CH$_2$— (caprolactone moiety)
—OCO(CH$_2$)$_y$— or, where y is one of the numbers 2, 3, 4, and 6-24 inclusive; or
—OCO(CH$_2$CH$_2$O)$_m$CH$_2$—; where m is integer between 2-24 inclusive; and, And wherein p is independently selected from 0 to 6 inclusive; and,
And Q' is the residue of a diol;
Drug=any biologically active substance containing one or more —OH, —COOH or —NH$_2$ functional groups by which it is covalently bound to a Y'; and
R is a residue of an amino acid.

Drug releasing amino acid monomers or macromers of formula K including but not limited to the following:

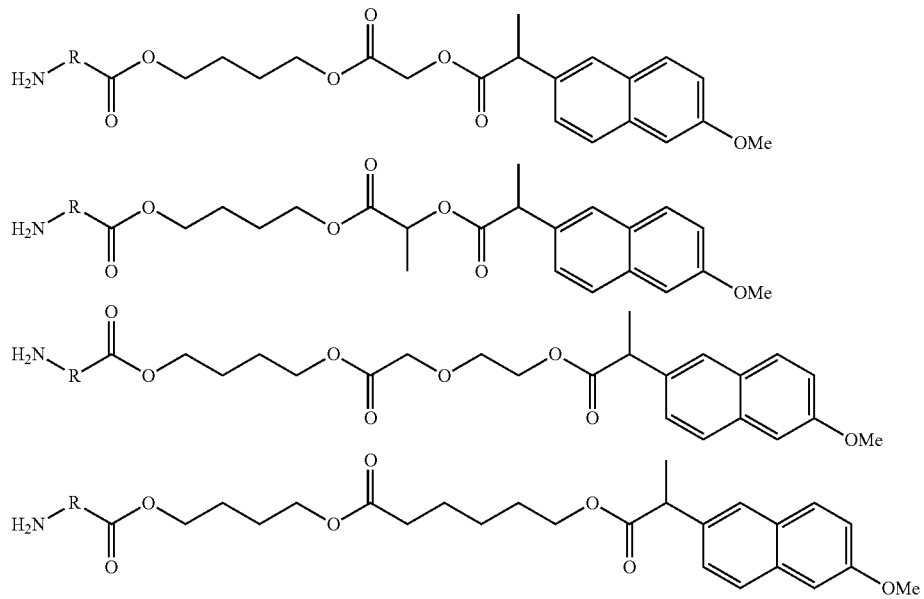

Naproxen, paracetamol, acetaminophen and acetylsalicylic acid are examples of biologically active phenolics that belong to the class of drugs called non-steroidal anti-inflammatory drugs or NSAIDs. The NSAIDs provide relief by blocking the action of prostaglandins, which are hormone-like substances that contribute to pain, inflammation, fever and muscle cramps.

Examples of biologically active carboxylic acid compounds of this invention include but not limites to Acemetacin, Aceclofenac, Acediasulfone, Adipiodone, Alminoprofen, Amlexanox, Anileridine, Baccofen, Balsalazide sodium, Bentiromide, Benzocaine, Bumetanide, Carprofen, Carzenide, Cinmetacin, Clometacin, Cromoglicic acid, Diclofenac, Diflunisal, Eprosartan, Fendosal, Flufenamic acid, Furosemide, Indometacin, Iobenzamic acid, Iocarmic acid, Iocetamic acid, Iodoxamic acid, Ioglycamic acid, Iophenoic acid, Iotroxic acid, Mefenamic acid, Naproxen, Nedocromil, Repaglinide, Salazosulfapyridine, Salicylic Acid, Salsalate, and Sarpogrelate.

The present invention also provides a drug, amino acid and nitric oxide releasing monomers and macromers represented by general formula L prepared by reacting functionalized amino acids i.e. amino acids functionalized with safe and biocompatible molecules (e.g. glycolic acid, lactic acid, caprolactone, and dioxanone) with drug molecules functionalized with nitric oxide moieties. These monomers and macromers are expected to release safe and biocompatible molecules along with parent amino acids and drug molecules along with nitric oxide upon hydrolysis. These monomers and macromers are expected to be a potential candidate for site specific delivery of drugs, nitric oxide and biologically active agents:

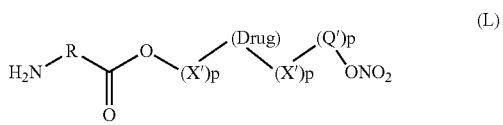

(L)

Wherein
Each X' is independently selected from the X' Options;
p is independently selected from 0 to 6 inclusive;
Q' is the residue of diol;
Drug=Any biologically active substance containing two or more —OH, —COOH or —NH$_2$ functional groups by which it is covalently bound to a X'; and
R is a residue of an amino acid.

Drug and Nitric Oxide releasing amino acid monomers of formula L including but not limited to the following:

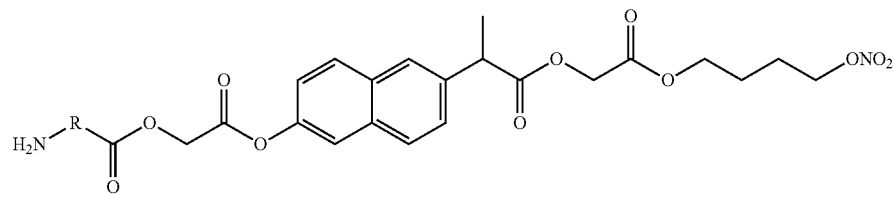

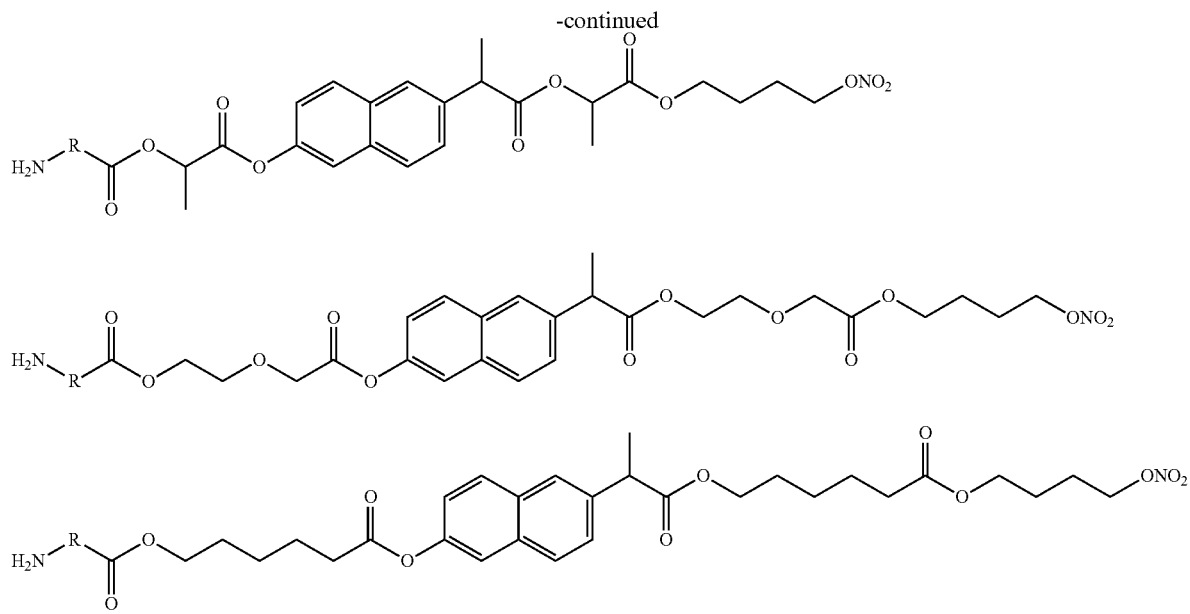

The present invention also introduces hydrolysable amide diacids of formula M derived from amino acids and symmetrical and unsymmetrical ether acids for the preparation of absorbable polyester amides:

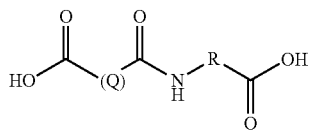

(M)

Wherein:

Q, with the adjacent carbonyl groups, is residue of symmetrical and/or unsymmetrical ether acids; and R is a residue of an amino acid.

Representative examples of absorbable amide diacids of the formula M including but not limited to the following:

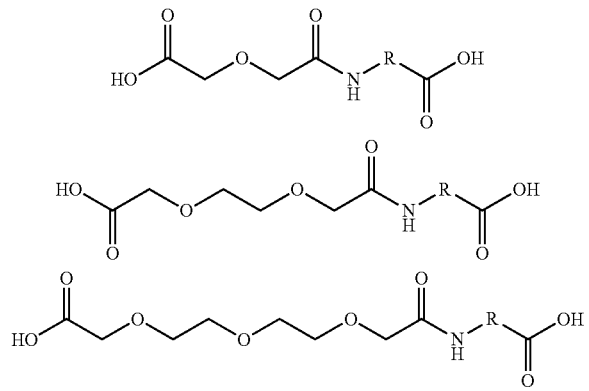

Exemplary compounds that can be the symmetrical and/or unsymmetrical ether acids include:

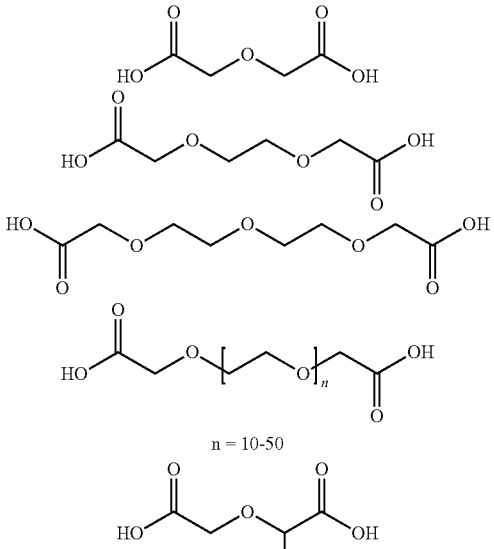

n = 10-50

Q contains a primary (long) chain of 2 up to 200 chain atoms (not including H) that are predominantly —CH$_2$—, where in the primary chain —CH$_2$— groups may be substituted with —O—, or —S—. Alkyl and aryl can be substituted with lower alkyl group(s) of C1 to C6. In certain embodiments, the alkyl of R' is of long chain of 2 to 24 atoms, or from 2 to 6 atoms.

In another embodiment the present invention also introduces aromatic isocyanates of formula N derived from nitrophenylalanine. These aromatic isocyanates can be used to prepare absorbable polyurethanes and the like containing long chain hydrophobic or hydrophilic pendant chains:

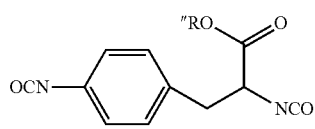
(N)

Wherein
R" is alkyl, aryl or arylalkyl, or R" is a biologically active substance.

Representative examples of diisocyanates of formula N including but not limited to the following are shown below:

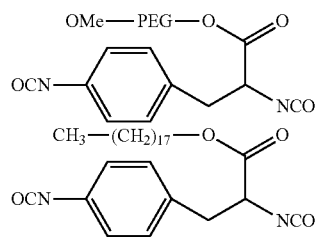

The present invention also introduces absorbable or non-absorbable and biocompatible polyurethanes and the like prepared from isocyanates of formula N.

In another embodiment the present invention also introduces aromatic isocyanates derived from 3-nitrotyrosine. These aromatic isocyanates can be used to prepare absorbable polyurethanes and the like containing long chain hydrophobic or hydrophilic pendant chains:

The present invention also introduces absorbable polyurethanes and the like prepared from isocyanates derived from 3-nitrotyrosin Absorbable amines derived from 3-Nitrotyrosine of the formula P:

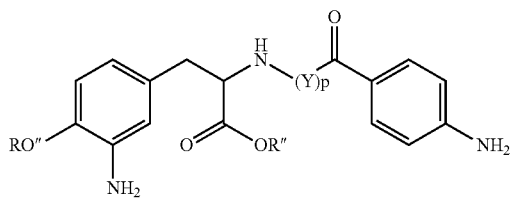
(P)

Wherein:
Each Y is independently selected from the Y Options;
And wherein p is indepently selected from 0 to 6 inclusive; and,
R" is alkyl, aryl or arylalkyl, or R" is a biologically active substance.

Structures of representative examples of absorbable amines of the formula (P) includes the following:

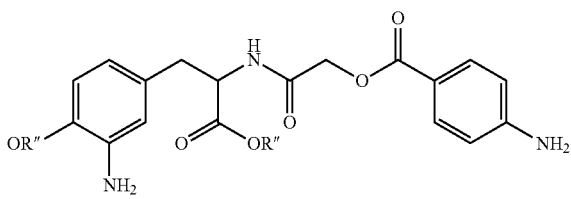

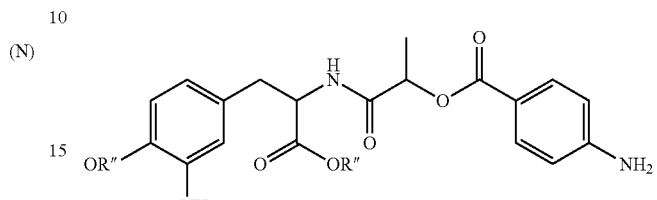

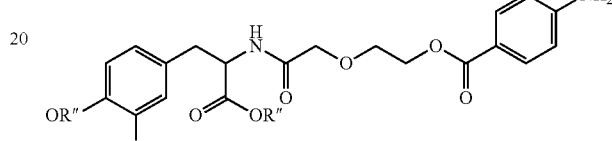

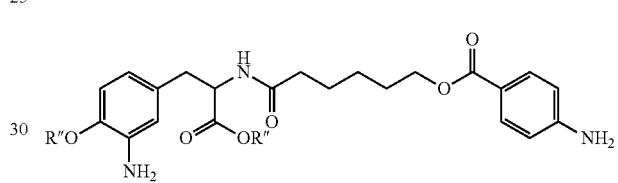

Absorbable isocyanates derived from 3-Nitrotyrosine of the formula (S)

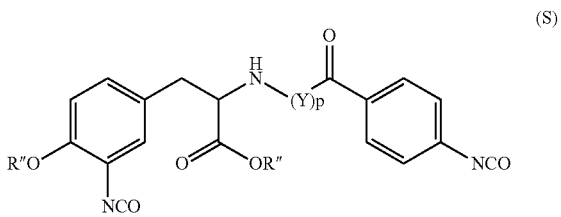
(S)

Wherein:
Each Y is independently selected from the Y Options;
And wherein p is indepently selected from 0 to 6 inclusive; and,
R" is alkyl, aryl or arylalkyl, or R" is a biologically active substance.

Structures of representative examples of absorbable isocyanates of the formula (S) includes the following

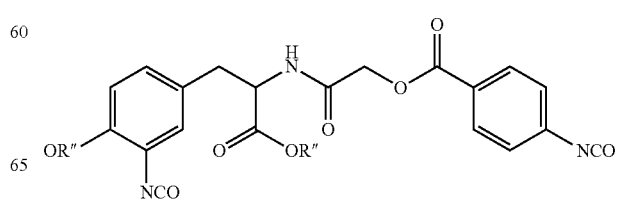

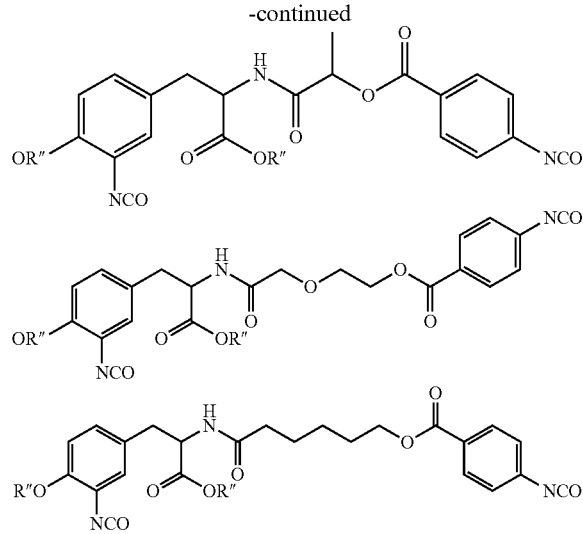

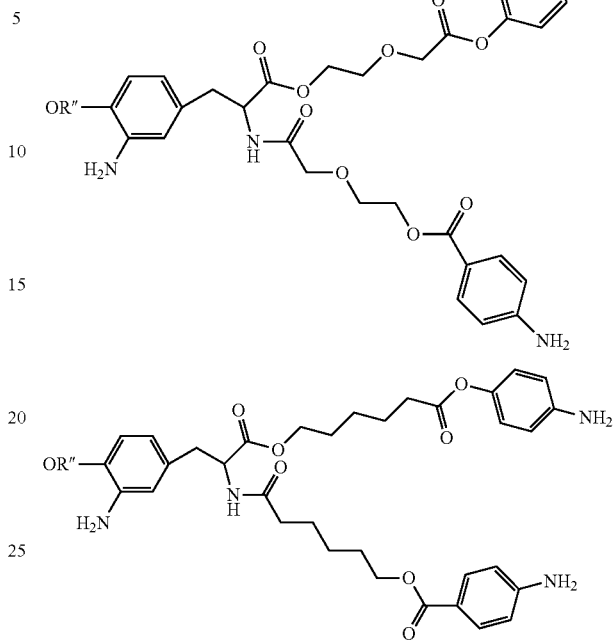

Absorbable amines derived from 3-Nitrotyrosine of the formula (T):

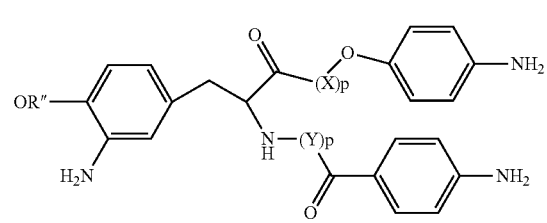

(T)

Wherein:
Each X is independently selected from the X Options;
p is indepently selected from 0 to 6 inclusive;
Y is independently selected from the Y Options; and
R" is alkyl or aryl, arylalkyl, or R" is a biologically active substance.

Structures of representative examples of absorbable amines of the formula (T) includes the following

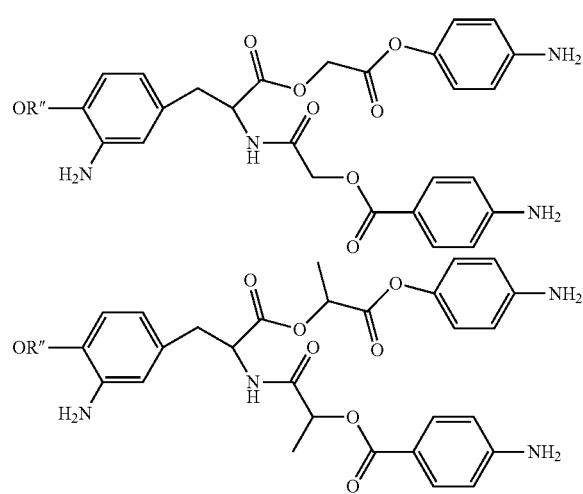

Absorbable isocyanates derived from 3-Nitrotyrosine of the formula (U):

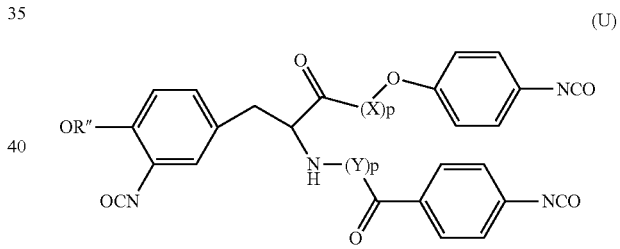

(U)

Wherein:
Each X is independently selected from the X Options;
p is indepently selected from 0 to 6 inclusive; and,
Y is independently selected from the Y Options;
R" is alkyl or aryl, arylalkyl, or R" is a biologically active substance.

Structures of representative examples of absorbable isocyanates of the formula (U) include the following

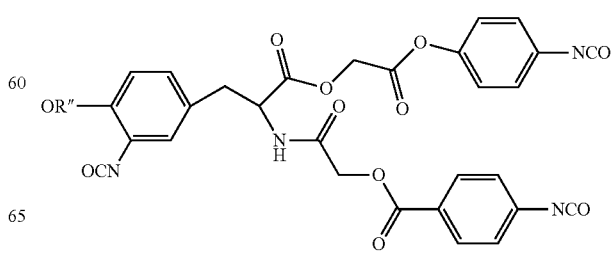

-continued

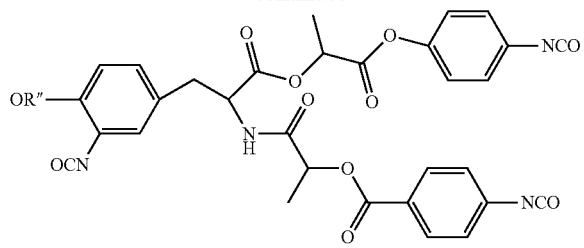

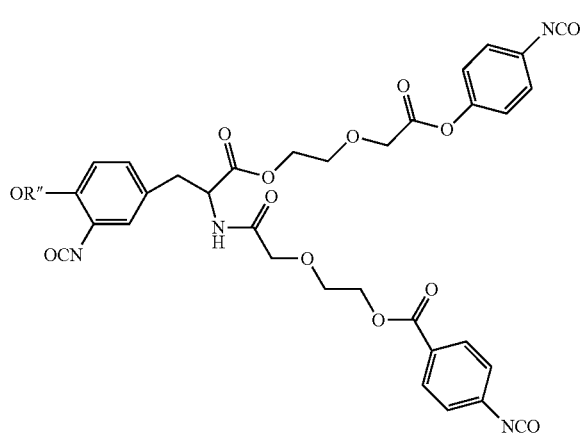

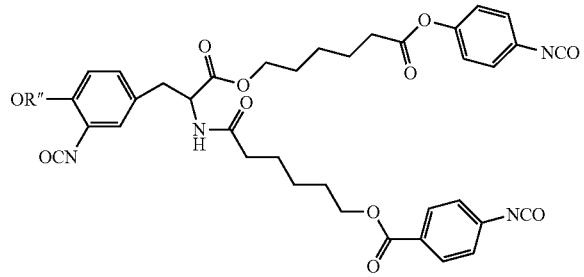

Yet another aspect of the present invention is to prepare absorbable polyurethanes and the like from at least one isocyanate derived from 3-Nitrotyrosine of the formula V:

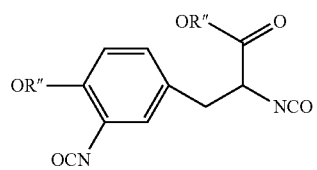

Wherein
R" is alkyl, aryl or arylalkyl, or R" is a biologically active substance.

Diisocyanate the formula (V) including but not limited to the following:

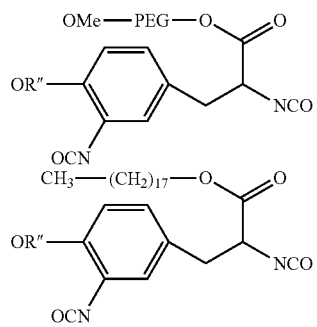

In another embodiment the present invention also introduces amide diacids of the formula W derived from diamines and symmetrical and unsymmetrical ether acid:

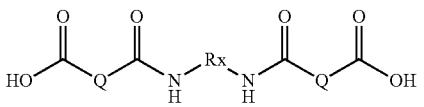

Where in Q is a residue of symmetrical and/or unsymmetrical ether acids; and
Rx is the residue of a diamine where in Rx is (a) alkyl, aryl or arylalkyl, or the residue (including the vicinal amines shown above) of a diamino amino acid or amino acid analog, such as L-lysine and aminophenyl alanine.

Amide diacids of the formula (W) including but not limited to the following:

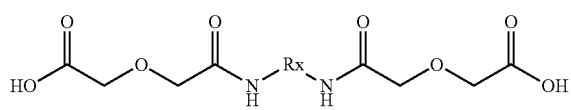

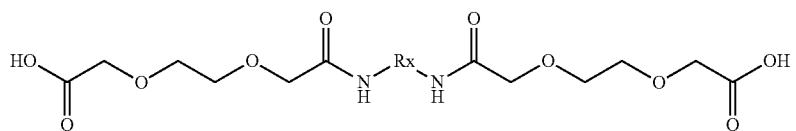

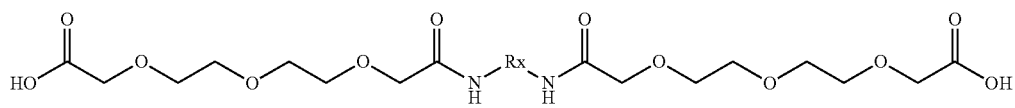

The present invention also introduces absorbable polyester amides prepared from amide diacids of formula W.

Another embodiment of the invention provides an amine or isocyanate derived from nitrophenylalanine of the formula Z or ZZ:

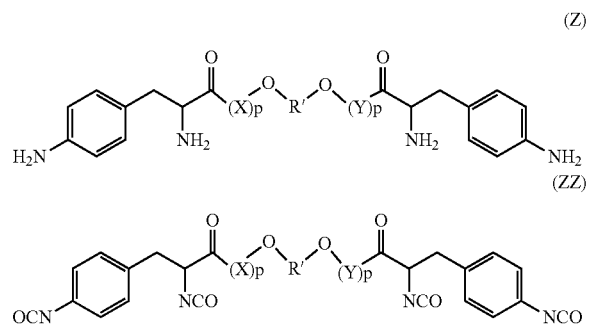

Wherein:
Each Y is independently selected from:

—COCH₂O— (glycolic moiety)
—COCH(CH₃)O— (lactic moiety)
—COCH₂OCH₂CH₂O— (dioxanone moiety)
—COCH₂CH₂CH₂CH₂CH₂O— (caprolactone moiety)
—CO(CH₂)$_y$O— or, where y is one of the numbers 2, 3, 4, and 6-24 inclusive; or
—CO(CH₂CH₂O)$_m$CH₂O—; where m is integer between 2-24 inclusive;
p is independently selected from 0 to 6 inclusive;
Each X is independently:
—OCH₂CO— (glycolic ester moiety)
—OCH(CH₃)CO— (lactic ester moiety)
—OCH₂CH₂OCH₂CO— (dioxanone ester moiety)
—OCH₂CH₂CH₂CH₂CH₂CO— (caprolactone ester moiety)
—(CH₂)$_y$COO— or, where y is one of the numbers 2, 3, 4, and 6-24 inclusive; or
—(CH₂CH₂O)$_m$CH2COO—; where m is integer between 2-24 inclusive; and
R' is a residue of a diol where in R' is alkyl, aryl or arylalkyl.

Structures of representative examples of amines of the formula (Z) include the following:

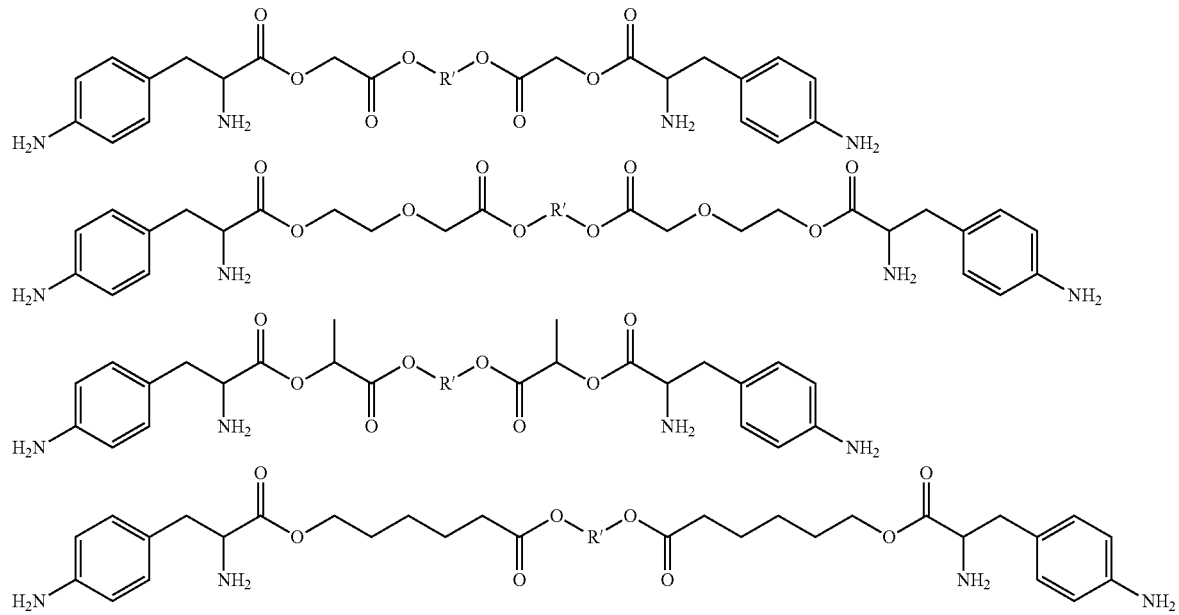

Structures of representative examples of isocyanates of the formula (ZZ) include the following

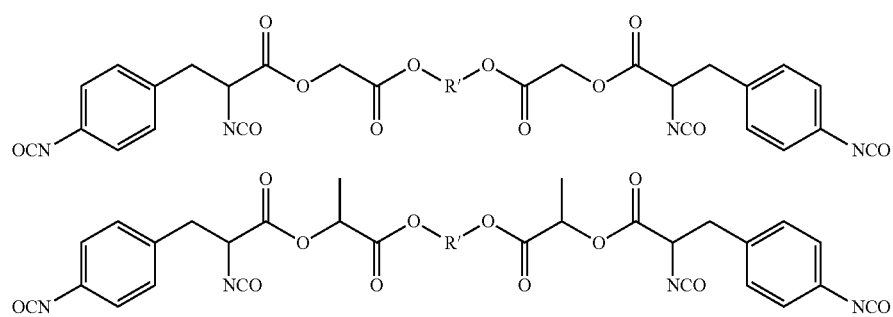

-continued

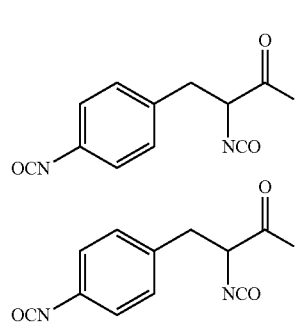 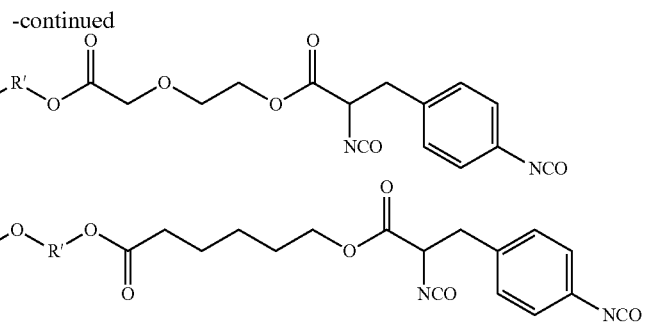

In other embodiments, absorbable polyurethanes and the like of the present invention, such as in connection with their use as stents, stent coatings, films, adhesion prevention barrier, scaffolds and polyurethane foams, highly porous foams, and reticulated foams may be derived from isocyanates described and claimed in U.S. Patent Application Publication Nos. 20060188547, 20090292029, European Patent Publication No. EP 1937182 and WO 2007030464 and reacting them with chain extenders and polyuols.

In certain embodiments, the present invention provides absorbable polyurethanes and the like derived from isocyanatres that are derived from amino acids selected from tyrosine, 3-aminotyrosine, 3-chlorotyrosine, 3,5-dibromotyrosine, 3,5-diiodotyrosine, homotyrosine, 3-iodotyrosine, 3-nitrotyrosine, 2-tyrosine, 3-tyrosine, 4-hydroxy-3-nitrophenylalanine, 5-hydroxytryptophan, 3-nitro-4-hydroxyphenylalanine, thyronine, 3,4-dihydroxyphenylalanine, 4-hydroxyphenylglycine, 3-aminosalicylic acid; 4-aminosalicylic acid; and 5-aminosalicylic acid. The amino acids used in the present invention include all of the possible stereoisomers (e.g., D, L, D/L), unless a specific isomer is identified.

In another embodiment, absorbable polyurethanes and the like of the present invention may be derived from safe and biocompatible amino acids. Polyurethanes and the like resulting from these isocyanates are expected to be safe and biocompatible. Although all the naturally occurring and synthetic amino acids can be used as precursors for preparation of hydrolysable isocyanates in the present invention, however, examples of amino acid including but not limited to alanine, asparagine, aspartic acid, gamma amino butyric acid, glycine, glutamic acid, valine, lysine, isoleucine, leucine, tyrosine, ornithine, phenylalanine and sarcosine, 3-aminotyrosine, 3-chlorotyrosine, 3,5-dibromotyrosine, 3,5-diiodotyrosine, homotyrosine, 3-iodotyrosine, 3-nitrotyrosine, 2-tyrosine, 3-tyrosine, 4-hydroxy-3-nitrophenylalanine, 5-hydroxytryptophan, 3-nitro-4-hydroxyphenylalanine, thyronine, 3,4-dihydroxyphenylalanine, 4-hydroxyphenylglycine, 3-aminosalicylic acid; 4-aminosalicylic acid; and 5-aminosalicylic acid.

In another embodiment, branched or linear absorbable polyurethanes and the like of the present invention may also be derived from isocyanates based on cycloaliphatic amino acids such as aminocyclohexanecarboxylic acid as well as cycloaliphatic amino alcohols such as aminocyclohexanol. Polyurethanes and the like from these isocyanates can be prepared according to the procedures described in U.S. Patent Application Publication Nos. 20060188547, 20090292029, European Patent Publication No. EP 1937182 and WO 2007030464. Polyurethanes and the like resulting from cycloaliphatic amino acids as well as cycloaliphatic amino alcohols will find use in a variety of applications including biomedical applications wherein controlled hydrolytic degradation is desired.

In another embodiment absorbable polyester amides can be prepared by reaction of amide diols, and/or absorbable polyols, with diacids including but not limited to oxalic acid, succinic acid, malonic acid, butanedioic acid, adipic acid, azelaic acid, sebacic acid, diglycolic acid, 3,6-dioxaoctanedioic acid, 3,6,9-trioxaundecanoic acid, functionalized oxaacids, polyethyleneglycol diacids of average molecular weight from 300 to 2000 and blends thereof.

In another embodiment absorbable polyamides will be prepared by reaction of diamines with diacids including but not limited to oxalic acid, succinic acid, malonic acid, butanedioic acid, adipic acid, azelaic acid, sebacic acid, diglycolic acid, 3,6-dioxaoctanedioic acid, 3,6,9-trioxaundecanoic acid, functionalized oxaacids, polyethyleneglycol diacids of average molecular weight from 300 to 2000 and blends thereof.

In another embodiment of the present invention, absorbable polyurethanes, polyamides, and polyesteramides of the present invention can be further polymerized with lactone monomers including but not limited to glycolide, lactide, caprolactone, p-dioxanone, TMC, δ-valerolactone, β-butyrolactone, morpholinedione, pivalolactone, ε-decalactone, 2,5-diketomorpholine and combinations thereof in order to control physical and biological properties.

The present invention introduces novel functionalized amino acids based hydrolysable monomers, macromers and absorbable polymers derived from them. The novel functionalized amino acid based monomers, macromers of the present invention are expected to have controllable hydrolysis profiles, improved bioavailability, improved efficacy, and enhanced functionality. Some of the functionalized amino acids can be monomers from which polymers can be made that are useful for medical applications. For example, functional monomers of the present invention can be polymerized to form absorbable polymers (e.g., polyesters, polyamides, polyester amides, polyurethanes, and polyanhydrides).

It can be advantageous for the monomers that are to be polymerized to have at least two active sites (e.g., 2 or 3) for polymerization. These active sites include amino, isocyanate and carboxylic acid groups. The functionalized amino acids with at least two active sites can also be copolymerized with selected difunctional molecules (e.g., dicarboxylic acids, dialcohols, diisocyanates, amino-alcohols, hydroxy-carboxylic acids, and diamines) based on the starting functionalized amino acid to form absorbable polymers. The polymers (and copolymers) of the present invention can also be further reacted/polymerized to form additional useful polymers of the present invention.

As described herein, the functionalized monomers, macromers and polymers of the present invention are useful in medical applications/medical devices. Medical application/medical devices, as used herein, encompass medical and biomedical applications and include all types of applications involved in the practice of medicine that would benefit from a material that decomposes harmlessly within a known period of time. Examples include medical and surgical devices, which include drug delivery systems (e.g., a site-specific or systemic drug delivery systems or matrices), tissue engineering (e.g., tissue scaffold), stent coatings, stents, porous devices, implantable medical devices, molded articles (e.g., vascular grafts, stents, bone plates, sutures, implantable sensors, and barriers for surgical adhesion prevention), wound closure devices (e.g., surgical clips, staples, and sutures), coatings (e.g., for endoscopic instruments, sutures, stents, and needles), fibers or filaments (which may be attached to surgical needles or fabricated into materials including sutures or ligatures, multifilament yarn, sponges, gauze, tubes, and sheets for typing up and supporting damaged surface abrasions), rods, films (e.g., adhesion prevention barriers), knitted products, foodstuffs, nutritional supplements, nutriceuticals, cosmetics, pharmaceuticals, biodegradable chewing gums, flavors, enhanced drugs, drug intermediates, cancer preventing agents, antioxidants, controlled release preparations, and solvents for drugs.

Examples of knitted products, woven or non-woven, and molded products include: burn dressings; hernia patches; medicated dressings; fascial substitutes; gauze, fabric, sheet, felt, or sponge for liver hemostasis; gauze bandages; arterial graft or substitutes; bandages for skin surfaces; suture knot clip; orthopedic pins, clamps, screws, and plates; clips (e.g., for vena cava); staples; hooks, buttons, and snaps; bone substitutes (e.g., mandible prosthesis); intrauterine devices (e.g., spermicidal devices); draining or testing tubes or capillaries; surgical instruments; vascular implants or supports; vertebral discs; extracorporeal tubing for kidney and heart-lung machines; and, artificial skin.

It would be readily apparent to one of ordinary skill in the art once armed with the teachings in the present application that the isocyanates of the present invention may be reacted with a variety of reactants that are typically employed in the preparation of bioabsorbable and biocompatible polyurethanes and/or polyester urethanes, preferably with tunable physical, mechanical properties and/or hydrolytic degradation profiles. It would also be apparent to the ordinarily skilled artisan that the terminal groups for given polyurethane, or polyester may be derivatized by further reacting the polyurethane and/or polyesters with additional derivatizing agents. Polyurethanes terminated with —NCO or hydroxyl groups can be prepared by varying the ratio of isocyanates:hydroxyl groups in the reaction mixture i.e. (isocyanates, chain extender and polyol). Polyurethanes with high molecular weights are formed when the ratio of isocyanates:hydroxyl group is 1. Furthermore, by varying the ratio of isocyanates:hydroxyl groups in the reaction mixture, polyurethanes with tunable physical and mechanical properties can be obtained. It would also be apparent to the ordinarily skilled artisan that the terminal groups for given polyurethane, or polyester may be derivatized by further reacting the polyurethane and/or polyesters with additional derivatizing agents.

In one form, the absorbable polyurethanes and polyester amides described herein are biodegradable and in certain aspects biocompatible and suitable for use in medicine. Such polyurethanes, and/or polyesters combine the good mechanical properties of polyurethanes with the degradability of polyesters.

The absorbable polyurethane and/or polyester amides herein is suitable for use in a wide variety of applications. Since the degradation products of the biocompatible polyurethanes and/or polyesters described herein are non-toxic, they are advantageously suitable for biomedical uses. For example, the properties of the polymer may be tunable, i.e., they may be made to degrade more slowly or more quickly by reducing or increasing respectively the number of ester linkages in the polymeric chain, and can thus be utilized for fabricating short-term or long-term implantable surgical materials.

The polyurethanes and/or polyester amides, polyureas, polyepoxides may be formed into articles and formulations using any known technique, such as, for example, extrusion, molding and/or solvent casting, blending. The polyurethanes and/or polyesters, polyureas, polyepoxides may be used alone, blended with other absorbable compositions, or in combination with non-bioabsorbable components. A wide variety of articles or formulations may be manufactured from the polyurethanes and/or polyesters described herein. These include but are not limited to clips and other fasteners, staples, sutures, pins, screws, prosthetic devices, wound dressings or coverings, burn dressings or coverings, drug delivery devices, anastomosis rings, stents, stent coatings, films, scaffolds, polyurethane foams, bone wax formulations and other implantable medical devices. Examples of medical implantable devices include prosthetic devices, stents, sutures, staples, clips and other fasteners, screws, pins, films, meshes, drug delivery devices or systems, anastomosis rings, surgical dressings and the like. In some embodiments, the surgical articles or components thereof include stents, stent coatings, adhesion prevention barrier, wound coverings, burn coverings, foams, tissue engineering scaffolds, films, implantable medical devices, and/or controlled drug delivery systems, more preferably stents, stent coatings, wound and/or burn coverings, bone wax formulations and/or controlled delivery systems. In certain other embodiments, the surgical articles or components thereof include sutures, ligatures, needle and suture combinations, surgical clips, surgical staples, surgical prosthetic devices, textile structures, couplings, tubes, supports, screws, or pins. In certain drug delivery systems, the systems comprise a polyurethane, and/or polyester in admixture with a biologically or pharmaceutically active agent. Non-limiting examples of polymeric carriers in such drug delivery systems and/or pharmaceutical compositions include self-supporting films, hollow tubes, beads, and/or gels. Other uses of the surgical article include their use as a scaffold for tissue engineering comprising a porous structure for the attachment and proliferation of cells, such as in vitro or in vivo. The polyurethanes and/or polyesters herein may also be used to fabricate degradable containers and packaging materials which can degrade in landfills in contrast to existing non-degradable materials which present environmental concerns.

The polymers of the present invention may be used as pharmaceutical carriers in a drug delivery matrix, i.e., a matrix for a biologically active substance (i.e., agent). The matrix may be formed by mixing the polymer with a biologically active agent. The biologically active agent can be dispersed into the polymer solution for example during preparation of matrix or via melt blending. A vast variety of different biologically active agents may be used in conjunction with the polymers of the invention. In general, therapeutic agents administered via the pharmaceutical compositions of the invention include, without limitation: anti-infectives such as antibiotics and antiviral agents; analgesics and analgesic combinations; anorexics; anti-helmintics; anti-arthritics; anti-asthmatic agents; anticonvulsants; antidepressants; anti-diuretic agents; anti-diarrheals; anti-histamines; anti-inflammatory agents; anti-migraine preparations; anti-nauseants; anti-neoplastics; anti-parkinsonism drugs; anti-pruritics; anti-psychotics; anti-pyretics, antispasmodics; anti-cholinergics; sympathomimetics; xanthine derivatives; cardiovascular preparations including calcium channel blockers and beta-blockers such as pindolol and anti-arrhythmics; anti-hypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; para-sympatyholytics; psychostimulants; sedatives; and tranquilizers; and naturally derived or genetically engineered proteins, polysaccharides, glycoproteins or lipoproteins.

The drug delivery matrix may be administered in any suitable dosage form such as oral, parenteral, subcutaneously as an implant, vaginally or as a suppository. Matrix formulations containing polymers of the invention may be formulated by mixing one or more therapeutic agents with the polymer. The biologically active agent may be present as a liquid, a finely divided solid, or any other appropriate physical form. Typically, the matrix will include one or more additives, e.g., nontoxic auxiliary substances such as diluents, carriers, excipients, stabilizers or the like. However, the presence of such additives is optional. Other suitable additives may be formulated with the polymers of this invention and pharmaceutically active agent or compound. If water is to be used as an additive, it is preferably be added immediately before administration.

The amount of biologically active agent will be dependent upon the particular agent employed and medical condition being treated. Typically, the amount of drug represents about 0.001% to about 70%, more typically about 0.01% to about 50%, and most typically about 0.1% to about 20% by weight of the matrix.

The quantity and type of polymer incorporated into a parenteral dosage form will vary depending on release profile desired and the amount of drug employed. The product may contain blends of polymers of this invention to provide the desired release profile or consistency to a given formulation.

The polymers of this invention, upon contact with body fluids including blood or the like, undergo gradual degradation (mainly through hydrolysis) with concomitant release of the dispersed drug for a sustained or extended period (as compared to the release from an isotonic saline solution). This may result in prolonged delivery (over about one to about 2,000 hours, preferably about two to about 800 hours) of effective amounts (including, for example, about 0.0001 mg/kg/hour to about 10 mg/kg/hour) of the drug. This dosage form may be administered as necessary depending on the subject being treated, the severity of the affliction, the judgment of the prescribing physician, and the like.

Individual formulations of drugs and polymers of this invention may be tested in appropriate in vitro and in vivo models to achieve the desired drug release profiles. For example, a drug may be formulated with a polymer of this invention and administered to an animal (e.g., orally). The drug release profile may be monitored by appropriate means, such as by taking blood samples at specific times and assaying the samples for drug concentration. Following this or similar procedures, those skilled in the art may formulate a variety of formulations.

The absorbable polymer material of the present invention are believed to be useful for use as a tissue engineering scaffold, i.e., as a structure for the growth or regeneration of tissue. Polyurethanes may lend themselves to such uses since the enzyme-catalyzed degradation may in some cases work concurrently with the migration or growth of cells into the material, while desirably degrading in the process into its substantially non-toxic constituents. It is also possible, in some cases, that cells migrating into or located adjacent the matrix may themselves exude proteolytic enzymes that will also mediate hydrolytic cleavage.

Such tissue engineering scaffolds may have applications in the regeneration of skin and other organs, bone, cartilage, ligaments, tendons, bladder and other tissue. The polyurethane material may also be useful in the production of sutures, which require good mechanical strength, and drug release matrices, in view of their need for non-toxic degradability. The polyurethane material may also be useful for other non-biomedical applications, where degradability into substantially non-toxic constituents is an asset. The polyurethane material lends itself to sterilization by such techniques as gamma radiation and ethylene oxide treatments.

Fibers made from the present polyurethanes and/or polyester amides can be knitted or woven with other fibers, either absorbable or non-absorbable to form meshes or fabrics.

Compositions including these polyurethanes and/or polyesters may also be used as absorbable coating for surgical devices.

In another aspect, the compositions containing the polyurethanes and/or polyester amides described herein may be used to make reinforced composites. Thus, for example, the polyurethane and/or polyester composition may form the matrix of the composite and may be reinforced with bioabsorbable or non-bioabsorbable fibers or particles. Alternatively, a matrix of any absorbable or non-bioabsorbable polymer composition may be reinforced with fibers or particulate material made from compositions containing the polyurethanes and/or polyesters described herein.

In an alternative embodiment, the branched absorbable polyurethanes, and/or polyesters described herein may be admixed with a filler. The filler may be in a particulate form, such as granulates and staple fibers. While any known filler may be used, hydroxyapatite, tricalcium phosphate, bioglass or other bioceramics are the exemplary fillers. For example, from about 10 grams to about 400 grams of filler are mixed with about 100 grams of polymer. The filled, cross-linked polymers are useful, for example, as a molding composition.

It is further contemplated that one or more medicosurgically useful substances (biologically active agents) may be incorporated into compositions containing the absorbable polyurethanes and/or polyester amides described herein. Examples of such biologically active agents include, for example, those which accelerate or beneficially modify the healing process when particles are applied to a surgical repair site. For example, articles made from compositions containing the present polyurethanes and/or polyesters may carry a therapeutic agent which will be deposited at the repair site. The biologically active agent may be chosen for its antimicrobial properties, capability for promoting repair or reconstruction and/or new tissue growth. Antimicrobial agents such as broad spectrum antibiotic, for example, gentamycin sulfate, erythromycin, or derivatized glycopeptides which are slowly released into the tissue may be applied in this manner to aid in combating clinical and sub-clinical infections in a tissue repair site. To promote repair and/or tissue growth, one or several growth promoting factors may be introduced into the articles, e.g., fibroblast growth factor, bone growth factor, epidermal growth factor, platelet derived growth factor, macrophage derived growth factor, alveolar derived growth factor, monocyte derived growth factor, magainin, and the like. Some therapeutic indications are: glycerol with tissue or kidney plasminogen activator to cause thrombosis, superoxide dismutase to scavenge tissue damaging free radicals, tumor necrosis factor for cancer therapy or colony stimulating factor and interferon, interleukin-2 or other lymphokine to enhance the immune system.

It is contemplated that it may be desirable to dye articles made from compositions containing the present branched absorbable polyurethanes and/or polyesters in order to increase visibility of the article in the surgical field. Dyes, such as those known to be suitable for incorporation in sutures, may be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979), the disclosures of which are hereby incorporated herein by reference, in their entireties. Preferably, articles in accordance with this disclosure may be dyed by adding up to about a few percent and preferably about 0.2% dye to the resin composition prior to extrusion.

Biologically active hydroxy compounds that can be used as a pendant group or covalently bonded to the amino acid of the present invention include acenocoumarol, acetarsol, actinoquinol, adrenalone, alibendol, amodiaquine, anethole, balsalazide, bamethan, benserazide, bentiromide, benzarone, benzquinamide, bevantolol, bifluranol, buclosamide, bupheniode, chlorotrianisene, chloroxylenol, cianidanol, cinepazide, cinitapride, cinepazide, cinmetacin, clebopride, clemastine, clioquinol, cyclovalone, cynarine, denopamine, dextroythyroxine, diacerein, dichlorophen, dienestrol, diethylstilbestrol, diflunisal, diiodohydroxyquinoline, dilazep, dilevalol, dimestrol, dimoxyline, diosmin, dithranol, dobutamine, donepezil, dopamine, dopexamine, doxazosin, entacapone, epanolol, epimestrol, epinephrine, estradiol valerate, estriol, estriol succinate, estrone, etamivan, etamsylate, ethaverine, ethoxzolamide, ethyl biscoumacetate, etilefrine, etiroxate, exalamide, exifone, fendosal, fenoldopam mesilate, fenoterol, fenoxedil, fenticlor, flopropione, floredil, fluorescein, folescutol, formoterol, gallopamil, gentistic acid, glaziovine, glibenclamide, glucametacin, guajacol, halquinol, hexachlorophene, hexestrol, hexobendine, hexoprenaline, hexylresorcinol, hydroxyethyl salicylate, hydroxystilbamidine isethionate, hymecromone, ifenprodil, indomethacin, ipriflavone, isoetarine, isoprenaline, isoxsuprine, itopride hydrochloride, ketobemidone, khellin, labetalol, lactylphenetidin, levodopa, levomepromazine, levorphanol, levothyroxine, mebeverine, medrylamine, mefexamide, mepacrine, mesalazine, mestranol, metaraminol, methocarbamol, methoxamine, methoxsalen, methyldopa, midodrine, mitoxantrone, morclofone, nabumetone, naproxen, nitroxoline, norfenefrine, normolaxol, octopamine, omeprazole, orciprenaline, oxilofrine, oxitriptan, oxyfedrine, oxypertine, oxyphenbutazone, oxyphenisatin acetate, oxyquinoline, papaverine, paracetanol, parethoxycaine, phenacaine, phenacetin, phenazocine, phenolphthalein, phenprocoumon, phentolamine, phloedrine, picotamide, pimobendan, prenalterol, primaquine, progabide, propanidid, protokylol, proxymetacaine, raloxifene hydrochloride, repaglinide, reproterol, rimiterol, ritodrine, salacetamide, salazosulfapyridine, salbutamol, salicylamide, salicylic acid, salmeterol, salsalate, sildenafil, silibinin, sulmetozin, tamsulosin, terazosin, terbutaline, tetroxoprim, theodrenaline, tioclomarol, tioxolone, alpha-tocopherol (vitamin E), tofisopam, tolcapone, tolterodine, tranilast, tretoquinol, triclosan, trimazosin, trimetazidine, trimethobenzamide, trimethoprim, trimetozine, trimetrexate glucuronate, troxipide, verapamil, vesnarinone, vetrabutine, viloxazine, warfarin, xamoterol.

Other biologically active phenolics that can be used include acacetin, 4-acetamido-2-methyl-1-naphthol, acetaminophen, albuterol, allenolic acid, aloe emodin, aloin, β-amino-4-hydroxy-3,5-di-iodohydrocinnamic acid, N-(5-amino-2-hydroxyphenyl)-benzeneacetamide, 4-amino-1-naphthol, 3-aminosalicylic acid, 4-aminosalicylic acid, anacardic acid, p-anol, anthragallol, anthralin, anthranol, anthrarobin, anthrarufin, apigenin, apiin, apocynin, aspidinol, aspirin, baptigenin, benzestrol, benzoresorcinol, bisphenol a, bisphenol b, butylated hydroxylanisole, butylated hydroxytoluene, capobenic acid, trans-1-(3'-carboxy-4'-hydroxyphenyl)-2-(2",5"-dihydroxyphenyl)ethane, catechin, chlorogenic acid, m-chlorophenol, 5-chloro-8-quinolinol, chloroxylenol, chlorquinaldol, chromo-nar, chrysin, cinametic acid, clorophene, coniferyl alcohol, p-coumaric acid, coumes-trol, coumetarol, daphnetin, datiscetin, deoxyepinephrine, 3,5-diiodothyronine, 3,5-di-iodotyrosine, dimethophrine, diosmetin, diresorcinol, disoprofol, dopa, dopamine, drosophilin a, efloxate, ellagic acid, embelin, Equol, eriodictyol, esculetin, esculin, ethylnorepinephrine, ethyl vanillin, eugenol, eupatorin, fenadiazole, ferulic acid, fisetin, 3-fluoro-4-hydroxyphenylacetic acid, fraxetin, fustin, galangin, gallacetophe-none, gallic acid, gardenins, genistein, gentisyl alcohol, gepefrine, geranylhydroquinone, [6]-gingerol, gossypol, guaiacol, guaifenesin, harmalol, hematoxylin, hinderin, homoeriodictyol, homogentisic acid, homovanillic acid, hydroxyamphetamine, 2-hydroxy-5-(2,5-dihydroxybenzylamino)-2-hydroxybenzoic acid, 4-hydroxy-3-methoxy-mandelic acid, n-(p-hydroxyphenyl)glycine, hydroxyprocaine, 8-hydroxyquinoline, hypericin, irigenin, isoproterenol, isoquercitrin, isothebaine, kaempferol, liothyronine, luteolin, mangostin, 5,5'-methylenedisalicylic acid, n-methylepinephrine, metyrosine, morin, mycophenolic acid, myricetin, naringenin, nylidrin, orcinol, osalmid, osthole, oxantel, paroxypropione, pentachlorophenol, 3-pentadecylcatechol, p-pentyloxy-phenol, phloretin, phloroglucinol, pinosylvine, plumbagin, pyrocatechol, pyrogallol, quercetagetin, quercetin, resacetophenone, rhamnetin, rhein, sakuranetin, salicyl alcohol, salicylanilide, 4-salicyloylmorpholine, salsalate, scopoletin, scutellarein, serotonin, (3,4,5-trihydroxyphenyl) methylenepropanedinitrile, thymol, thyropropic acid, thyroxine, tiratricol, tyrosine, vanillic acid, and vanillin.

Further biologically active carboxylic acid and/or amine compounds that can be used as a pendant group or covalently bonded to the amino acid of the present invention include Acemetacin, Aceclofenac, Acediasulfone, Adipiodone, Alminoprofen, Amisulpride, Amlexanox, Amodiaquine, Amosulalol, Amoxicillin, Amsacrine, Anileridine, Azacyclonol, Baccofen, Balsalazide sodium, Bentiromide, Benzocaine, Bromopride, Bumetanide, Carprofen, Carvedilol, Carzenide, Cefprozil, Cinitapride, Cinmetacin, Clebopride, Clenbuterol, Clometacin, Cromoglicic acid, Diclofenac, Diflunisal, Eprosartan, Ethoxzolamide, Fendosal, Flufenamic acid, Furosemide, Ibuprofen, Indometacin, Iobenzamic acid, Iocarmic acid, Iocetamic acid, Iodoxamic acid, Ioglycamic acid, Iophenoic acid, Iotroxic acid, Mefenamic acid, Nadoxolol, Naproxen, Nedocromil, D-Norpseudoephedrine, paracetamol Repaglinide, Salazosulfapyridine, Salicylic Acid, Salsalate and Sarpogrelate.

Examples of biologically active dihydroxy compounds that can be used to as a pendant group or covalently bonded to the amino acid of present invention include Adrenalone, Alfuzosin, Alibendol, Amrubicin, Apomorphine, Bamethan, Benzquinamide, Bevantolol, Bifluranol, Bisacodyl, Brodimoprim, Bunazosin, Bupheniode, Carbidopa, Carbuterol, Cyclofenil, Cyclovalone, Daunorubicin, Dichlorophen, Dienestrol, Diethylstilbestrol, Dimestrol, Dithranol, Donepezil, Doxefazepam, Doxorubicin, Entacapone, Epinepheine, Epirubicin, Esomeprazole, Etamivan, Etamsylate, Etilefrine, Ezetimibe, Fenticlor, Fluorescein, Folescutol, Formoterol, Gefitinib, Hexestrol, Hexylresorcinol, Hydroxyethyl salicylate, Ifenprodil, Isoetarine, Isoxsuprine, Itopride. HCl, Khellin, Labetalol, Mitoxantrone, Morclofone, Moxaverine, Normolaxol, Omeprazole, Oxilofrine, Oxepertine, Phenacaine, Phenolphthalein, Prazosin, Tolcapone, Vesnarinone, and Vetradutine.

Examples of biologically active diamino compounds that can be used as a pendant group or covalently bonded to the amino acid of present invention of present invention include Amisulpride, Amodiaquine, Amosul-alol, Amoxicillin, Amsacrine, Azacyclonol, Bromopride, Carvedilol, Cefprozil, Cinitapride, Clebopride, Clenbuterol, Ethoxzolamide, Nadoxolol, and D-Norpseudoephedrine.

Examples of biologically active hydroxy/amino compounds that can be used as a pendant group include Amisulpride, Amodiaquine, Amosulalol, Amoxicillin, Amsacrine, Azacyclonol, Bromopride, Carvedilol, Cefprozil, Cinitapride, Clebopride, Clenbuterol, Ethoxzolamide, Nadoxolol, D-Norpseudo-ephedrine, and paracetamol.

Examples of biologically active dicarboxylic acid compounds that can be used as a pendant group or covalently bonded to the amino acid of present invention of present invention include Adipiodone, Cromoglicic acid, Eprosartan, Iocarmic acid, Iodoxamic acid, Ioglycamic acid, Iotroxic acid, Nedocromil.

Examples of biologically active hydroxy/carboxylic acid compounds that can be used as a pendant group or covalently bonded to the amino acid of present invention include Acemetacin, Bentiromide, Cinmetacin, Clometacin, Diflunisal, Fendosal, Indometacin, Iophenoic acid, Naproxen, Repaglinide, Salazosulfapyridine, Salicylic Acid, Salsalate, and Sarpogrelate.

Examples of biologically active hydroxyl-acids for use as the pendant group or covalently bonded to the amino acid of present invention include 4-hydroxycinnamic acid, caffeic acid, chlorogenic acid, ferulic acid, sinapic acid, vanillic acid, Acemetacin, Bentiromide, Cinmetacin, Clometacin, Diflunisal, Fendosal, Indometacin, Iophenoic acid, Naproxen, Repaglinide, Salazosulfapyridine, Salicylic Acid, Salsalate, and Sarpogrelate.

Examples of useful biologically active amino/carboxylic acid compounds that can be used as a pendant group of present invention include Aceclofenac, Acediasulfone, Alminoprofen, Amlexanox, Anileridine, Baccofen, Balsalazide sodium, Benzocaine, Bumetanide, Carprofen, Carzenide, Diclofenac, Flufenamic acid, Furosemide, Iobenzamic acid, Iocetamic acid, and Mefenamic acid.

Examples of biologically active diamino compounds useful in the present invention include Amisulpride, Amodiaquine, Amosulalol, Amoxicillin, Amsacrine, Azacyclonol, Bromopride, Carvedilol, Cefprozil, Cinitapride, Clebopride, Clenbuterol, Ethoxzolamide, Nadoxolol, D-Norpseudoephedrine, amino acids (L-lysine), and natural products.

Examples of naturally occurring biologically active phenolics include bergaptol, caffeic acid, capsaicin, coumarin, daidzein, 2,5-dihydroxy-benzoic acid, ferulic acid, flavonoids, glycitein (isoflavone), 4-hydroxycinnamic acid, 4-hydroxy-coumarin, isopimpinellin, resveratrol, synapic acid, vanillic acid, vanillin, chalcones, soybean flavonoids and derivatives thereof.

Capsaicin is a biologically active phenolic that is the active component of cayenne pepper. The capsaicin is an amide of vanillylamine and $C_8$ to $C_{13}$ branched fatty acids. Topical application of capsaicin stimulates and blocks small pain fibers by depleting them of the neurotransmitter substance P that mediates pain impulses. A cream made from 0.025%-0.075% capsaicin applied 4× daily may help peripheral neuropathic pain, post-herpetic neuralgia, trigeminal neuralgia, psoriasis and fibromyalgia. It is also useful for diabetic neuropathy, cluster headaches, earache, osteo- and rheumatoid arthritis. Capsaicin is a powerful pain reliever.

Naproxen, paracetamol, acetaminophen and acetylsalicylic acid are biologically active phenolics that belong to the class of drugs called non-steroidal anti-inflammatory drugs or NSAIDs. The NSAIDs provide relief by blocking the action of prostaglandins, which are hormone-like substances that contribute to pain, inflammation, fever and muscle cramps.

Phenolic moieties, synthetic and naturally occurring, are part of many drugs.

The compounds employed in the methods of the present invention may be prepared in a number of ways well known to those skilled in the art. The compounds may be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

The surgical articles, component thereof, polymeric carrier, or the like can comprise a polymer formed by reacting an amine of one of the invention with an isocyanate, carboxylic acid, activated carboxylic acid, or epoxide, or an isocyanate of the invention with an amine, alcohol, aminoalcohol, thiol or combination thereof, or a carboxylic acid of the invention with an alcohol, amine or combination thereof.

In another embodiment, the present invention is directed to the application of novel hydrolysable isocyanates, amines, biodegradable and biocompatible polyurethanes and polyamides described in the present patent application, optionally in combination with those described in patents/patent publications U.S. Pat. No. 7,772,352, US 2010/0260702 A1, US 2009/0292029 A1, US 2009/0082540, US 2006/0288547 A1, EP 1937182 B1, EP 2298235 A1, EP 1937182 A4, EP 1937182 A2, and WO 27030464 A2, all of which have been assigned to Bezwada Biomedical, and U.S. Pat. No. 4,829,099 assigned to Fuller, et al., for use in medicinal, medical device, therapeutic, consumer product and cosmetic applications including but not limited to tissue engineering, foams (including but not limited to reticulated foams, lyophilized foams and regular foams) for wound healing and drug delivery, bone hemostats and bone fillers, tissue adhesive and sealants, adhesion prevention barriers, meshes, filters, bone void fillers, controlled drug delivery, stents, medical device coatings, pharmaceutical drug formulations, medical device, cosmetic and pharmaceutical packaging, apparels, infusion devices, blood collection tubes and devices, tubes, skin care and transdermal drug delivery. The entire disclosures of all of the above-cited patents and patent publications are incorporated by reference herein in their entirety.

In another embodiment, the present invention is directed to absorbable polyurethane foams with open and closed cell structures, including but not limited to reticulated foams, foams with vertical channels, architecturally gradient foams, trans-compositional foams and trans-structural foams and the process of preparing these absorbable foams using the novel hydrolysable isocyanates, amines, biodegradable and biocompatible polyurethanes described in the present patent application, optionally in combination with those described in patents/patent publications U.S. Pat. No. 7,772,352, US 2010/0260702 A1, US 2009/0292029 A1, US 2009/0082540, US 2006/0288547 A1, EP 1937182 B1, EP 2298235 A1, EP 1937182 A4, EP 1937182 A2, and WO 27030464 A2, all of which are assigned to Bezwada Biomedical, and U.S. Pat. No. 4,829,099, assigned to Fuller, et al., via lyophilization wherein the absorbable polyurethane polymers and/or blends thereof are dissolved in a suitable solvent such as, without limitation, dioxane, N-methylpyrrolidone, dichloromethane and/or mixtures thereof, to form a homogeneous solution which is subjected to a lyophilization process comprising a solution of a bioabsorbable elastomer in a solvent which is substantially, but not necessarily completely, solidified, then the solvent is removed from that which is lyophilized under reduced pressure to form a foam. The entire disclosures of all of the above-cited patents and patent publications are incorporated by reference herein in their entirety.

In another embodiment, isocyanates of the present invention provide a true reticulated, flexible, resilient, bioabsorbable elastomeric matrix, suitable for implantation and having sufficient porosity to encourage cellular ingrowth and proliferation in vivo. The present invention also provides a polymerization process for preparing an absorbable reticulated elastomeric matrix, the process comprising the steps of:
(1) admixing
a) a polyol component,
b) an isocyanate component,
c) a blowing agent,
d) optionally, a crosslinking agent,
e) optionally, a chain extender,
f) optionally, one or more catalysts,
g) optionally, one or more cell openers,
h) optionally, a surfactant, and
i) optionally, a viscosity modifier;
to provide a crosslinked elastomeric matrix, and reticulating the elastomeric matrix by a reticulation process to provide the reticulated elastomeric matrix.

The ingredients are present in quantities and the elastomeric matrix is prepared under conditions so as to:
(i) provide a crosslinked resiliently-compressible bioabsorbable elastomeric matrix,
(ii) control formation of biologically undesirable residues, and (iii) reticulate the foam by a reticulation process, to provide the reticulated elastomeric matrix.

In another embodiment, the invention is directed to a lyophilization process for preparing a reticulated elastomeric matrix comprising lyophilizing a flowable polymeric material. In another embodiment, the polymeric material comprises a solution of a solvent-soluble bioabsorbable elastomer in a solvent. In another embodiment, the flowable polymeric material is subjected to a lyophilization process comprising solidifying the flowable polymeric material to form a solid, e.g., by cooling a solution, then removing the non-polymeric material, e.g., by evaporating the solvent from the solid under reduced pressure, to provide an at least partially reticulated elastomeric matrix. In another embodiment, a solution of a bioabsorbable elastomer in a solvent is substantially, but not necessarily completely, solidified, then the solvent is evaporated from that material to provide an at least partially reticulated elastomeric matrix. In another embodiment, the temperature to which the solution is cooled is below the freezing temperature of the solution. In another embodiment, the temperature to which the solution is cooled is above the apparent glass transition temperature of the solid and below the freezing temperature of the solution.

In another embodiment, the invention is directed to a lyophilization process for producing an elastomeric matrix having a reticulated structure, the process comprising the steps of:
a) forming a solution comprising a solvent-soluble bioabsorbable elastomer in a solvent;
b) at least partially solidifying the solution to form a solid, optionally by cooling the solution; and
c) removing the non-polymeric material, optionally by evaporating the solvent from the solid under reduced pressure, to provide an at least partially reticulated elastomeric matrix comprising the elastomer.

In another aspect of the present invention, the polymers of the present invention may contain a cleavable site which is preferably an ester site and, more preferably, the cleavable ester site is adjacent one or more amino acids. This provides segmented polyurethanes with cleavable sites in its chain extender, which sites may be arranged to be recognizable by enzymes.

In another embodiment of the present invention, the inventive polymers can be used as a pharmaceutical carrier in a drug delivery matrix. The matrix is formed by mixing the polymer with a therapeutic agent. A vast variety of different therapeutic agents can be used in conjunction with the polymers of the invention. In general, therapeutic agents administered via the pharmaceutical compositions of the invention include, without limitation antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihist-amines; antiinflammatory agents; antimigraine preparations; antinauseants; antineo-plastics; antiparkinsonism drugs; antipruritics; antipsychotics; antipyretics, antispas-modics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; para-sympatholytics; psychostimulants; sedatives; tranquilizers; and naturally derived or genetically engineered proteins, polysaccharides, glycoproteins or lipoproteins.

The drug delivery matrix may be administered in any suitable dosage form such as oral, parenteral, subcutaneously as an implant, vaginally or as a suppository. Matrix formulations containing polymers of the invention is formulated by mixing one or more therapeutic agents with the polymer. The therapeutic agent may be present as a liquid, a finely divided solid, or any other appropriate physical form. Typically, the matrix will include one or more additives, e.g., nontoxic auxiliary substances such as diluents, carriers, excipients, stabilizers or the like. However, the presence of such additives is entirely optional. Other suitable additives may be formulated with the polymers of this invention and pharmaceutically active agents or compounds, however, if water is to be used it should be added immediately before administration.

The amount of therapeutic agent will be dependent upon the particular drug employed and medical condition being treated. Typically, the amount of drug represents about 0.001% to about 70%, more typically about 0.01% to about 50%, and most typically about 0.1% to about 20% by weight of the matrix.

The quantity and type of polymer incorporated into a parenteral dosage form will vary depending on the release profile desired and the amount of drug employed. The product may contain blends of polymers of this invention to provide the desired release profile or consistency to a given formulation.

The polymers of this invention, upon contact with body fluids including blood or the like, undergoes gradual degradation (mainly through hydrolysis) with concomitant release of the dispersed drug for a sustained or extended period (as compared to the release from an isotonic saline solution). This can result in prolonged delivery (e.g., over one to 2,000 hours, preferably two to 800 hours) of effective amounts (e.g., 0.0001 mg/kg/hour to 10 mg/kg/hour) of the drug. This dosage form can be administered as necessary depending on the subject being treated, the severity of the affliction, the judgment of the prescribing physician, and the like.

Individual formulations of drugs and polymers of this invention may be tested in appropriate in vitro and/or in vivo models to achieve the desired drug release profiles. For example, a drug could be formulated with a polymer of this invention and orally administered to an animal. The drug release profile is monitored by appropriate means, such as by taking blood samples at specific times and assaying the samples for drug concentration. Following this or similar procedures, those skilled in the art are able to formulate a variety of formulations having the desired release profile.

The polyurethanes, polyureas, polyamideurethanes, and/or polyureaurethanes of the invention may be formed into various articles for surgical and medical uses including, without limitation:
a. burn dressings, b. hernia patches, c. medicated dressings, d. fascial substitutes, e. gauze, fabric, sheet, felt or sponge for liver hemostasis, f. gauze bandages, g. arterial graft or substitutes, h. bandages for skin surfaces, i. suture knot clip, j. orthopedic pins, clamps, screws, and plates, k. clips (e.g., for vena cava), l. staples, m. hooks, buttons, and snaps, n. bone substitutes (e.g., mandible prosthesis), o. intrauterine devices (e.g., spermicidal devices), p. draining or testing tubes or capillaries, q. surgical instruments, r. vascular implants or supports, s. vertebral discs, t. extracorporeal tubing for kidney and heart-lung machines, and the like.

The polyurethanes, polyureas, polyamideurethanes, and/or polyureaurethanes of the invention may be formed into surgical articles using any known technique, such as, for example, extrusion, molding and/or solvent casting. The polyurethanes, polyureas, polyamideurethanes, and/or polyureaurethanes may be used alone, blended with other bioabsorbable compositions, or in combination with non-bioabsorbable components. A wide variety of surgical articles may be manufactured from the polyurethanes, polyureas, polyamideurethanes, and/or polyureaurethanes described herein. These include but are not limited to clips and other fasteners, staples, sutures, pins, screws, prosthetic devices, wound dressings or coverings, burn dressings or coverings, drug delivery devices, anastomosis rings, stents, stent coatings, films, scaffolds, polyurethane foams, reticulated foams and other implantable medical devices. Examples of medical implantable devices include prosthetic devices, stents, sutures, staples, clips and other fasteners, screws, pins, films, meshes, drug delivery devices or systems, anastomosis rings, surgical dressings and the like. In some preferred embodiments, the surgical articles or components thereof include stents, stent coatings, wound coverings, burn coverings, foams, tissue engineering scaffolds, films, implantable medical devices, and/or controlled drug delivery systems, more preferably stents, stent coatings, wound and/or burn coverings, and/or controlled delivery systems. In certain other preferred embodiments, the surgical articles or components thereof include sutures, ligatures, needle and suture combinations, surgical clips, surgical staples, surgical prosthetic devices, textile structures, couplings, tubes, supports, screws, or pins. In certain preferred drug delivery systems, the systems comprise a polyurethane, polyurea, polyamideurethane, and/or polyureaurethane in admixture with a biologically or pharmaceutically active agent. Non-limiting examples of polymeric carriers in such drug delivery systems and/or pharmaceutical compositions include self-supporting films, hollow tubes, beads, and/or gels. Other preferred uses of the surgical articles include their use as scaffolds for tissue engineering comprising a porous structure for the attachment and proliferation of cells.

Preferably, the surgical and medical uses of the filaments, films, and molded articles of the present invention include, but are not necessarily limited to knitted products, woven or non-woven, and molded products including, burn dressings, hernia patches, medicated dressings, facial substitutes, gauze, fabric, sheet, felt or sponge for liver homeostasis, gauze bandages, arterial graft or substitutes, bandages for skin surfaces, suture knot clip, orthopedic pins, clamps, screws, and plates, clips (e.g., for vena cava), staples, hooks, buttons, and snaps, bone substitutes (e.g., mandible prosthesis), bone void fillers, bone cements, intrauterine devices (e.g., spermicidal devices), draining or testing tubes or capillaries, surgical instruments, vascular implants or supports, vertebral discs, extracorporeal tubing for kidney and heart-lung machines, artificial skin and others.

The polyurethanes, polyureas, polyamideurethanes, and/or polyureaurethanes disclosed herein may also be used to fabricate degradable containers and packaging materials which can degrade in landfills in contrast to existing non-degradable materials which present environmental concerns.

The polyurethane material is believed to be especially useful for use as a tissue engineering scaffold, i.e., as a structure for the growth or regeneration of tissue. Polyurethanes may lend themselves to such uses since enzyme-catalyzed degradation may in some cases occur concurrently with the migration or growth of cells into the material, while desirably degrading in the process into its substantially non-toxic constituents. It is also possible, in some cases, that cells migrating into or located adjacent the matrix may themselves exude proteolytic enzymes that will mediate hydrolytic cleavage.

Such tissue engineering scaffolds may have applications in the regeneration of skin and other organs, bone, cartilage, ligaments, tendons, bladder and other tissues. The polyurethane material may also be useful in the production of sutures, which require good mechanical strength, as well as in the production of drug release matrices, in view of their need for degradation to non-toxic materials. The polyurethane material may also be useful for non-biomedical applications, where degradability into substantially non-toxic constituents is an asset. The polyurethane material lends itself to sterilization by such techniques as gamma radiation and ethylene oxide treatments.

Fibers made from the present polyurethanes, polyureas, polyamideurethanes, and/or polyureaurethanes can be knitted or woven with other fibers, either bioabsorbable or non-bioabsorbable, to form meshes or fabrics. Compositions including these polyurethanes, polyureas, polyamideurethanes, and/or polyureaurethanes may also be used as bioabsorbable coatings for surgical devices.

Another aspect of the invention is directed to compositions containing the polyurethanes, polyureas, polyamideurethanes, and/or polyureaurethanes described herein which may be used to make reinforced composites. Thus, for example, the polyurethane, polyurea, polyamideurethane, and/or polyureaurethane composition may form the matrix of the composite and may be reinforced with bioabsorbable or non-bioabsorbable fibers or particles. Alternatively, a matrix of any bioabsorbable or non-bioabsorbable polymer composition may be reinforced with fibers or particulate material made from compositions containing the polyurethanes, polyureas, polyamideurethanes, and/or polyureaurethanes described herein.

In a further embodiment, the polyurethanes, polyureas, polyamideurethanes, and/or polyureaurethanes described herein may be admixed with a filler. The filler may be in any particulate form, including granulate or staple fibers. While any known filler may be used, calcium carbonate, hydroxyapatite, tricalcium phosphate, bioglass or other bioceramics are the preferred fillers. Normally, from about 10 grams to about 400 grams of filler are mixed with about 100 grams of polymer. The filled, cross-linked polymers are useful, for example, as molding compositions.

It is further contemplated that one or more medico-surgically useful substances may be incorporated into compositions containing the polyurethanes, polyureas, polyamideurethanes, and/or polyureaurethanes described herein. Examples of such medico-surgically useful substances include, for example and without limitation, those which accelerate or beneficially modify the healing process when particles are applied to a surgical repair site. For example, articles made from compositions containing the presently disclosed polyurethanes, polyureas, polyamideurethanes, and/or polyureaurethanes may carry a therapeutic agent which will be deposited at the repair site. The therapeutic agent may be chosen for its antimicrobial properties, capability for promoting repair or reconstruction and/or new tissue growth. Antimicrobial agents such as broad spectrum antibiotics, for example and without limitation, gentamycin sulfate, erythromycin, or derivatized glycopeptides which are slowly released into the tissue, may be applied in this manner to aid in combating clinical and sub-clinical infections in a tissue repair site. To promote repair and/or tissue growth, one or several growth promoting factors may be introduced into the articles, e.g., fibroblast growth factor, bone growth factor, epidermal growth factor, platelet-derived growth factor, macrophage-derived growth factor, alveolar-derived growth factor, monocyte-derived growth factor, magainin, and the like. Examples of therapeutic indications include, without limitation, glycerol with tissue or kidney plasminogen activator to cause thrombosis, superoxide dismutase to scavenge tissue-damaging free radicals, tumor necrosis factor for cancer therapy or colony stimulating factor and interferon, interleukin-2 or other lymphokine to enhance the immune system.

A further aspect of the invention is directed to monomers wherein the isocyanate groups are replaced with isothiocyanates; and polymers produced therefrom. Specifically, this aspect of the invention is directed to isothiocyanate analogs of all isocyanate monomers.

Another aspect of the invention is directed to more reactive isocyanate monomers wherein the isocyanate(s) are prepared by reacting amino acids and derivative thereof (including but not limited to nitrophenylalanine, aminophenyl alanine, amino tyrosines) with compounds containing amino benzoic acid (para, meta, ortho), amino phenols (para, meta, ortho), amino salicylic acids (para, meta, ortho).

Another aspect of the invention is directed to more reactive isocyanate monomers prepared by reacting aliphatic amino acids and/or amines (including but not limited to hexamethylene diamine, 1,4-butane diames) with compounds containing amino benzoic acid (para, meta, ortho), amino phenols (para, meta, ortho), amino salicylic acids (para, meta, ortho). Structures of selected examples of these isocyanates are given below

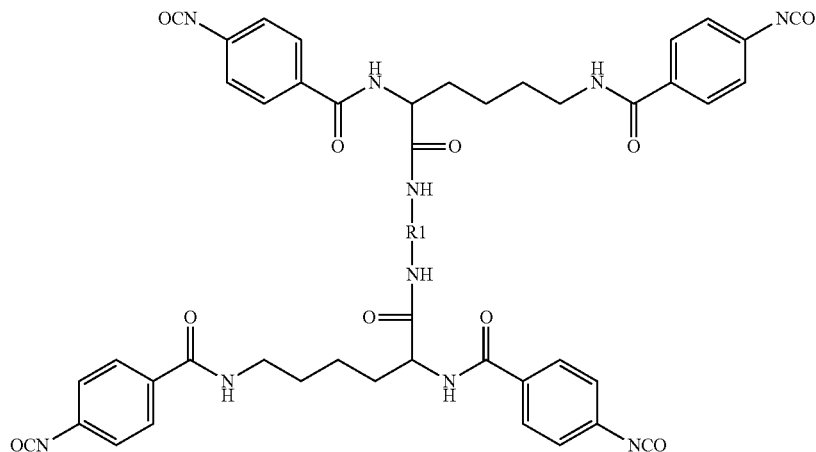

R1 is a residue of a diamine where in R1 is alkyl or aryl, arylalkyl, with alkyl chains containing a primary (long) chain of 2 up to 24 chain atoms (not including H), or alkyl substituted with analogs in which primary chain —$CH_2$— groups may be substituted with —O—, or —S—, and wherein the primary chain and aryl can be substituted with lower alkyl group(s) (such residue can be for example a residue of a PEG polyol). R1 is also can be L-lysine or aminophenyl alanine.

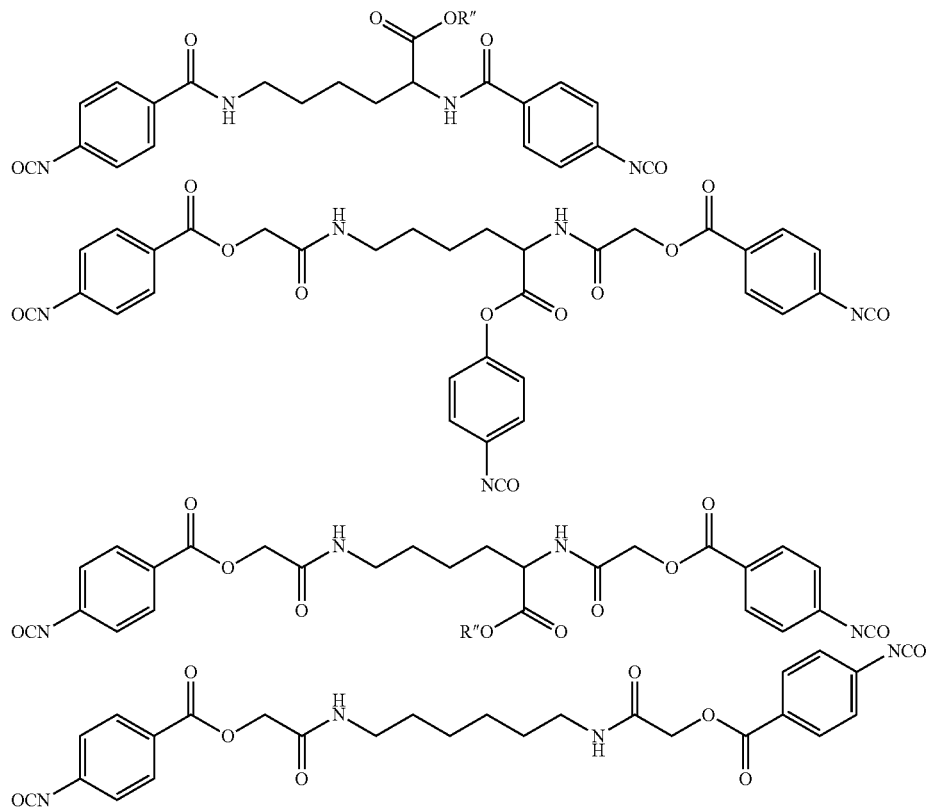

Another aspect of this invention is directed to amide acids by reacting amines and/or amino acids with unsymmetrical/symmetrical ether acids. Amines and amino acids include but are not limited to L-lysine, 1,6-hexamethylene diamine, 1,4-butane diamine, aminophenyl alanine, L-tyrosine, amino tyrosine, nitrophenyl alanine, aminophenyl alanine, and unsymmetrical/symmetrical ether acids.

Another aspect of this invention includes polyamines and polyisocyanates derived from nitrophenyl alanine. The structures of selected examples that represent these polyamines and polyisocyanates are given below

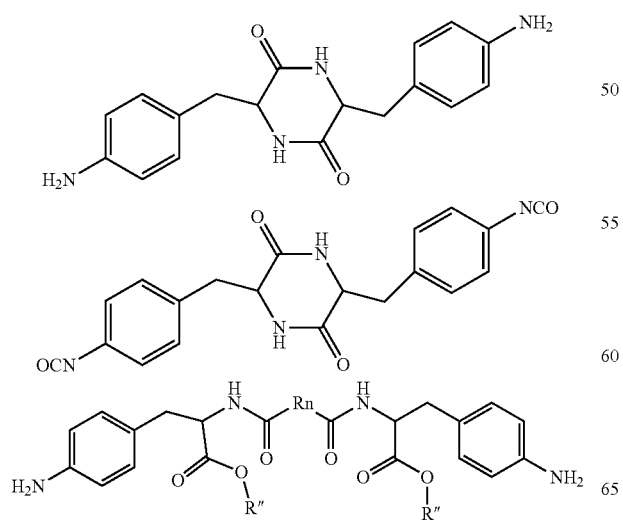

-continued

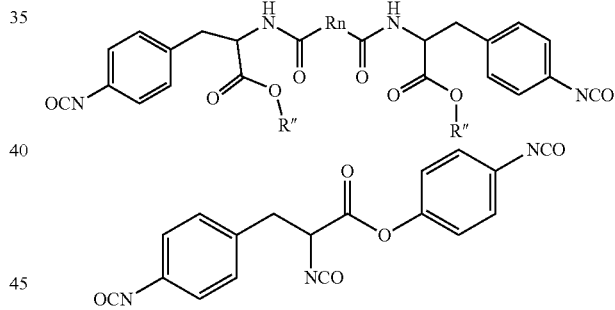

Where in Rn is residue of a diacid or residue of symmentrical or unsymmentrical ether acids The following examples are included to further illustrate the invention and are not to be considered as limiting the invention anyway. Melting points were measured for all products by using a Polmon (MP 96) melting point apparatus. For all the products, NMR was run using a Varian 200 MHz and tetramethylsilane as an internal standard.

EXAMPLES

Example 1. Synthesis of L-Lysine Methyl Ester Dihydrochloride

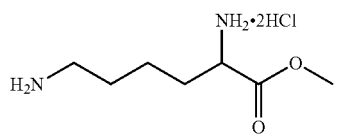

To a mixture of L-Lysine-Hydrochloride (100 g) in 1.75 L of methanol at 0° C. was bubbled dry HCl for 7 hours. The crude solid product was filtered, dried to get pure L-Lysine methyl ester dihydrochloride (117 g, 91.6%) as a white powder with a melting point of 204.5-206° C. The compound was characterized by 1H NMR (DMSO-$d_6$) δ 1.48 (m, 2H, $CH_2$), 1.68 (m, 2H, $CH_2$), 1.90 (m, 2H, $CH_2$), 2.80 (m, 2H, $CH_2$), 3.78 (s, 3H, Ester), 4.00 (t, 1H, CH), 8.20 (bs, 2H, $NH_2$), 8.70 (bs, 2H, $NH_2$).

Example 2. Synthesis of Benzyloxy Carbonyl Methoxy-Acetic Acid

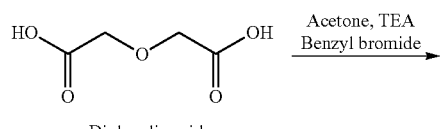

Diglycolic acid

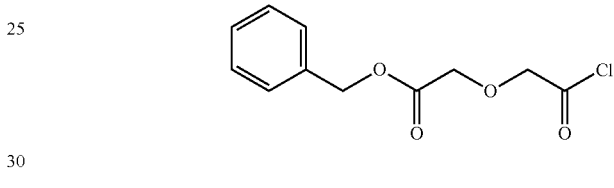

To a mixture of diglycolic acid (100 g), triethyl amine (136 ml) in Acetone (1000 ml) at 0° C. was added benzyl bromide (90 g) and stirred at room temperature for 20 hours. The reaction mixture was filtered to remove salts, distilled off acetone, poured onto 10% Sodium bicarbonate solution (1000 ml), washed with Ethyl acetate (200 ml×3), aqueous phase made acidic to pH 2 with dil Hydrochloric acid, extracted with ethyl acetate, washed with water (600 ml), dried over Sodium sulphate, distilled under reduced pressure to give pure Benzyloxy carbonyl methoxy-acetic acid (80 g) as light yellow syrup. The compound was characterized by $^1$HNMR (CDCl$_3$) δ 4.30 (s, 4H, $CH_2X_2$), 5.25 (s, 2H, $CH_2$), 7.40 (m, 5H, Ar), 9.25 (bs, 1H, COOH).

Example 3. Synthesis of Chloro Carbonyl Methoxy-Acetic Acid Benzyl Ester

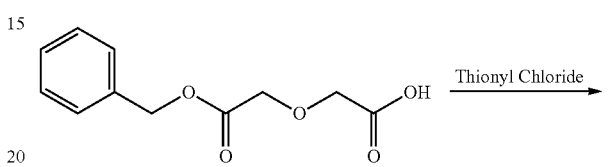

A solution of Benzyloxy carbonyl methoxy-acetic acid (40 g) and Thionyl chloride (80 ml) was stirred at reflux temperature for 3 hours. Excess Thionyl chloride was distilled off, to the residue was added toluene (100 ml) and distilled off the solvent completely to get chloro carbonyl methoxy-acetic acid benzyl ester (40 g) as a light brown liquid which was used without further purification.

Example 4. Synthesis of 2,6-Bis-(2-benzyloxycarbonylmethoxy-acetylamino)-hexanoic acid methyl ester

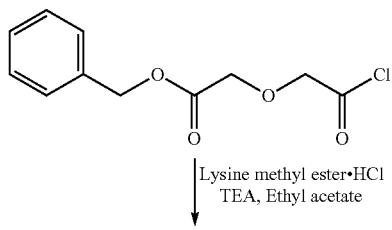

Lysine methyl ester•HCl
TEA, Ethyl acetate

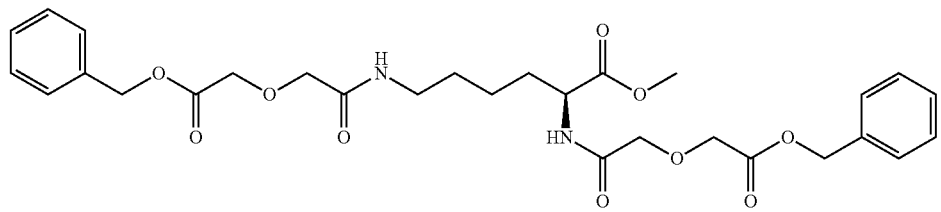

To a mixture of L-Lysine methyl ester dihydrochloride (30 g), Triethylamine (108 ml) in Ethyl acetate (750 ml) at 0° C. temperature was added chlorocarbonyl methoxy-acetic acid benzyl ester (77.7 g) drop wise, further stirred at room temperature for 10 hours. The solids were filtered off; the organic phase was washed with 5% sodium bicarbonate (600 ml), water (600 ml), dried over sodium sulphate and distilled. The crude product was purified by column chromatography on silica gel using Hexane:Ethyl acetate (8:2) to get pure 2,6-Bis-[2-(2-benzyloxy carbonyl methoxyethoxy)-acetylamino]-hexanoic acid methyl ester (55 g) as a light brown syrup with 97% purity as determined by HPLC. The product was characterized by $^1$H NMR (CDCl$_3$) δ 1.40 (m, 2H, CH$_2$), 1.50 (m, 2H, CH$_2$), 1.60 (m, 2H, CH$_2$), 1.80 (m, 2H, CH$_2$), 3.30 (m, 1H, CH), 3.70 (s, 3H, ester), 4.10 to 4.20 (m, 8H, 4 X CH$_2$), 4.60 (m, 1H, CH), 5.30 (s, 4H, 2 X CH$_2$), 6.90 (bs, 1H, NH), 7.45 (m, 10H, Ar).

Example 5. Synthesis of 2,6-Bis-(2-carboxymethoxy-acetylamino)-hexanoic acid methyl ester

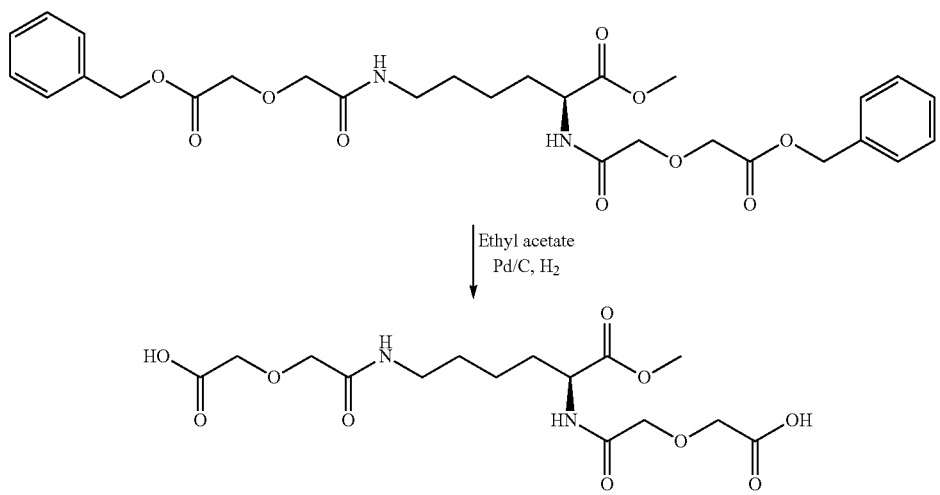

2,6-Bis-[2-(2-benzyloxy carbonyl methoxy-ethoxy)-acetylamino]-hexanoic acid methyl ester (6 g) was dissolved in Ethyl acetate (150 ml) in a pressure vessel, palladium on carbon (5%, 50% wet, 2 g) added and the mixture was stirred under an atmosphere of Hydrogen (5 kg) for 7 hours at a temperature of 45-50° C. The catalyst was removed by filtration and ethyl acetate was distilled off. The residue was washed with diisopropyl ether and solvents residue was removed by applying high vacuum to get pure 2,6-Bis-(2-carboxymethoxy-acetylamino)-hexanoic acid methyl ester (2.5 g) as light yellow syrup.

Example 6. Synthesis of polymer from 2,6-Bis-(2-benzyloxycarbonylmethoxy-acetylamino)-hexanoic acid methyl ester

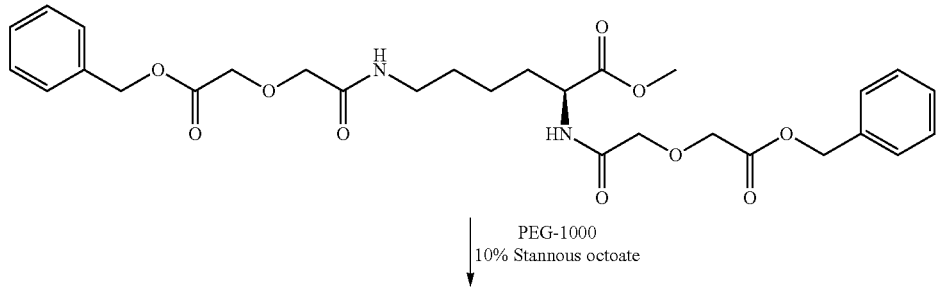

Into a clean flame dried 100 ml 4 neck round bottom flask equipped with a nitrogen inlet and a guard tube was added dibenzyl ester (15 g), PEG-1000 (26.22 g) and 10% Stannous octoate (2 ml) under nitrogen atmosphere. The reaction flask was placed in an oil bath with magnetic stirring and having distillation condenser. The reaction mixture was heated to a temperature of 220° C. and maintained at the same temperature for 3 hours. Benzyl alcohol formed was distilled off. The flask was brought down to room temperature and high vacuum was applied. Reaction mixture was heated to a temperature of 100° C. and maintained at the same temperature with high vacuum for 12 hours when the color of the reaction mixture changed to light brown thick syrup indicating formation of polymer. 38 g of polymer formed was poured into glass bottle.

Example 7. Synthesis of (2-Benzyloxy carbonyl methoxy-ethoxy)-acetic acid

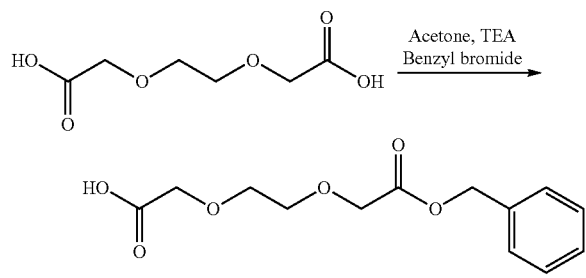

To a mixture of 3,6-Dioxaoctanoic acid (100 g), Triethylamine (131 g) in Acetone (1000 ml) at 0° C. was added Benzyl bromide (95.2 g) drop wise. The solution was further stirred at room temperature overnight. The solids were filtered off and acetone was distilled off. The residue was dissolved in saturated sodium bicarbonate (1000 ml) and washed with ethyl acetate. The aqueous phase was made acidic with HCl and extracted with ethyl acetate (1500 ml) and dried over sodium sulphate and distilled to get pure (2-Benzyloxy carbonyl methoxy-ethoxy)-acetic acid (80 grams) as a light yellow syrup.

Example 8. Synthesis of (2-Chlorocarbonylmethoxy-ethoxy)-acetic acid benzyl ester

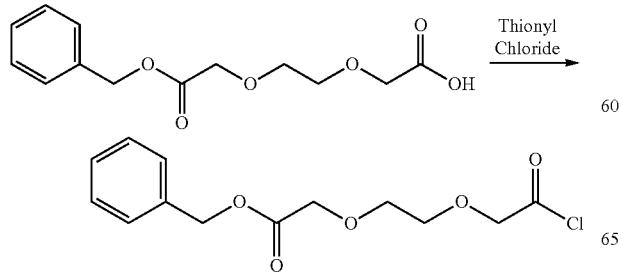

A solution of (2-Benzyloxy carbonyl methoxy-ethoxy)-acetic acid (40 g) and thionyl chloride (80 ml) was stirred at reflux temperature for 3 hours. Excess thionyl chloride was distilled off and to the residue was added Toluene (100 ml). The solvent was distilled off completely to yield (2-Chlorocarbonylmethoxy-ethoxy)-acetic acid benzyl ester (40 g) as a light brown liquid which was used without further purification.

Example 9. Synthesis of 2-[2-(2-Benzyloxy carbonyl methoxy-ethoxy)-acetylamino]-3-(4-hydroxy-phenyl)-propionic acid ethyl ester

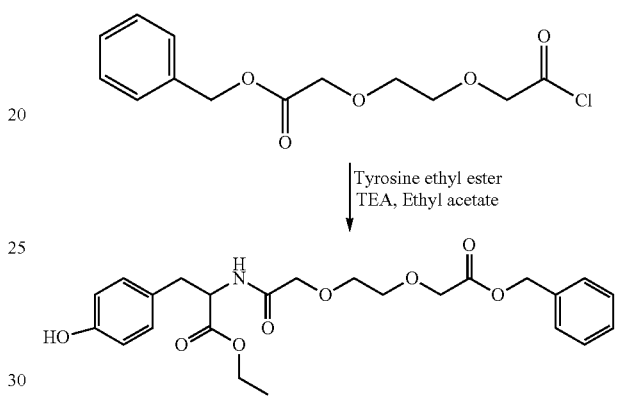

To a mixture of Tyrosine ethyl ester (20 g) and Triethylamine (20 ml) in Ethyl acetate (300 ml) at 0° C. was added (2-Chlorocarbonylmethoxy-ethoxy)-acetic acid benzyl ester (28 g) drop wise. The solution was further stirred at room temperature for 36 hours. The solids were filtered off and the organic phase was washed with 5% sodium bicarbonate (200 ml) and water (200 ml). The organic phase was dried over sodium sulphate and distilled. The crude was purified by column chromatography on silica gel using Hexane:Acetone (7:3) to yield pure 2-[2-(2-Benzyloxy carbonyl methoxy-ethoxy)-acetylamino]-3-(4-hydroxy-phenyl)-propionic acid ethyl ester (20 g) as a light brown syrup. The product was characterized by HPLC: 99% and $^1$H NMR (CDCl$_3$) δ 1.20 (t, 3H, CH$_3$), 2.90 to 3.10 (m, 2H, CH$_2$), 3.60 (m, 4H, 2 X CH$_2$), 3.90 (s, 2H, CH$_2$), 4.10 (m, 4H, 2 X CH$_2$), 4.85 (m, 1H, CH), 5.20 (s, 2H, CH$_2$), 6.70 (d, 2H, Ar), 7.00 (d, 2H, Ar), 7.45 (m, 6H, NH & Ar).

Example 10. Synthesis 2-[2-(2-Carboxy methoxy-ethoxy)-acetylamino]-3-(4-hydroxy-phenyl)-propionic acid ethyl ester

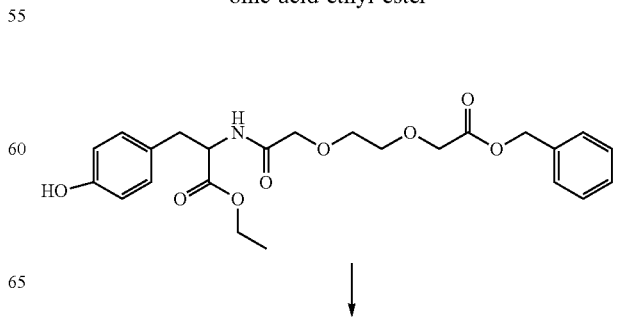

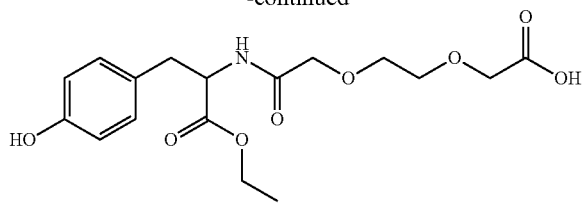

2-[2-(2-Benzyloxy carbonyl methoxy-ethoxy)-acetylamino]-3-(4-hydroxy-phenyl)-propionic acid ethyl ester (5 g) was dissolved in ethyl acetate (200 ml) in a pressure vessel. Palladium on carbon (5%, 50% wet, 2 g) was added and the mixture was stirred under an atmosphere of hydrogen (6 kg) for 9 hours at a temperature of 45-50° C. The catalyst was removed by filtration and distilled off ethyl acetate and the residue was washed with Diisopropyl ether and solvents residue was removed by applying high vacuum to get pure 2-[2-(2-Carboxy methoxy-ethoxy)-acetylamino]-3-(4-hydroxy-phenyl)-propionic acid ethyl ester (2.2 g) as light yellow syrup. The product was characterized by $^1$H NMR which showed the presence of some impurities and hence was purified by column chromatography.

Example 11. Synthesis of polymer from 2-[2-(2-Benzyloxy carbonyl methoxy-ethoxy)-acetylamino]-3-(4-hydroxy-phenyl)-propionic acid ethyl ester

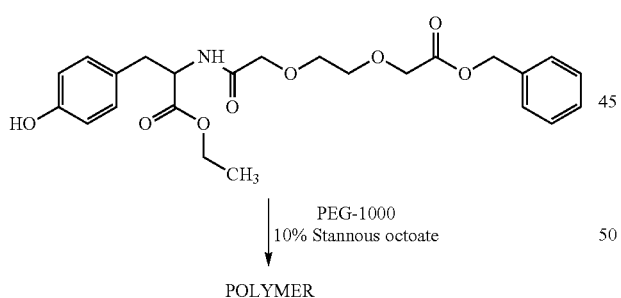

Into a clean flame dried 100 ml 4 neck round bottom flask equipped with $N_2$ bubbler and guard tube was charged dibenzyl ester (6 g), PEG-1000 (13.10 g) and 10% stannous octoate (1 ml) under nitrogen atmosphere. The flask was placed in an oil bath with magnetic stirring and having distillation condenser. Reaction mixture was heated to a temperature of 210 to 220° C. and maintained at the same temperature for 4 hours when distillation of Benzyl alcohol was observed which was confirmed by TLC. Further heating was cut off and at room temperature high vacuum was applied. Reaction mixture was kept at a temperature of 80 to 100° C. and maintained at the same temperature with high vacuum for 8 hours. Reaction mixture was changed to light brown thick syrup indicating formation of polymer. 18 g of Reaction mixture poured into glass bottle.

Example 12. Synthesis of {[6-(2-Carboxy methoxy-acetylamino)-hexylcarbamoyl]-methoxy}-acetic acid

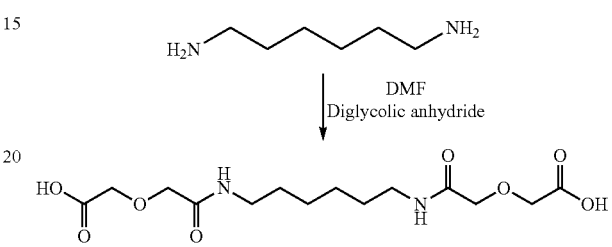

To a solution of Diglycolic anhydride (30 g) in Dimethylformamide (85 ml) at 60° C. was added dropwise a solution of 1,6-Hexamethylene diamine (11.6 g) in Dimethylformamide (50 ml). The reaction mixture was stirred at the same temperature for 1 hour. The reaction mixture was cooled to 0° C. and maintained for 3 hours. The solid was filtered and washed with chloroform and dried to get pure {[6-(2-Carboxy methoxy-acetylamino)-hexylcarbamoyl]-methoxy}-acetic acid (9 g) as white powder with a melting point of 178-180° C. The compound was characterized by $^1$H NMR (DMSO-$d_6$) δ1.25 (m, 2H, $CH_2$), 1.55 (m, 2H, $CH_2$), 2.80 (m, 2H, $CH_2$), 3.90 (s, 4H, 2 X $CH_2$), 7.90 (bs, 1H, NH).

Example 13. Synthesis of (2-Chloro-N-[6-(2-chloro-acetylamino)-hexyl]-acetamide)

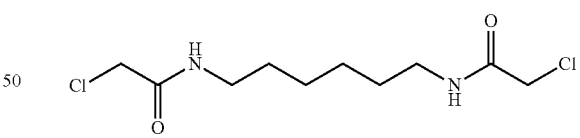

To a mixture of 1,6-Hexamethylene diamine (150 g) and Sodium bicarbonate (645 g) in ethyl acetate (2500 ml) at 0° C. was added dropwise chloroacetyl chloride (257 ml). The reaction mixture was further stirred at room temperature for 1 hour followed by heating to 55° C. and maintained for 6 hours. The solvent was distilled off and the residue was taken into cold water. The filtered solid was separated and purified by recrystallisation from ethyl acetate to get pure (2-Chloro-N-[6-(2-chloro-acetylamino)-hexyl]-acetamide) (200 g) as white powder with a melting point of 134.5-136.7° C. The compound was characterized by $^1$H NMR (DMSO-$d_6$) δ 1.24 (m, 2H, $CH_2$), 1.42 (m, 2H, $CH_2$), 3.06 (m, 2H, $CH_2$), 4.02 (s, 2H, $CH_2$), 8.19 (bs, 1H, NH).

Example 14 Synthesis of (Benzyloxy-acetic acid {6-[2-(2-benzyloxy-acetoxy) acetylamino]-hexylcarbamoyl}-methyl ester)

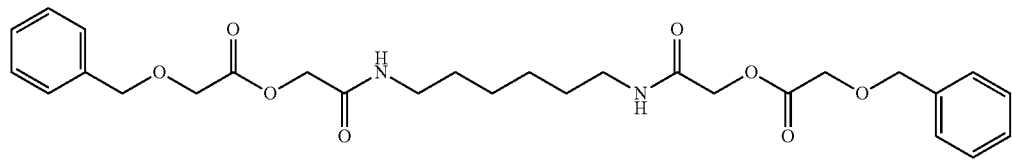 [SMILES: O=C(COC(=O)COCc1ccccc1)NCCCCCCNC(=O)COC(=O)COCc1ccccc1]

To a solution of 2-Chloro-N-[6-(2-chloro-acetylamino)-hexyl]-acetamide (200 gm) and triethyl amine (400 ml) in Acetone (2000 ml) at room temperature was added dropwise Benzyloxy acetic acid (350 g). The solution was further stirred at reflux temperature overnight. The reaction mixture was poured onto cold water and solids were filtered, dried and the crude product was purified by recrystallisation from Ethyl acetate to yield pure (Benzyloxy-acetic acid-{6-[2-(2-benzyloxy-acetoxy)-acetylamino]-hexylcarbamoyl}-methyl ester) (190 g) as white powder with a melting point of 101-103° C. The product was characterized by $^1$H NMR (CDCl$_3$+DMSO-d$_3$) δ 1.24 (m, 2H, CH$_2$), 1.43 (m, 2H, CH$_2$), 3.15 (t, 2H, CH$_2$), 4.15 (s, 2H, CH$_2$), 4.48 (s, 2H, CH$_2$), 4.56 (s, 2H, CH$_2$), 7.30 (m, 5H, Ar), 7.46 (t, 1H, NH).

Example 15 Synthesis of (Hydroxy-acetic acid {6-[2-(2-hydroxy-acetoxy)-acetylamino]-hexylcarbamoyl}-methyl ester)

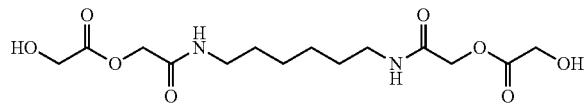 [SMILES: O=C(COC(=O)CO)NCCCCCCNC(=O)COC(=O)CO]

Benzyloxy-acetic acid {6-[2-(2-benzyloxy-acetoxy)-acetyl amino]-hexylcarbamoyl}-methyl ester (250 g) was dissolved in DMF (600 ml) in a pressure vessel (Autoclave), 50% wet palladium on carbon (10%, 75 g) was added and the mixture was stirred under hydrogen atmosphere (8 Kg) for 72 hours at 70° C. The catalyst was removed by filtration and 80% of the DMF was distilled off. The crude product was precipitated by adding to Methanol and filtered and dried to get pure (Hydroxy-acetic acid {6-[2-(2-hydroxy-acetoxy)-acetylamino]-hexylcarbamoyl}-methyl ester) (90 g) as a white powder with a melting point of 156-158° C. The pure product was characterized by $^1$HNMR (CDCl$_3$+DMSO-d$_6$) δ 1.22 (m, 2H, CH$_2$), 1.38 (m, 2H, CH$_2$), 3.06 (m, 2H, CH$_2$), 4.15 (d, 2H, CH$_2$), 4.48 (s, 2H, CH$_2$), 5.42 (t, 1H, OH), 7.98 (bt, 1H, NH).

Example 16 Synthesis of Benzyloxy Carbonyl Methoxy-Acetic Acid

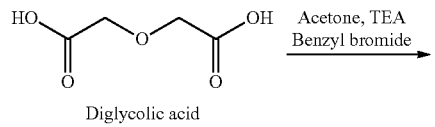

Diglycolic acid

-continued

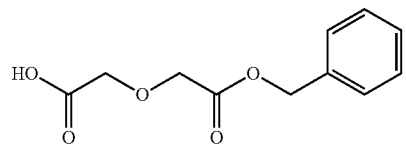

To a mixture of Diglycolic acid (100 g), Triethyl amine (136 ml) in Acetone (1000 ml) at 0° C. was added Benzyl bromide (90 g). The solution was stirred at room temperature for 20 hours. The reaction mixture was filtered to remove salts and acetone was distilled off. The reaction mixture was poured onto 10% Sodium bicarbonate solution (1000 ml), washed with Ethyl acetate (600 ml). The aqueous phase was made acidic to pH 2 with dilute Hydrochloric acid. The organic compound was extracted with ethyl acetate and washed with water (600 ml) and dried over sodium sulphate. The organic solvent was distilled under reduced pressure to give pure Benzyloxy carbonyl methoxy-acetic acid (80 g) as light yellow syrup. The compound was characterized by $^1$HNMR (CDCl$_3$) δ 4.30 (s, 4H, CH$_2$X 2), 5.25 (s, 2H, CH$_2$), 7.40 (m, 5H, Ar), 9.25 (bs, 1H, COOH).

Example 17 Synthesis of Chloro Carbonyl Methoxy-Acetic Acid Benzyl Ester

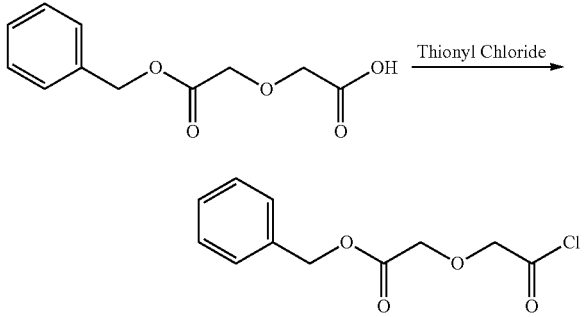 [SMILES: O=C(O)COCC(=O)OCc1ccccc1 ; O=C(Cl)COCC(=O)OCc1ccccc1]

A solution of Benzyloxycarbonyl methoxy-acetic acid (40 g) and Thionyl Chloride (80 ml) was stirred at reflux temperature for 3 hours. Excess Thionyl Chloride was distilled off and to the residue was added Toluene (100 ml). The solvent was distilled off completely to get chlorocarbonyl methoxy-acetic acid benzyl ester (40 g) as a light brown liquid which was used without further purification.

Example 18 Synthesis of 2-(2-Benzyloxy carbonyl methoxy-acetylamino)-3-(4-hydroxy-phenyl)-propionic acid ethyl ester

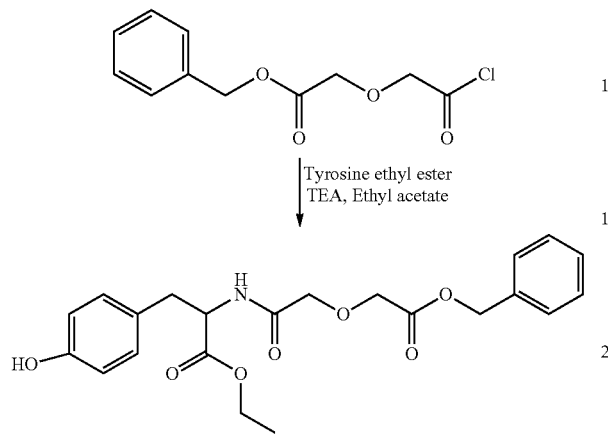

To a mixture of Tyrosine ethyl ester (40 g) and Triethylamine (40 ml) in Ethyl acetate (600 ml) at 0° C. temperature was added Chloro carbonyl methoxy-acetic acid benzyl ester (46.5 g) drop wise. The reaction mixture was further stirred at room temperature for 10 hours. The solids were filtered off and the organic phase was washed with 5% sodium bicarbonate solution (600 ml) and water (600 ml). It was dried over sodium sulphate and organic solvent was distilled. The crude was purified by column chromatography on silica gel using Hexane:Ethyl acetate (8:2) to get pure 2-(2-Benzyloxy carbonyl methoxy-acetyl amino)-3-(4-hydroxy-phenyl)-propionic acid ethyl ester (30 g) as a light yellow syrup. The product was characterized by $^1$H NMR (CDCl$_3$) δ 1.20 (t, 3H, CH$_3$), 2.90 to 3.10 (m, 2H, CH$_2$), 4.10 to 4.30 (m, 6H, 3 X CH$_2$), 4.85 (q, 1H, CH), 5.20 (s, 2H, CH$_2$), 5.80 (bs, 1H, NH), 6.70 (d, 2H, Ar), 7.00 (d, 2H, Ar), 7.40 (m, 5H, Ar).

Example 19 Synthesis of 2-(2-Carboxy methoxy-acetylamino)-3-(4-hydroxy-phenyl)-propionic acid ethyl ester

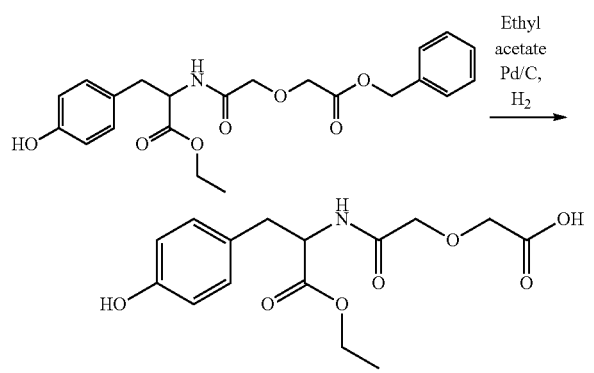

2-(2-Benzyloxy carbonyl methoxy-acetyl amino)-3-(4-hydroxy-phenyl)-propionic acid ethyl ester (6 g) was dissolved in Ethyl acetate (150 ml) in a pressure vessel, palladium on carbon (5%, 50% wet, 2 g) added and the mixture stirred under an atmosphere of Hydrogen (5 kg) for 7 hours at a temperature of 45-50° C. The catalyst was removed by filtration and Ethyl acetate was distilled off and the residue was washed with diisopropyl ether and solvent residue was removed by applying high vacuum to get pure 2-(2-Carboxy methoxy-acetylamino)-3-(4-hydroxy-phenyl)-propionic acid ethyl ester (2.5 grams) as light yellow syrup. The product was characterized by $^1$H NMR which showed the presence of some impurities and hence was purified by column chromatography.

Example 20 Synthesis of polymer from 2-(2-Benzyloxy carbonyl methoxy-acetylamino)-3-(4-hydroxy-phenyl)-propionic acid ethyl ester

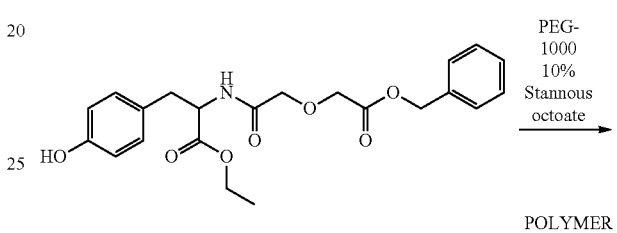

POLYMER

A clean flame dried 100 ml 4 neck RB flask equipped with N$_2$ bubbler and guard tube was placed in a oil bath with magnetic stirring and having distillation condenser. Into this flask was added Dibenzyl ester (15 g) and PEG-1000 (26.22 g) and 10% stannous octoate (2 ml) under nitrogen atmosphere. Reaction mixture was heated to a temperature of 220° C. and maintained at the same temperature for 4 hours. During the process Benzyl alcohol was distilled as confirmed by the TLC. Heating was cut off and at room temperature high vacuum was applied. Reaction mixture was heated to a temperature of 100° C. and maintained at the same temperature with high vacuum for 10 hours. Reaction mixture was changed to light brown thick syrup indicating formation of polymer. 31 g of Reaction mixture poured into glass bottle.

Example 21 Synthesis of L-Lysine Methyl Ester Dihydrochloride

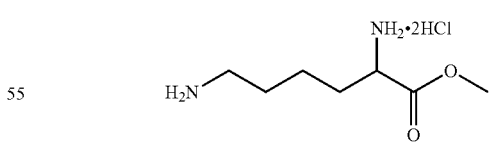

A mixture of L-Lysine-Hydrochloride (100 g) in methanol (1.75 lit) at 0° C. was bubbled dry HCl for 7 hours. The crude solid product was filtered and dried to get pure L-Lysine methyl ester dihydrochloride (117 g) as a white powder with a melting point of 204.5-206° C. The product was characterized by $^1$H NMR (DMSO-d$_6$) δ 1.48 (m, 2H, CH$_2$), 1.68 (m, 2H, CH$_2$), 1.90 (m, 2H, CH$_2$), 2.80 (m, 2H, CH$_2$), 3.78 (s, 3H, Ester), 4.00 (t, 1H, CH), 8.20 (bs, 2H, NH$_2$), 8.70 (bs, 2H, NH$_2$).

Example 22 Synthesis of (2-Benzyloxy carbonyl methoxy-ethoxy)-acetic acid

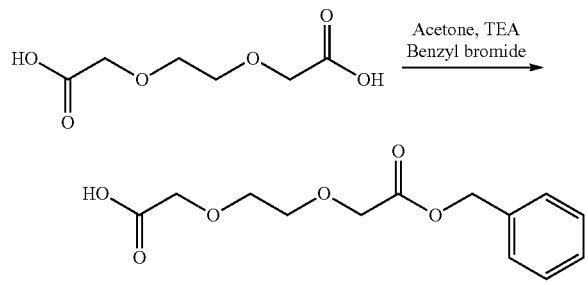

To a mixture of 3,6-Dioxaoctanoic acid (100 g), Triethylamine (131 g) in Acetone (1000 ml) at 0° C. temperature was added Benzyl bromide (95.2 g) drop wise. The solution was left for stirring overnight. The solids were filtered off and acetone was distilled off. The residue was dissolved in saturated sodium bicarbonate (1000 ml), and washed with Ethyl acetate. The aqueous phase was made acidic with HCl and extracted with Ethyl acetate (1500 ml). The organic layer was dried over sodium sulphate and the solvent was distilled off to yield pure (2-Benzyloxy carbonyl methoxy-ethoxy)-acetic acid (80 g) as a light yellow syrup.

Example 23 Synthesis of (2-Chlorocarbonylmethoxy-ethoxy)-acetic acid benzyl ester

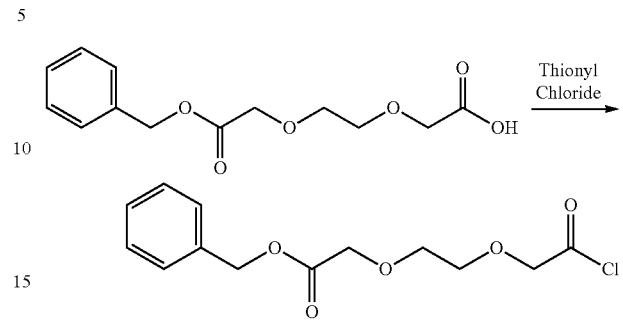

A solution of (2-Benzyloxy carbonyl methoxy-ethoxy)-acetic acid (40 g) and Thionyl Chloride (80 ml) was stirred at reflux temperature for 3 hours. Excess Thionyl Chloride was distilled off and to the residue was added Toluene (100 ml). The solvent was distilled off completely to get (2-Chlorocarbonylmethoxy-ethoxy)-acetic acid benzyl ester (40 g) as a light brown liquid which was used without further purification.

Example 24 Synthesis of 2,6-Bis-[2-(2-benzyloxy carbonyl methoxy-ethoxy)-acetylamino]-hexanoic acid methyl ester

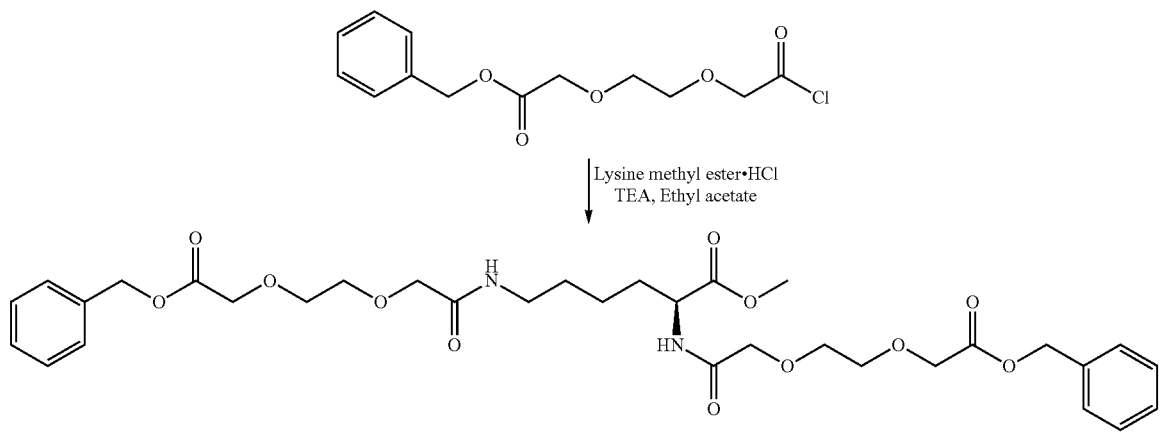

To a mixture of L-Lysine methyl ester dihydrochloride (10 g) and Triethylamine (36 ml) in Ethyl acetate (750 ml) at 0° C. temperature was added (2-Chlorocarbonylmethoxy-ethoxy)-acetic acid benzyl ester (40 g) drop wise. The solution was further stirred at room temperature for 16 hours. The solids were filtered off and the organic phase was washed with 5% sodium bicarbonate (200 ml) solution and water (200 ml). It was dried over sodium sulphate and organic layer was distilled off. The crude product was purified by column chromatography on silica gel using Hexane:Acetone (8:2) to get pure 2,6-Bis-[2-(2-benzyloxy carbonyl methoxy-ethoxy)-acetylamino]-hexanoic acid methyl ester (17 g) as a light yellow syrup. The product was characterized by HPLC: 98.5% and $^1$H NMR (CDCl$_3$) δ 1.40 (m, 2H, CH$_2$), 1.55 (m, 2H, CH$_2$), 1.70 (m, 2H, CH$_2$), 1.90 (m, 2H, CH$_2$), 3.30 (m, 1H, CH), 3.65 (m, 11H, Ester and 4 X CH$_2$), 4.00 (m, 4H, 2 X CH$_2$), 4.20 (m, 4H, 2 X CH$_2$), 4.60 (m, 1H, NH), 5.20 (s, 4H, 2 X CH$_2$), 7.10 (bs, 1H, NH), 7.40 (m, 10H, Ar).

Example 25 Synthesis of 2,6-Bis-[2-(2-carboxy methoxy-ethoxy)-acetylamino]-hexanoic acid methylester

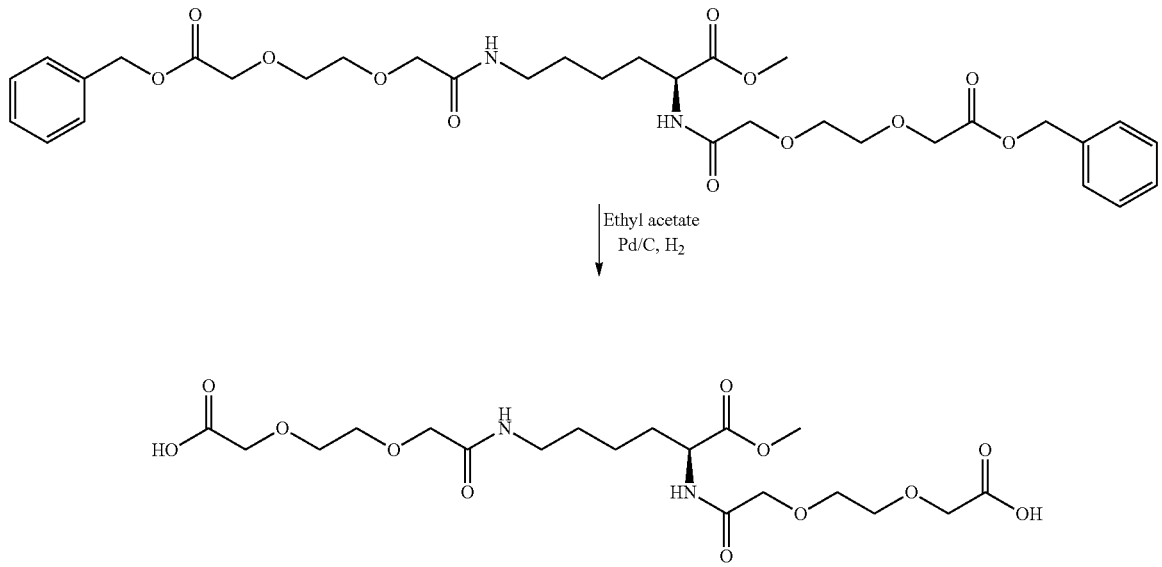

2,6-Bis-[2-(2-benzyloxy carbonyl methoxy-ethoxy)-acetylamino]-hexanoic acid methyl ester (7 g) was dissolved in Ethyl acetate (200 ml) in a pressure vessel, palladium on carbon (5%, 50% wet, 3 g) added and the mixture stirred under an atmosphere of Hydrogen (5 kg) for 8 hours at a temperature of 45-50° C. The catalyst was removed by filtration and ethyl acetate was distilled off. The residue was washed with diisopropyl ether and solvent residue was removed by applying high vacuum to get pure 2,6-Bis-[2-(2-carboxy methoxy-ethoxy)-acetylamino]-hexanoic acid methylester (3 g) as light yellow syrup. The product was characterized by $^1$H NMR which showed the presence of some impurities and hence was purified by column chromatography.

Example 26 Synthesis of polymer from 2,6-Bis-[2-(2-benzyloxy carbonyl methoxy-ethoxy)-acetylamino]-hexanoic acid methyl ester A clean flame dried 100 ml 4 neck RB flask equipped with $N_2$ bubbler and guard tube was placed in a oil bath with magnetic stirring and having distillation condenser. Into the flask were added dibenzyl ester (5 g), PEG-1000 (7.6 g) and 10% stannous octoate (1 ml) under nitrogen atmosphere. The reaction mixture was heated to a temperature of 210 to 220° C. and maintained at the same temperature for 4 hours. During the process ~0.5 ml of Benzyl alcohol was distilled off. The heating was cut off. At room temperature high vacuum was applied. Reaction mixture was heated to a temperature of 80 to 100° C. and maintained at the same temperature under high vacuum for 8 hours. Reaction mixture was changed to light brown thick syrup indicating formation of polymer. 10 grams of reaction mixture was poured into glass bottle

Example 27 Diisocyanate from 4-Nitrophenylalanine Stearyl Ester

2-Isocyanato-3-(4-isocyanato-phenyl)-propionic acid Stearyl ester is prepared using the following Scheme-I:

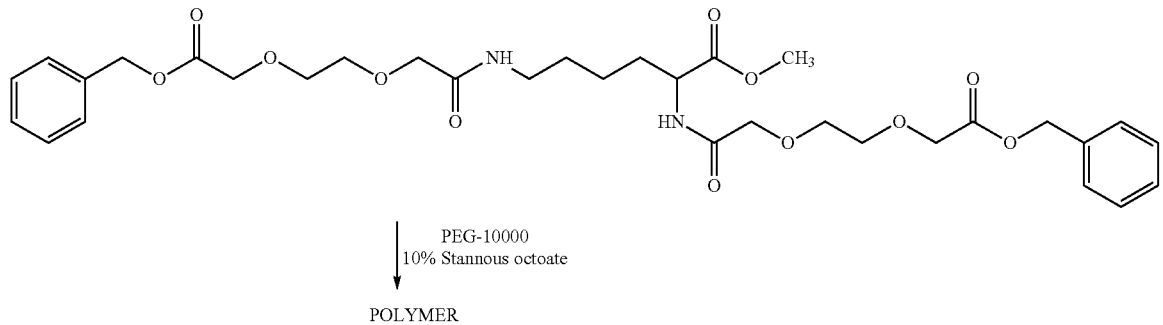 [SMILES: COC(=O)C(CCCCNC(=O)COCCOCC(=O)OCc1ccccc1)NC(=O)COCCOCC(=O)OCc1ccccc1]

Scheme-I

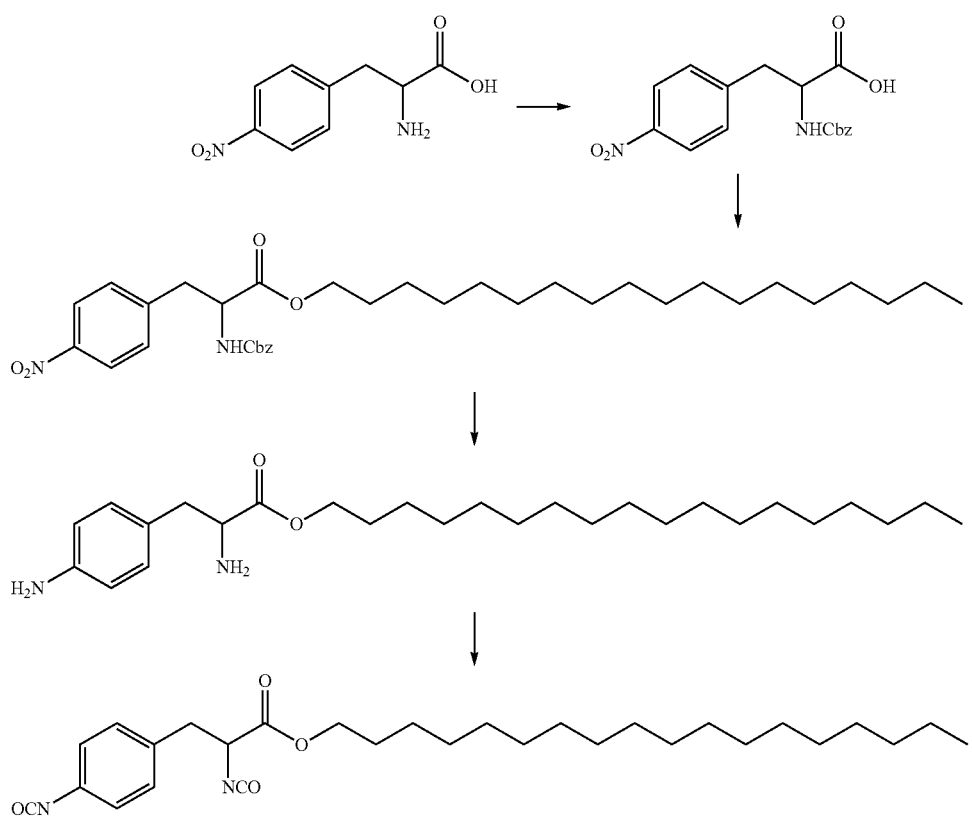

The above crude DiNCO was recrystllised from Toluene/Hexane and isolated 7 grams of the pure product as white powder with a MP of 58-60° C. and confirmed by NMR and IR.

Example 28: Diisocyanate from 4-Nitrophenylalanine 4-NitroBenzoic acid Methyl Ester 2-(4-Isocyanato-benzoylamino)-3-(4-isocyanato-phenyl)-propionic acid methyl ester is prepared using the following scheme-II Scheme-II

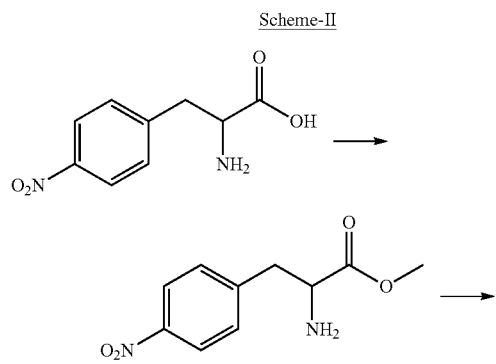

-continued

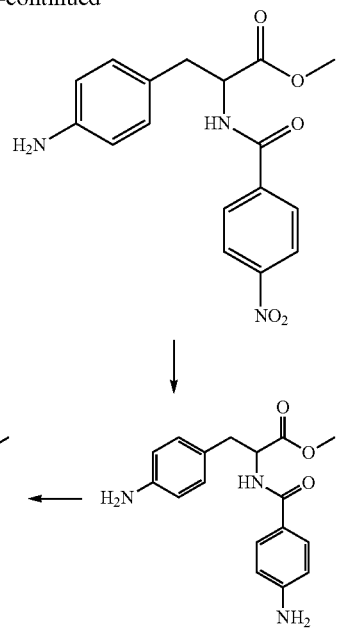

The above 35 grams of the Amine from the first batch was converted to DiNCO, reaction has progressed by TLC, and isolated 35 grams of a sample as light brown syrup. The crude product has only 81% NCO by titration. After putification, it has 99% therotical NCO.

Example 29: Triisocyanate from 4-Nitrophenylalanine 4-NitroBenzoic acid 4-Nitro phenol
2-(4-Isocyanato-benzoylamino)-3-(4-isocyanato-phenyl)-propionic acid 4-isocyanato-phenyl ester is prepared using the following Scheme-III:
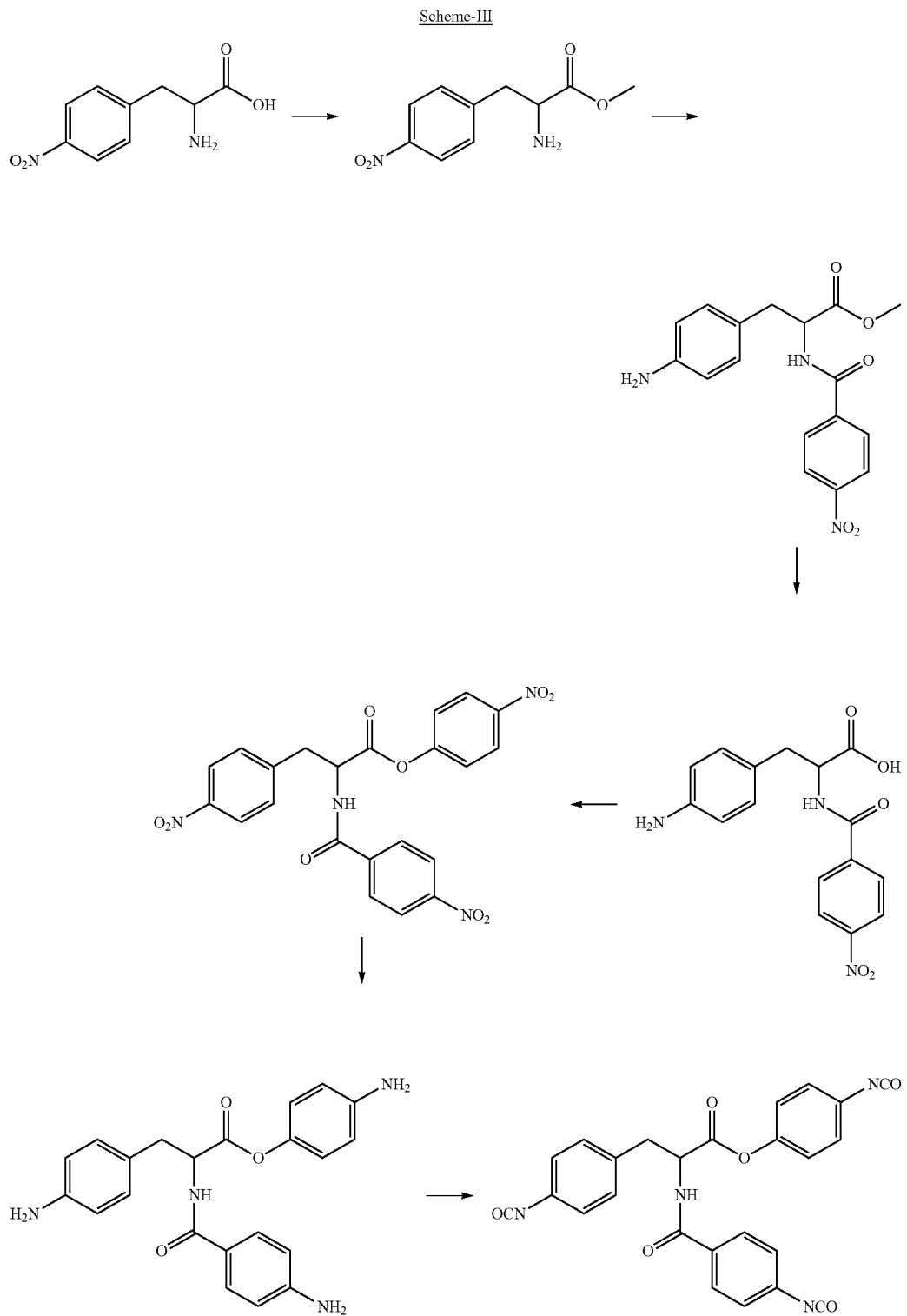

Example 30: Tetraisocyanate from 4-Nitrophenylalanine Ethylene Glycol Lactate Linker 2-Isocyanato-3-(4-isocyanato-phenyl)-propionic acid 1-(2-{2-[2-isocyanato-3-(4-isocyanato-phenyl)-propionyloxy]-propionyloxy}-ethoxycarbonyl)-ethyl ester is prepared using the following Scheme-IV:

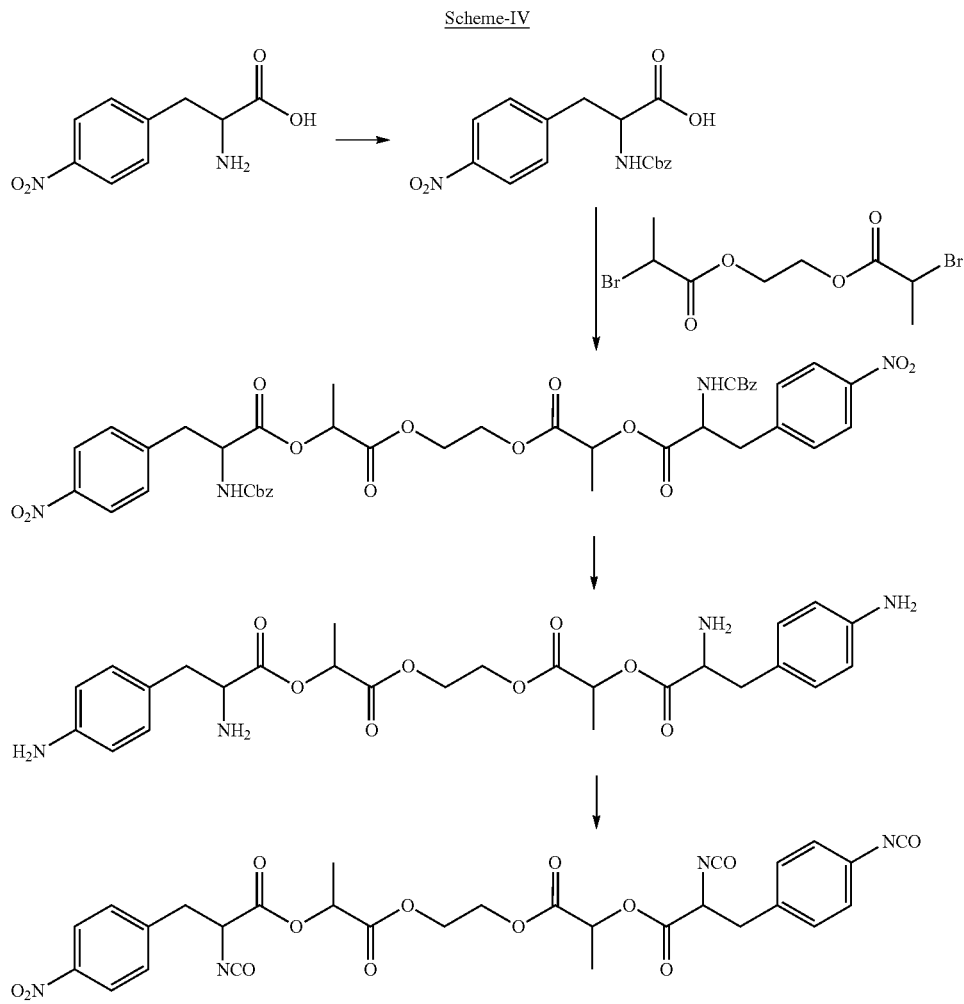

Example 31: Synthesis of 4-Nitro Phenyl Alanine Methyl Ester Hydrochloride

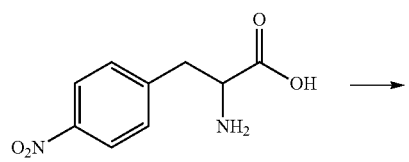

To a mixture of 4-nitro phenyl alanine (15 g) and DMAP (2.12 g) in methanol (150 ml) at 0° C. was added thionyl chloride (7.8 g) dropwise and later heated to reflux for 5 hours. The solvent was distilled off under vacuum. The solid separated was filtered and purified from Methanol and Diisopropyl ether to yield 4-nitrophenylalanine methyl ester hydrochloride (12 g) as white powder with a melting point of 218-220° C. and a purity of 99% as determined by HPLC.

Example 32: Synthesis of 3-(4-nitro-phenyl)-2-(4-nitro-benzoylamino)-propionic acid methyl ester

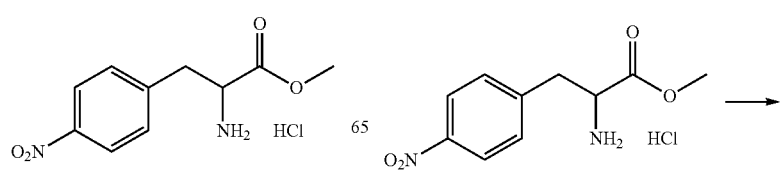

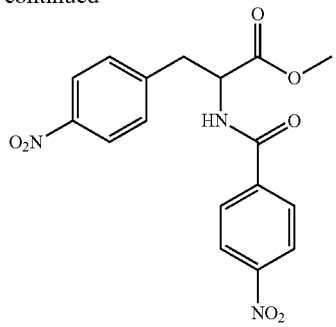

To a mixture of 4-nitro phenyl alanine methyl ester hydrochloride (250 g) and triethylamine (320 ml) maintained at 0° C. in dimethylformamide (1250 ml) under nitrogen atmosphere was added dropwise 4-nitro benzoyl chloride (143 g) and allowed to slowly come to room temperature followed by further stirring for 2 hours. The reaction mixture was poured onto cold water and the precipitated solid was filtered off, dried and recrystallized from mixture of dimethylformamide:methanol (2:1) to yield pure 3-(4-nitro-phenyl)-2-(4-nitro-benzoylamino)-propionic acid methyl ester (260 g) as light brown powder with a melting point of 237-239° C. The product was characterized by 1H NMR (DMSOd6) δ 3.10-3.30 (m, 2H, CH$_2$), 3.60 (s, 3H, OCH3), 4.80 (m, 1H, CH), 7.50 (d, 2H, Ar), 8.00 (d, 2H, Ar), 8.10 (d, 2H, Ar), 8.25 (d, 2H, Ar), 9.20 (d, 1H, NH)

Example 33: Synthesis of 3-(4-Amino-phenyl)-2-(4-amino-benzoylamino)-propionic acid methyl ester

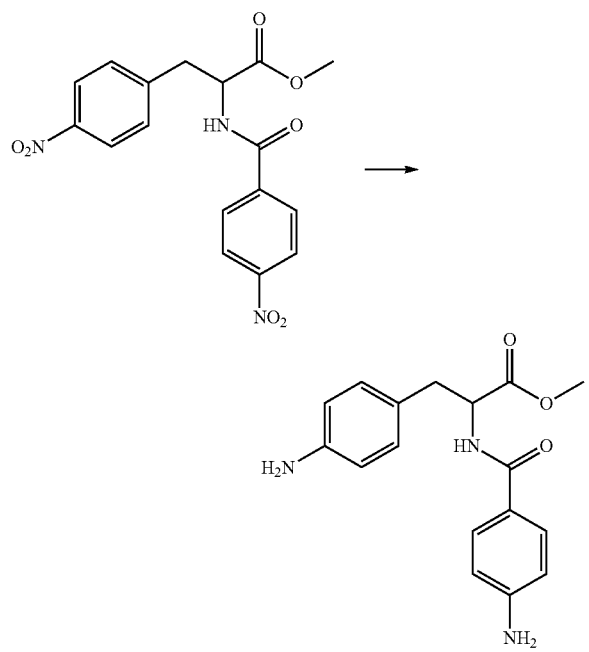

3-(4-nitro-phenyl)-2-(4-nitro-benzoylamino)-propionic acid methyl ester (80 g) was dissolved in a mixture of dimethylformamide:ethyl acetate (2.5:7.5; 2400 ml) in a pressure vessel. 10% Palladium carbon (30 grams, 50% wet) was added and the reaction mixture was stirred under an atmosphere of hydrogen (5 Kg) at 50° C. for 5 hours. The temperature of the reaction mixture was brought to 200° C. and the catalyst was removed by filtration. The solvent was distilled off and the diamine was precipitated by adding diisopropyl ether (500 ml) and methanol (50 ml). The solid diamine was filtered and dried to yield pure 2-Amino-3-(4-amino-phenyl)-propionic acid octadecyl ester (55 g) as off white powder with a melting point of 178-180° C. and a purity of 99% as determined by HPLC. The diamine was further characterized by 1H NMR (CDCl3+DMSOd6) δ 2.90-3.00 (m, 2H, CH$_2$), 3.60 (s, 3H, OCH3), 4.30 (bs, 2H, NH2), 4.50 (m, 1H, CH), 5.10 (bs, 2H, NH2), 6.50 (m, 4H, Ar), 6.90 (d, 2H, Ar), 7.50 (d, 2H, Ar), 7.70 (d, 1H, NH)

Example 34: Synthesis of 3-(4-Isocyanato-phenyl)-2-(4-Isocyanato-benzoylamino)-propionic acid methyl ester

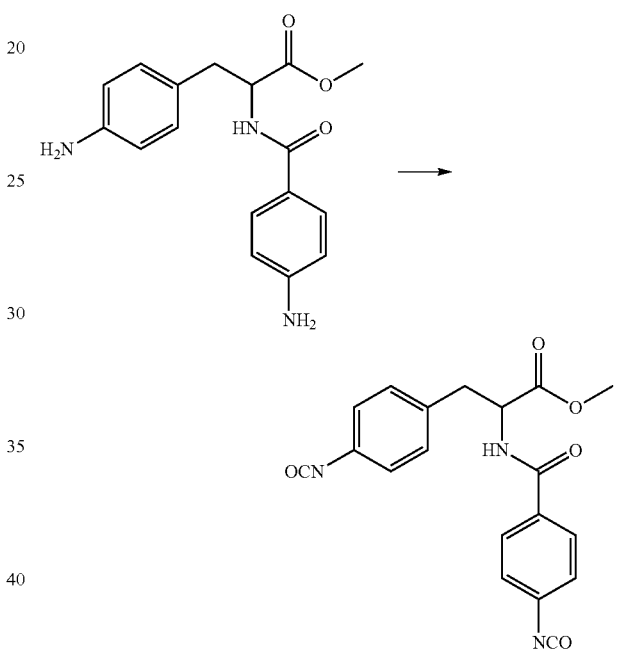

Into a solution of 2-Amino-3-(4-amino-phenyl)-propionic acid octadecyl ester (100 g) in dry 1,4-dioxane (2000 ml) under Nitrogen atmosphere maintained at 200° C. was added a solution of triphosgene (163 g) in 1,4-Dioxane (200 ml) in one lot. The reaction mixture was heated and refluxed for 3 hours. The condenser was then arranged for distillation and solvent removed by distillation at atmospheric pressure until the volume of the reaction mixture was reduced to approximately one third. Fresh dry dioxane (200 ml) was added and distilled off under vacuum. The residue was dissolved in Toluene (200 ml) and charcoal (5 g) was added. The solution was filtered hot and the solvent was distilled under vacuum to yield crude diisocyanate which was again dissolved in a mixture of toluene:hexane (6:4; 400 ml) by heating to 80° C. for 15 minutes. The solution was filtered and the solvent mixture was distilled off under vacuum. Hexane was added to the precipitate and pure diisocyanate was filtered, dried and packed in tight container to yield 65 g of pure 2-Isocyanato-3-(4-Isocyanato-phenyl)-propionic acid octadecyl ester as a white powder with a melting point of 78-80° C. The product was further characterized by IR: 2261 cm-1 and 1H NMR (CDCl3) δ 3.15-3.30 (m, 2H, CH$_2$), 3.70 (s, 3H, OCH3), 5.05 (m, 1H, CH), 6.60 (d, 1H, NH), 7.00 (d, 2H, Ar), 7.05 (d, 2H, Ar), 7.15 (d, 2H, Ar), 7.60 (d, 2H, Ar)

Example 35 Synthesis of 2-Benzyloxycarbonylamino-3-(4-nitro-phenyl)-propionic acid

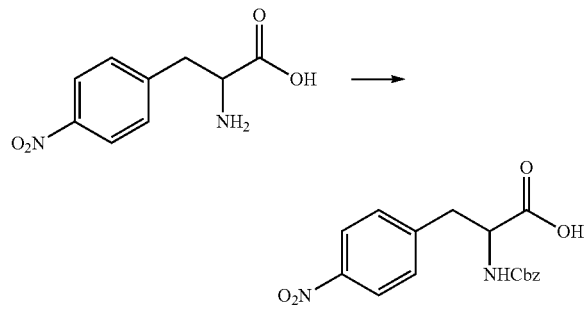

To a mixture of 4-nitro phenyl alanine (500 g), sodium hydroxide (162 g) and water (5000 ml) maintained at 0 to 5° C., was added drop wise 50% benzyl chloroformate in toluene (977 g). The reaction mixture was allowed to slowly come to room temperature and further stirred overnight. The reaction mixture was cooled to 10° C. and the pH was adjusted to 2 with dilute HCl. The residue precipitated was filtered and dried to yield pure 2-Benzyloxycarbonylamino-3-(4-nitro-phenyl)-propionic acid (600 g) as an off white powder with a melting point of 123-127° C. The product was characterized by 1H NMR (CDCl3+DMSOd6) δ 3-3.20 (m, 2H, CH2), 4.30 (m, 1H, CH), 4.90 (s, 2H, CH2), 7.20 (m, 6H, Ar & NH), 7.40 (d, 2H, Ar), 8.05 (d, 2H, Ar)

Example 36: Synthesis of 2-Benzyloxycarbonylamino-3-(4-nitro-phenyl)-propionic acid Stearyl ester

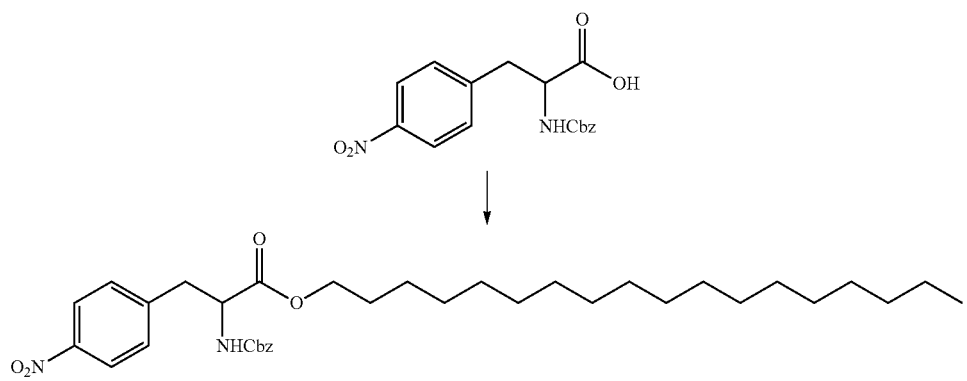

To a mixture of 2-benzyloxycarbonylamino-3-(4-nitro-phenyl)-propionic acid (400 g), potassium carbonate (192.5 g) in NMP (1460 ml) maintained at 200° C., was added dropwise 1-Bromo octadecane (425 g). The reaction mixture was allowed to slowly come to room temperature and further stirred for 24 hours. The reaction mixture was then poured onto ice water and the pH was adjusted to 7 with dilute HCl. The solid was filtered, dried and purified by column chromatography using hexane:ethyl acetate (95:5) as an eluant to yield pure 2-benzyloxycarbonylamino-3-(4-nitro-phenyl)-propionic acid stearyl ester (430 g) as a white powder with a melting point of 56-59° C. The product was further characterized by 1H NMR (CDCl3) δ 0.90 (t, 3H, CH3), 1.30 (m, 30H, 15 X CH2), 1.60 (m, 2H, CH2), 3.05-3.25 (m, 2H, CH2), 4.20 (m, 2H, CH2), 4.65 (m, 1H, CH), 5.15 (m, 2H, CH2), 5.40 (d, 1H, NH), 7.30 (m, 54H, Ar), 7.45 (d, 2H, Ar), 8.15 (d, 2H, Ar)

Example 37: Synthesis of 2-Amino-3-(4-amino-phenyl)-propionic acid octadecyl ester

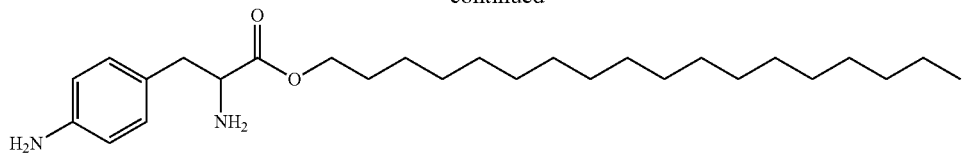

2-Benzyloxycarbonylamino-3-(4-nitro-phenyl)-propionic acid Stearyl Ester (430 g) was dissolved in ethyl acetate (2500 ml) in a pressure vessel. 10% Palladium carbon (58 g, 50% wet) was added and the reaction mixture was stirred under an atmosphere of Hydrogen (10 Kg) at 50° C. for 12 hours. The reaction mixture was brought to 200° C. and the catalyst was removed by filtration. The solvent was distilled off and the resulting diamine was precipitated by adding hexane. It was filtered and dried to yield pure 2-amino-3-(4-amino-phenyl)-propionic acid octadecyl ester (200 g) as a white powder with a melting point of 54-56° C. and a purity of 98% as determined by HPLC. The product was further characterized by 1H NMR (CDCl3) δ 0.90 (t, 3H, CH3), 1.25 (m, 30H, 15 X CH2), 1.65 (m, 2H, CH2), 2.90-3.05 (m, 2H, CH2), 3.70 (m, 1H, CH), 4.00-4.15 (m, 6H, 2 X NH2 & CH2), 6.60 (d, 2H, Ar), 6.95 (d, 2H, Ar)

Example 38: Synthesis of 2-Isocyanato-3-(4-isocyanato-phenyl)-propionic acid octadecyl ester

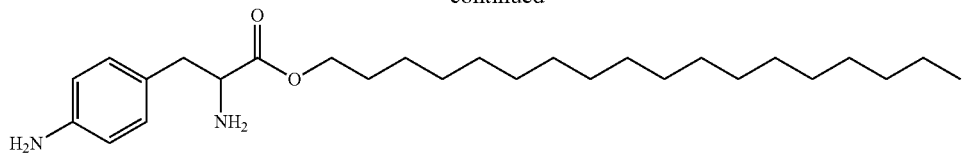

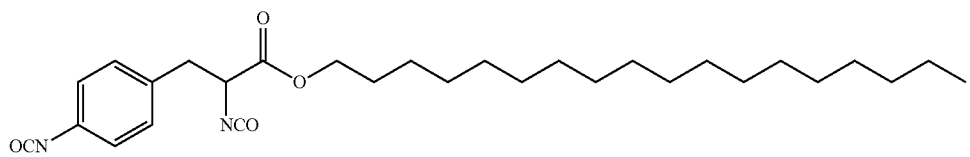

To a solution of 2-Amino-3-(4-amino-phenyl)-propionic acid octadecyl ester (100 g) in dry 1,4-dioxane (800 ml) maintained under nitrogen atmosphere at 10° C. was added a solution of triphosgene (116 g) in 1,4-dioxane (300 ml) in one lot. The reaction mixture was refluxed for 2 hours. The condenser was then arranged for distillation and solvent was removed by distillation at atmospheric pressure until the volume of the reaction mixture was reduced to approximately one third. Fresh dry Dioxane (300 ml) was added and the solvents were distilled off under vacuum. The residue was dissolved in toluene (300 ml) and then the toluene was distilled off. Fresh toluene (300 ml) was added along with charcoal (10 g) and the solution was filtered hot. The toluene was distilled off under vacuum to yield crude diisocyanate. This diisocyanate was kept in the freezer overnight. The disocyanate was purified via trituration and recrystallization using hexane (200 ml) to yield solid diisocyanate which was cooled to 0-5° C. and left for 30 minutes under nitrogen. The pure diisocyanate was filtered, dried and packed in tight container to yield 2-Isocyanato-3-(4-isocyanato-phenyl)-propionic acid octadecyl ester. The product was characterized by 1H NMR (CDCl3) δ 0.90 (t, 3H, CH3), 1.30 (m, 30H, 15 X CH2), 1.65 (m, 2H, CH2), 3.00-3.20 (m, 2H, CH2), 4.20 (m, 3H, CH & CH2), 7.05 (d, 2H, Ar), 7.15 (d, 2H, Ar)

Example 39: Synthesis of Polyurethane Polymer from 4-Nitrophenyl Alanine Stearyl Diisocyanate

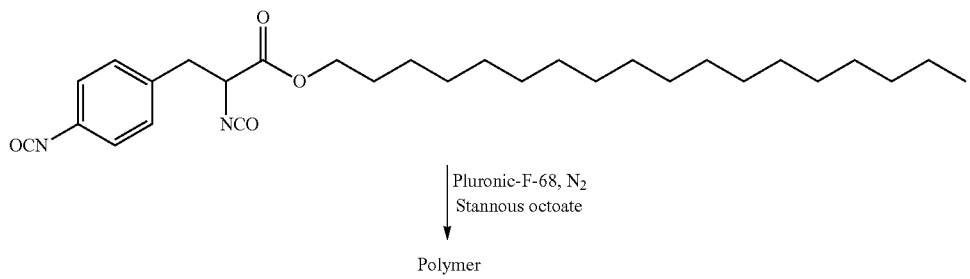

Into a clean flame dried 250 ml cylindrical flask equipped with nitrogen inlet and placed in an oil bath with mechanical stirrer was added pluronic-F-68 (86.8 g) under nitrogen. The temperature of the bath was increased upto 75-80° C. Once the Pluronic-F-68 melted, the temperature of the bath was lowered down to 60° C. Diisocyanate (10 g) was added to the pluronic while the bath temperature was maintained at 60° C. The reaction mixture was stirred at the same temperature for 2 hours followed by the addition of 1,4 Butanediol (1.9 g) and 0.5 ml 10% Stannous octoate catalyst solution in toluene. The reaction mixture became viscous syrup and was stirred at 60° C. for 2 hours. A second lot of a solution of 1,4-butanediol (0.4 g) in 1 ml dimethylacetamide and 10% stannous octoate catalyst in toluene 0.5 ml was added into the reaction mixture and left for stirring at the same temperature for 2 hours. The reaction mixture was then poured on to a petri dish and kept in a vacuum oven for 24 hours to yield 87 grams of off white color polyurethane polymer.

Example 40: Synthesis of Polyurethane Polymer from 4-Nitrophenyl Alanine Benzoic Acid Diisocyanate

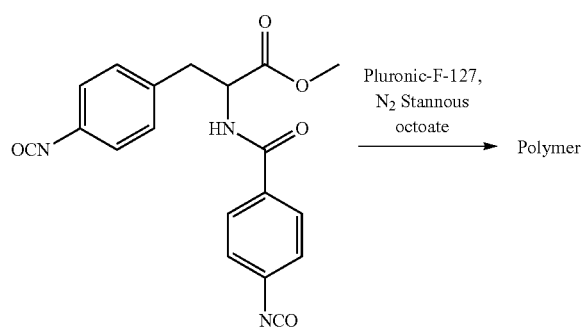

Into a clean flame dried 500 ml cylindrical flask equipped with nitrogen inlet and placed in an oil bath with mechanical stirrer was added pluronic-F-127 (172.6 g) under nitrogen. The temperature of the bath was increased upto 140-145° C. Once the Pluronic-F-127 melted, the temperature of the bath was lowered down to 60° C. Diisocyanate (5 g) was added to the pluronic while the bath temperature was maintained at 60° C. The reaction mixture was stirred at the same temperature for 2 hours followed by the addition of 1,4 Butanediol (1.9 g) and 0.5 ml 10% Stannous octoate catalyst solution in toluene. The reaction mixture became viscous syrup when stirred at 60° C. for 2 hours. The reaction mixture was then poured on to a petri dish and kept in a vacuum oven for 24 hours to yield 150 grams of pale yellow color polyurethane polymer.

When ranges are used herein for physical properties, such as molecular weight, or chemical properties, such as chemical formulae, all combinations and subcombinations of ranges and specific embodiments therein are intended to be included. All ranges recited herein include ranges therebetween, and can be inclusive or exclusive of the endpoints. Optional included ranges can be from integer values therebetween, at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like.

Numbered, Exemplary Embodiments

The invention includes the following embodiments E1 to E29:

E1. Absorbable Amines of the Formula A:

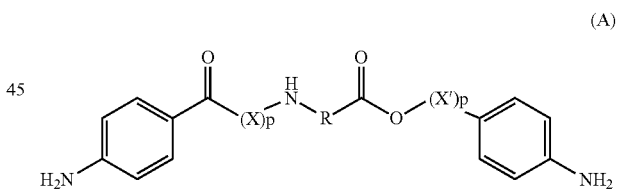

(A)

Wherein:
Each X is independently selected from:
—OCH$_2$CO— (glycolic ester moiety)
—OCH(CH$_3$)CO— (lactic ester moiety)
—OCH$_2$CH$_2$OCH$_2$CO— (dioxanone ester moiety)
—OCH$_2$CH$_2$CH$_2$CH$_2$CH$_2$CO— (caprolactone ester moiety);
—O(CH$_2$)$_y$CO— or, where y is one of the numbers 2, 3, 4, and 6-24 inclusive; or
—O(CH$_2$CH$_2$O)$_m$CH$_2$CO—; where m is integer between 2-24 inclusive; and,
And wherein p is indepently selected from 0 to 6 inclusive; and,
Each X' is independently selected from:
—CH$_2$COO— (glycolic moiety)
—CH(CH$_3$)COO— (lactic moiety)
—CH$_2$CH$_2$OCH$_2$COO— (dioxanone moiety)

—CH₂CH₂CH₂CH₂CH₂COO— (caprolactone moiety)

—(CH₂)$_y$COO— or, where y is one of the numbers 2, 3, 4, and 6-24 inclusive; or —(CH₂CH₂O)$_m$CH₂COO—; where m is integer between 2-24 inclusive; and, R is a residue of an amino acid including but not limited to alanine, asparagine, aspartic acid, gamma amino butyric acid, glycine, glutamic acid, valine, lysine, isoleucine, leucine, tyrosine, ornithine, phenylalanine and sarcosine, 3-aminotyrosine, 3-chlorotyrosine, 3,5-dibromotyrosine, 3,5-diiodotyrosine, homotyrosine, 3-iodotyrosine, 3-nitrotyrosine, 2-tyrosine, 3-tyrosine, 4-hydroxy-3-nitrophenylalanine, 5-hydroxytryptophan, 3-nitro-4-hydroxyphenylalanine, thyronine, 3,4-dihydroxyphenylalanine, 4-hydroxyphenylglycine, 3-aminosalicylic acid; 4-aminosalicylic acid; and 5-aminosalicylic acid.

E2. Absorbable Isocyanates of Formula B:

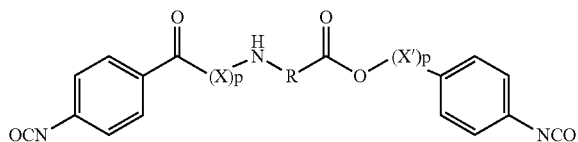

(B)

Wherein:

Each X is independently selected from:

—OCH₂CO— (glycolic ester moiety)

—OCH(CH₃)CO— (lactic ester moiety)

—OCH₂CH₂OCH₂CO— (dioxanone ester moiety)

—OCH₂CH₂CH₂CH₂CH₂CO— (caprolactone ester moiety);

—O(CH₂)$_y$CO— or, where y is one of the numbers 2, 3, 4, and 6-24 inclusive; or —O(CH₂CH₂O)$_m$CH₂CO—; where m is integer between 2-24 inclusive; and, And wherein p is indepently selected from 0 to 6 inclusive; and, Each X' is independently selected from:

—CH₂COO— (glycolic moiety)

—CH(CH₃)COO— (lactic moiety)

—CH₂CH₂OCH₂COO— (dioxanone moiety)

—CH₂CH₂CH₂CH₂CH₂COO— (caprolactone moiety)

—(CH₂)$_y$COO— or, where y is one of the numbers 2, 3, 4, and 6-24 inclusive; or —(CH₂CH₂O)$_m$CH₂COO—; where m is integer between 2-24 inclusive; and, R is a residue of an amino acid including but not limited to alanine, asparagine, aspartic acid, gamma amino butyric acid, glycine, glutamic acid, valine, lysine, isoleucine, leucine, tyrosine, ornithine, phenylalanine and sarcosine, 3-aminotyrosine, 3-chlorotyrosine, 3,5-dibromotyrosine, 3,5-diiodotyrosine, homotyrosine, 3-iodotyrosine, 3-nitrotyrosine, 2-tyrosine, 3-tyrosine, 4-hydroxy-3-nitrophenylalanine, 5-hydroxytryptophan, 3-nitro-4-hydroxyphenylalanine, thyronine, 3,4-dihydroxyphenylalanine, 4-hydroxyphenylglycine, 3-aminosalicylic acid; 4-aminosalicylic acid; and 5-aminosalicylic acid.

E3. Absorbable Amines of Formula C

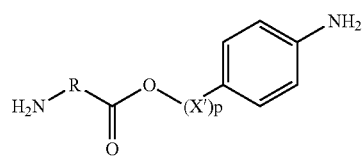

(C)

Wherein

Each X' is independently selected from:

—CH₂COO— (glycolic moiety)

—CH(CH₃)COO— (lactic moiety)

—CH₂CH₂OCH₂COO— (dioxanone moiety)

—CH₂CH₂CH₂CH₂CH₂COO— (caprolactone moiety)

—(CH₂)$_y$COO— or, where y is one of the numbers 2, 3, 4, and 6-24 inclusive; or —(CH₂CH₂O)$_m$CH₂COO—; where m is integer between 2-24 inclusive; and, And wherein p is indepently selected from 0 to 6 inclusive; and, R is a residue of an amino acid including but not limited to alanine, asparagine, aspartic acid, gamma amino butyric acid, glycine, glutamic acid, valine, lysine, isoleucine, leucine, tyrosine, ornithine, phenylalanine and sarcosine, 3-aminotyrosine, 3-chlorotyrosine, 3,5-dibromotyrosine, 3,5-diiodotyrosine, homotyrosine, 3-iodotyrosine, 3-nitrotyrosine, 2-tyrosine, 3-tyrosine, 4-hydroxy-3-nitrophenylalanine, 5-hydroxytryptophan, 3-nitro-4-hydroxyphenylalanine, thyronine, 3,4-dihydroxyphenylalanine, 4-hydroxyphenylglycine, 3-aminosalicylic acid; 4-aminosalicylic acid; and 5-aminosalicylic acid.

E4. Absorbable Isocyanates of Formula D

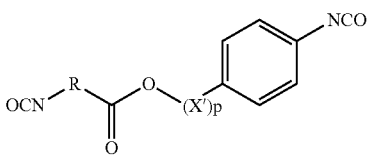

(D)

Wherein

Each X' is independently selected from

—CH₂COO— (glycolic moiety)

—CH(CH₃)COO— (lactic moiety)

—CH₂CH₂OCH₂COO— (dioxanone moiety)

—CH₂CH₂CH₂CH₂CH₂COO— (caprolactone moiety)

—(CH₂)$_y$COO— or, where y is one of the numbers 2, 3, 4, and 6-24 inclusive; or —(CH₂CH₂O)$_m$CH₂COO—; where m is integer between 2-24 inclusive; and, And wherein p is indepently selected from 0 to 6 inclusive; and, R is a residue of an amino acid including but not limited to alanine, asparagine, aspartic acid, gamma amino butyric acid, glycine, glutamic acid, valine, lysine, isoleucine, leucine, tyrosine, ornithine, phenylalanine and sarcosine, 3-aminotyrosine, 3-chlorotyrosine, 3,5-dibromotyrosine, 3,5-diiodotyrosine, homotyrosine, 3-iodotyrosine, 3-nitrotyrosine, 2-tyrosine, 3-tyrosine, 4-hydroxy-3-nitrophenylalanine, 5-hydroxytryptophan, 3-nitro-4-hydroxyphenylalanine, thyronine, 3,4-dihydroxyphenylalanine, 4-hydroxyphenylglycine, 3-aminosalicylic acid; 4-aminosalicylic acid; and 5-aminosalicylic acid.

E5. Absorbable Amines of Formula E

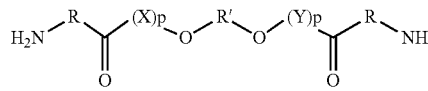

Wherein:
Each X is independently selected from:
—OCH$_2$CO— (glycolic ester moiety)
—OCH(CH$_3$)CO— (lactic ester moiety)
—OCH$_2$CH$_2$OCH$_2$CO— (dioxanone ester moiety)
—OCH$_2$CH$_2$CH$_2$CH$_2$CH$_2$CO— (caprolactone ester moiety);
—O(CH$_2$)$_y$CO— or, where y is one of the numbers 2, 3, 4, and 6-24 inclusive; or
—O(CH$_2$CH$_2$O)$_m$CH$_2$CO—; where m is integer between 2-24 inclusive; and,
And wherein p is indepently selected from 0 to 6 inclusive; and,
Each Y is independently selected from:
—COCH$_2$O— (glycolic moiety)
—COCH(CH$_3$)O— (lactic moiety)
—COCH$_2$OCH$_2$CH$_2$O— (dioxanone moiety)
—COCH$_2$CH$_2$CH$_2$CH$_2$CH$_2$O— (caprolactone moiety)
—CO(CH$_2$)$_y$O— or, where y is one of the numbers 2, 3, 4, and 6-24 inclusive; or
—CO(CH$_2$CH$_2$O)$_m$CH$_2$O—; where m is integer between 2-24 inclusive; and,
R is a residue of an amino acid including but not limited to alanine, asparagine, aspartic acid, gamma amino butyric acid, glycine, glutamic acid, valine, lysine, isoleucine, leucine, tyrosine, ornithine, phenylalanine and sarcosine, 3-aminotyrosine, 3-chlorotyrosine, 3,5-dibromotyrosine, 3,5-diiodotyrosine, homotyrosine, 3-iodotyrosine, 3-nitrotyrosine, 2-tyrosine, 3-tyrosine, 4-hydroxy-3-nitrophenylalanine, 5-hydroxytryptophan, 3-nitro-4-hydroxyphenylalanine, thyronine, 3,4-dihydroxyphenylalanine, 4-hydroxyphenylglycine, 3-aminosalicylic acid; 4-aminosalicylic acid; and 5-aminosalicylic acid, and
R' is a residue of a diol where in R' is alkyl or aryl, arylalkyl, with alkyl chains containing a primary (long) chain of 2 up to 24 chain atoms, or alkyl substituted with analogs in which primary chain —CH$_2$— groups may be substituted with —O—, or —S—, and wherein the primary chain and aryl can be substituted with lower alkyl group(s).

E6. Absorbable Isocyanates of Formula F

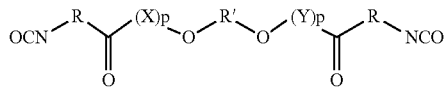

Wherein:
Each X is independently selected from:
—OCH$_2$CO— (glycolic ester moiety)
—OCH(CH$_3$)CO— (lactic ester moiety)
—OCH$_2$CH$_2$OCH$_2$CO— (dioxanone ester moiety)
—OCH$_2$CH$_2$CH$_2$CH$_2$CH$_2$CO— (caprolactone ester moiety);
—O(CH$_2$)$_y$CO— or, where y is one of the numbers 2, 3, 4, and 6-24 inclusive; or
—O(CH$_2$CH$_2$O)$_m$CH$_2$CO—; where m is integer between 2-24 inclusive; and,
And wherein p is indepently selected from 0 to 6 inclusive; and,
Each Y is independently selected from:
—COCH$_2$O— (glycolic moiety)
—COCH(CH$_3$)O— (lactic moiety)
—COCH$_2$OCH$_2$CH$_2$O— (dioxanone moiety)
—COCH$_2$CH$_2$CH$_2$CH$_2$CH$_2$O— (caprolactone moiety)
—CO(CH$_2$)$_y$O— or, where y is one of the numbers 2, 3, 4, and 6-24 inclusive; or
—CO(CH$_2$CH$_2$O)$_m$CH$_2$O—; where m is integer between 2-24 inclusive; and,
And wherein p is indepently selected from 0 to 6 inclusive; and,
R is a residue of an amino acid including but not limited to alanine, asparagine, aspartic acid, gamma amino butyric acid, glycine, glutamic acid, valine, lysine, isoleucine, leucine, tyrosine, ornithine, phenylalanine and sarcosine, 3-aminotyrosine, 3-chlorotyrosine, 3,5-dibromotyrosine, 3,5-diiodotyrosine, homotyrosine, 3-iodotyrosine, 3-nitrotyrosine, 2-tyrosine, 3-tyrosine, 4-hydroxy-3-nitrophenylalanine, 5-hydroxytryptophan, 3-nitro-4-hydroxyphenylalanine, thyronine, 3,4-dihydroxyphenylalanine, 4-hydroxyphenylglycine, 3-aminosalicylic acid; 4-aminosalicylic acid; and 5-aminosalicylic acid, and
R' is a residue of a diol where in R' is alkyl or aryl, arylalkyl, with alkyl chains containing a primary (long) chain of 2 up to 24 chain atoms, or alkyl substituted with analogs in which primary chain —CH$_2$— groups may be substituted with —O—, or —S—, and wherein the primary chain and aryl can be substituted with lower alkyl group(s)

E7. Absorbable Amines Derived from Nitrophenylalanine of the Formula G:

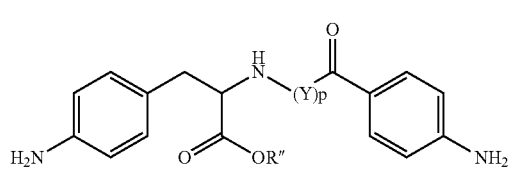

Wherein:
Each Y is independently selected from:
—COCH$_2$O— (glycolic moiety)
—COCH(CH$_3$)O— (lactic moiety)
—COCH$_2$OCH$_2$CH$_2$O— (dioxanone moiety)
—COCH$_2$CH$_2$CH$_2$CH$_2$CH$_2$O— (caprolactone moiety)
—CO(CH$_2$)$_y$O— or, where y is one of the numbers 2, 3, 4, and 6-24 inclusive; or
—CO(CH$_2$CH$_2$O)$_m$CH$_2$O—; where m is integer between 2-24 inclusive; and,
And wherein p is indepently selected from 0 to 6 inclusive; and,
R" is alkyl or aryl, arylalkyl, with alkyl chains containing a primary (long) chain up to 36 chain atoms (not including H), or alkyl substituted with analogs in which primary chain —CH$_2$— groups may be substituted with —O—, or —S— or ester groups, such as low mol.wt. polyesters or polyethers, and wherein the primary chain and aryl can be substituted with lower alkyl group(s), or R" is a biologically active substance.

E8. Absorbable Isocyanates Derived from Nitrophenylalanine of the Formula (H)

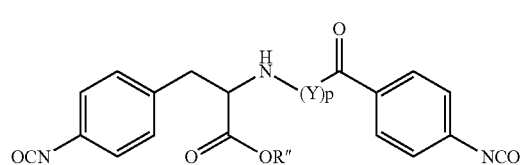

Wherein:
Each Y is independently selected from:
—COCH$_2$O— (glycolic moiety)
—COCH(CH$_3$)O— (lactic moiety)
—COCH$_2$OCH$_2$CH$_2$O— (dioxanone moiety)
—COCH$_2$CH$_2$CH$_2$CH$_2$CH$_2$O— (caprolactone moiety)
—CO(CH$_2$)$_y$O— or, where y is one of the numbers 2, 3, 4, and 6-24 inclusive; or
—CO(CH$_2$CH$_2$O)$_m$CH$_2$O—; where m is integer between 2-24 inclusive; and,
And wherein p is indepently selected from 0 to 6 inclusive; and,
R" is alkyl or aryl, arylalkyl, with alkyl chains containing a primary (long) chain up to 36 chain atoms (not including H), or alkyl substituted with analogs in which primary chain —CH$_2$— groups may be substituted with —O—, or —S— or ester groups, such as low mol.wt. polyesters or polyethers, and wherein the primary chain and aryl can be substituted with lower alkyl group(s), or R" is a biologically active substance.

E9. Absorbable Amines Derived from Nitrophenylalanine of the Formula I:

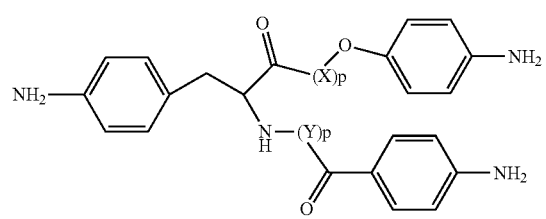

Wherein:
Each X is independently selected from:
—OCH$_2$CO— (glycolic ester moiety)
—OCH(CH$_3$)CO— (lactic ester moiety)
—OCH$_2$CH$_2$OCH$_2$CO— (dioxanone ester moiety)
—OCH$_2$CH$_2$CH$_2$CH$_2$CH$_2$CO— (caprolactone ester moiety);
—O(CH$_2$)$_y$CO— or, where y is one of the numbers 2, 3, 4, and 6-24 inclusive; or
—O(CH$_2$CH$_2$O)$_m$CH$_2$CO—; where m is integer between 2-24 inclusive; and,
And wherein p is indepently selected from 0 to 6 inclusive; and,
Each Y is independently selected from:
—COCH$_2$O— (glycolic moiety)
—COCH(CH$_3$)O— (lactic moiety)
—COCH$_2$OCH$_2$CH$_2$O— (dioxanone moiety)
—COCH$_2$CH$_2$CH$_2$CH$_2$CH$_2$O— (caprolactone moiety)
—CO(CH$_2$)$_y$O— or, where y is one of the numbers 2, 3, 4, and 6-24 inclusive; or
—CO(CH$_2$CH$_2$O)$_m$CH$_2$O—; where m is integer between 2-24 inclusive.

E10. Absorbable Isocyanates Derived from Nitrophenylalanine of the Formula J:

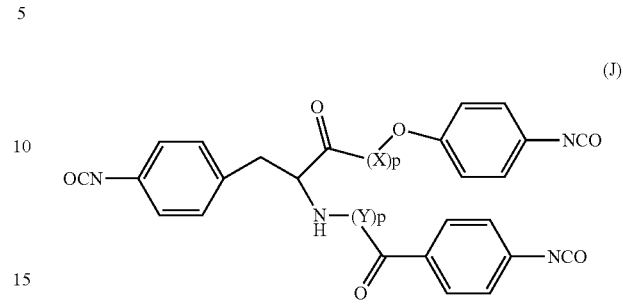

Wherein:
Each X is independently selected from:
—OCH$_2$CO— (glycolic ester moiety)
—OCH(CH$_3$)CO— (lactic ester moiety)
—OCH$_2$CH$_2$OCH$_2$CO— (dioxanone ester moiety)
—OCH$_2$CH$_2$CH$_2$CH$_2$CH$_2$CO— (caprolactone ester moiety);
—O(CH$_2$)$_y$CO— or, where y is one of the numbers 2, 3, 4, and 6-24 inclusive; or
—O(CH$_2$CH$_2$O)$_m$CH$_2$CO—; where m is integer between 2-24 inclusive; and,
And wherein p is indepently selected from 0 to 6 inclusive; and,
Each Y is independently selected from:
—COCH$_2$O— (glycolic moiety)
—COCH(CH$_3$)O— (lactic moiety)
—COCH$_2$OCH$_2$CH$_2$O— (dioxanone moiety)
—COCH$_2$CH$_2$CH$_2$CH$_2$CH$_2$O— (caprolactone moiety)
—CO(CH$_2$)$_y$O— or, where y is one of the numbers 2, 3, 4, and 6-24 inclusive; or
—CO(CH$_2$CH$_2$O)$_m$CH$_2$O—; where m is integer between 2-24 inclusive.

E11. A Monomer or Macromer of Formula (K):

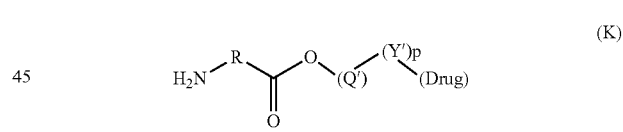

Where in
Each Y' is independently selected from
—OCOCH$_2$— (glycolic moiety)
—OCOCH (CH$_3$)— (lactic moiety)
—OCOCH$_2$OCH$_2$CH$_2$— (dioxanone moiety)
—OCOCH$_2$CH$_2$CH$_2$CH$_2$CH$_2$— (caprolactone moiety)
—OCO(CH$_2$)$_y$— or, where y is one of the numbers 2, 3, 4, and 6-24 inclusive; or
—OCO(CH$_2$CH$_2$O)$_m$CH$_2$—; where m is integer between 2-24 inclusive; and,
And wherein p is indepently selected from 0 to 6 inclusive; and,
And Q' is the residue of a diol
Drug=Any biologically active substance containing
—OH functional group
—COOH functional group
—NH$_2$ functional group
R is a residue of an amino acid including but not limited to alanine, asparagine, aspartic acid, gamma amino butyric acid, glycine, glutamic acid, valine, lysine, isoleucine, leucine, tyrosine, ornithine, phenylalanine and sarcosine, 3-aminotyrosine, 3-chlorotyrosine, 3,5-dibromotyrosine, 3,5-diiodotyrosine, homotyrosine, 3-iodotyrosine, 3-nitrotyrosine, 2-tyrosine, 3-tyrosine, 4-hydroxy-3-nitrophenylalanine, 5-hydroxytryptophan, 3-nitro-4-hydroxyphenylalanine, thyronine, 3,4-dihydroxyphenylalanine, 4-hydroxyphenylglycine, 3-aminosalicylic acid; 4-aminosalicylic acid; and 5-aminosalicylic acid.

E12. Drug and Nitric Oxide Releasing Amino Acid Monomers of Formula L:

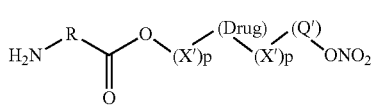

(L)

Where in
Each X' is independently selected from
—CH$_2$COO— (glycolic moiety)
—CH(CH$_3$)COO— (lactic moiety)
—CH$_2$CH$_2$OCH$_2$COO— (dioxanone moiety)
—CH$_2$CH$_2$CH$_2$CH$_2$CH$_2$COO— (caprolactone moiety)
—(CH$_2$)$_y$COO— or, where y is one of the numbers 2, 3, 4, and 6-24 inclusive; or
—(CH$_2$CH$_2$O)$_m$CH$_2$COO—; where m is integer between 2-24 inclusive; and,
And wherein p is indepently selected from 0 to 6 inclusive; and,
And Q' is the residue of diol and
Wherein
Drug=Any bioactive substance containing
—OH functional group
—COOH functional group
—NH2 functional group
R is a residue of an amino acid including but not limited to alanine, asparagine, aspartic acid, gamma amino butyric acid, glycine, glutamic acid, valine, lysine, isoleucine, leucine, tyrosine, ornithine, phenylalanine and sarcosine, 3-aminotyrosine, 3-chlorotyrosine, 3,5-dibromotyrosine, 3,5-diiodotyrosine, homotyrosine, 3-iodotyrosine, 3-nitrotyrosine, 2-tyrosine, 3-tyrosine, 4-hydroxy-3-nitrophenylalanine, 5-hydroxytryptophan, 3-nitro-4-hydroxyphenylalanine, thyronine, 3,4-dihydroxyphenylalanine, 4-hydroxyphenylglycine, 3-aminosalicylic acid; 4-aminosalicylic acid; and 5-aminosalicylic acid.

E13. Absorbable Amide Diacids Derived from Amino Acids and Symmetrical and Unsymmetrical Ether Acid of the Formula M:

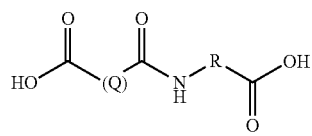

(M)

Wherein:
Q is residue of symmetrical and/or unsymmetrical ether acids
R is a residue of amino acid including but not limited to Alanine, Asparagine, Aspartic acid, gamma amino butyric acid, glycine, glutamic acid, valine, lysine, isoleucine, leucine, tyrosine, ornithine, phenylalanine and sarcosine.

E14. Diisocyanate Derived from Nitrophenyl Alanine of the Formula N Respectively

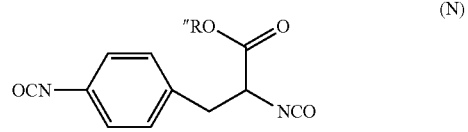

(N)

Wherein
R" is alkyl or aryl, arylalkyl, with alkyl chains containing a primary (long) chain up to 36 chain atoms (not including H), or alkyl substituted with analogs in which primary chain —CH$_2$— groups may be substituted with —O—, or —S— or ester groups, such as low mol.wt. polyesters or polyethers, and wherein the primary chain and aryl can be substituted with lower alkyl group(s), or R" is a biologically active substance.

Diisocyanate the formula N including but not limited to the following:

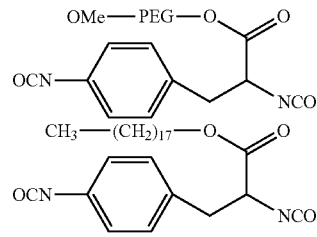

E15. Absorbable Amines Derived from 3-Nitrotyrosine of the Formula P:

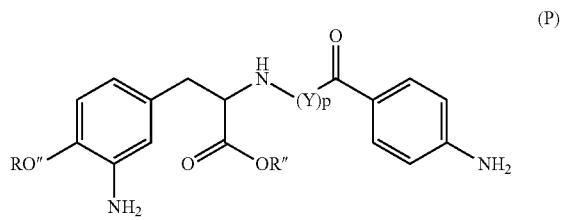

(P)

Wherein:
Each Y is independently:
—COCH$_2$O— (glycolic ester moiety)
—COCH (CH$_3$)O— (lactic ester moiety)
—COCH$_2$OCH$_2$CH$_2$O— (dioxanone ester moiety)
—COCH$_2$CH$_2$CH$_2$CH$_2$CH$_2$O— (caprolactone ester moiety)
—OCO(CH$_2$)$_y$— or, where y is one of the numbers 2, 3, 4, and 6-24 inclusive; or
—OCO(CH$_2$CH$_2$O)$_m$CH$_2$—; where m is integer between 2-24 inclusive;
And wherein p is indepently selected from 0 to 6 inclusive; and,
R" is alkyl or aryl, arylalkyl, with alkyl chains containing a primary (long) chain up to 36 chain atoms (not including H), or alkyl substituted with analogs in which primary chain —CH$_2$— groups may be substituted with —O—, or —S— or ester groups, such as low mol.wt. polyesters or polyethers, and wherein the primary chain and aryl can be substituted with lower alkyl group(s), or R" is a biologically active substance.

E16. Absorbable Isocyanates Derived from 3-Nitrotyrosine of the Formula (S)

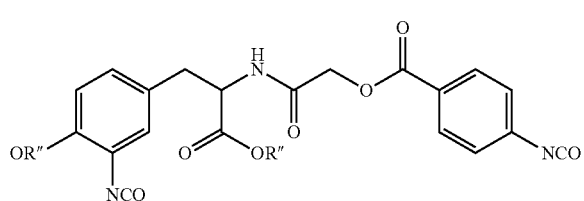

Wherein:
Each Y is independently:
—COCH$_2$O— (glycolic ester moiety)
—COCH(CH$_3$)O— (lactic ester moiety)
—COCH$_2$OCH$_2$CH$_2$O— (dioxanone ester moiety)
—COCH$_2$CH$_2$CH$_2$CH$_2$CH$_2$O— (caprolactone ester moiety)
—OCO(CH$_2$)$_y$— or, where y is one of the numbers 2, 3, 4, and 6-24 inclusive; or
—OCO(CH$_2$CH$_2$O)$_m$CH$_2$—; where m is integer between 2-24 inclusive;
And wherein p is indepently selected from 0 to 6 inclusive; and,
R" is alkyl or aryl, arylalkyl, with alkyl chains containing a primary (long) chain up to 36 chain atoms (not including H), or alkyl substituted with analogs in which primary chain —CH$_2$— groups may be substituted with —O—, or —S— or ester groups, such as low mol.wt. polyesters or polyethers, and wherein the primary chain and aryl can be substituted with lower alkyl group(s), or R" is a biologically active substance.

E17. Absorbable Amines Derived from 3-Nitrotyrosine of the Formula (T):

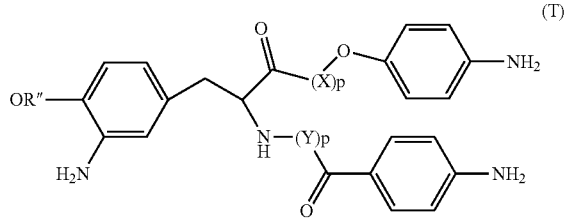

Wherein:
Each X is independently:
—OCH$_2$CO— (glycolic ester moiety)
—OCH(CH$_3$)CO— (lactic ester moiety)
—OCH$_2$CH$_2$OCH$_2$CO— (dioxanone ester moiety)
—OCH$_2$CH$_2$CH$_2$CH$_2$CH$_2$CO— (caprolactone ester moiety)
—(CH$_2$)$_y$COO— or, where y is one of the numbers 2, 3, 4, and 6-24 inclusive; or
—(CH$_2$CH$_2$O)$_m$CH$_2$COO—; where m is integer between 2-24 inclusive; and,
And wherein p is indepently selected from 0 to 6 inclusive; and, Y is independently selected from
—COCH$_2$O— (glycolic moiety)
—COCH(CH$_3$)O— (lactic moiety)
—COCH$_2$OCH$_2$CH$_2$O— (dioxanone moiety)
—COCH$_2$CH$_2$CH$_2$CH$_2$CH$_2$O— (caprolactone moiety)
—OCO(CH$_2$)$_y$— or, where y is one of the numbers 2, 3, 4, and 6-24 inclusive; or
—OCO(CH$_2$CH$_2$O)$_m$CH$_2$—; where m is integer between 2-24 inclusive;
And wherein p is indepently selected from 0 to 6 inclusive; and,
R" is alkyl or aryl, arylalkyl, with alkyl chains containing a primary (long) chain up to 36 chain atoms (not including H), or alkyl substituted with analogs in which primary chain —CH$_2$— groups may be substituted with —O—, or —S— or ester groups, such as low mol.wt. polyesters or polyethers, and wherein the primary chain and aryl can be substituted with lower alkyl group(s), or R" is a biologically active substance.

E18. Absorbable Isocyanates Derived from 3-NItrotyrosine of the Formula (U):

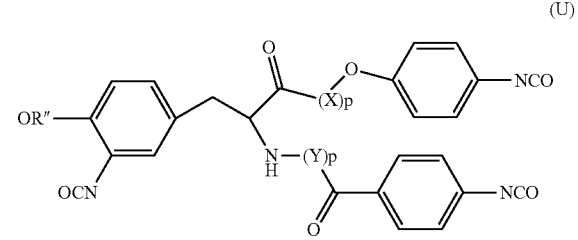

Wherein:
Each X is independently:
—OCH$_2$CO— (glycolic ester moiety)
—OCH(CH$_3$)CO— (lactic ester moiety)
—OCH$_2$CH$_2$OCH$_2$CO— (dioxanone ester moiety)
—OCH$_2$CH$_2$CH$_2$CH$_2$CH$_2$CO— (caprolactone ester moiety)
—(CH$_2$)$_y$COO— or, where y is one of the numbers 2, 3, 4, and 6-24 inclusive; or
—(CH$_2$CH$_2$O)$_m$CH$_2$COO—; where m is integer between 2-24 inclusive; and,
And wherein p is indepently selected from 0 to 6 inclusive; and, Y is independently selected from
—COCH$_2$O— (glycolic moiety)
—COCH(CH$_3$)O— (lactic moiety)
—COCH$_2$OCH$_2$CH$_2$O— (dioxanone moiety)
—COCH$_2$CH$_2$CH$_2$CH$_2$CH$_2$O— (caprolactone moiety)
—OCO(CH$_2$)$_y$— or, where y is one of the numbers 2, 3, 4, and 6-24 inclusive; or
—OCO(CH$_2$CH$_2$O)$_m$CH$_2$—; where m is integer between 2-24 inclusive; And wherein p is indepently selected from 0 to 6 inclusive; and,
R" is alkyl or aryl, arylalkyl, with alkyl chains containing a primary (long) chain up to 36 chain atoms (not including H), or alkyl substituted with analogs in which primary chain —CH$_2$— groups may be substituted with —O—, or —S— or ester groups, such as low mol.wt. polyesters or polyethers, and wherein the primary chain and aryl can be substituted with lower alkyl group(s), or R" is a biologically active substance.

E19. A Diisocyanate Derived from 3-Nitrotyrosine of the Formula V:

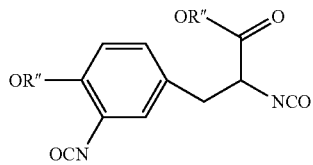

Wherein
R" is alkyl or aryl, arylalkyl, with alkyl chains containing a primary (long) chain up to 36 chain atoms (not including H), or alkyl substituted with analogs in which primary chain —$CH_2$— groups may be substituted with —O—, or —S— or ester groups, such as low mol.wt. polyesters or polyethers, and wherein the primary chain and aryl can be substituted with lower alkyl group(s), or R" is a biologically active substance.

E20. Hydrolysable Amide Diacids Derived from Diamines and Symmentrical and Unsymmentrical Ether Acids of the Following Formula W:

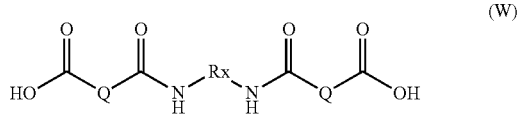

Where in Q is a residue of symmetrical and/or unsymmetrical ether acids.
Rx is the residue of a diamine where in Rx is alkyl, aryl, arylalkyl and alkyl groups containing oxygen or sulfur.

E21. An Amine or Isocyanate Derived from Nitrophenylalanine of the Formula Z or ZZ:

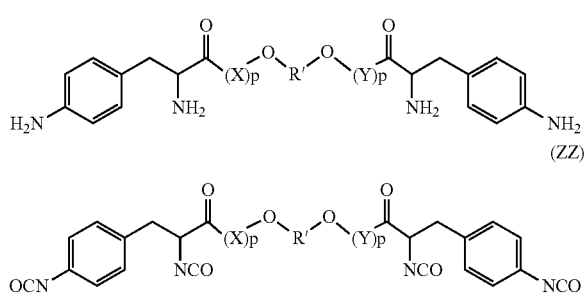

Wherein:
Each Y is independently selected from:
—$COCH_2O$— (glycolic moiety)
—$COCH(CH_3)O$— (lactic moiety)
—$COCH_2OCH_2CH_2O$— (dioxanone moiety)
—$COCH_2CH_2CH_2CH_2CH_2O$— (caprolactone moiety)
—$CO(CH_2)_yO$— or, where y is one of the numbers 2, 3, 4, and 6-24 inclusive; or
—$CO(CH_2CH_2O)_mCH_2O$—; where m is integer between 2-24 inclusive;
p is independently selected from 0 to 6 inclusive;
Each X is independently:
—$OCH_2CO$— (glycolic ester moiety)
—$OCH(CH_3)CO$— (lactic ester moiety)
—$OCH_2CH_2OCH_2CO$— (dioxanone ester moiety)
—$OCH_2CH_2CH_2CH_2CH_2CO$— (caprolactone ester moiety)
—$(CH_2)_yCOO$— or, where y is one of the numbers 2, 3, 4, and 6-24 inclusive; or
—$(CH_2CH_2O)_mCH_2COO$—; where m is integer between 2-24 inclusive; and
R' is a residue of a diol where in R' is alkyl, aryl or arylalkyl.

E22. A surgical article or component thereof or polymeric carrier comprising a polymer that comprises an amine, isocyanate or monomer according to one of the foregoing embodiments, which is a stent, stent coating, wound covering, burn covering, foam, highly porous foams, reticulated foams, tissue engineering scaffold, film, adhesion prevention barrier, implantable medical device, controlled drug delivery system, suture, ligature, needle and suture combination, surgical clip, surgical staple, surgical prosthesis, textile structure, coupling, tube, support, screw, pin, bone wax formulation or an adhesion prevention barrier.

E23. A surgical article or component thereof according to embodiment E22, wherein a biologically active agent is physically embedded or dispersed into the polymer matrix of the controlled delivery system.

E24. A surgical article or component thereof or polymeric carrier of embodiment E22, wherein the polymer is an absorbable polyester that is polymerized with a lactone monomer including but not limited to glycolide, lactide, ε-caprolactone, trimethylene carbonate, δ-valerolactone, β-butyrolactone, morpholinedione, pivalolactone, ε-decalactone, 2,5-diketomorpholine, and p-dioxanone and combinations thereof.

E25. A pharmaceutical composition comprising a polymeric carrier of embodiment E22 and a drug uniformly dispersed therein.

E26. A surgical article or component thereof or polymeric carrier, comprising a polymer formed by reacting an amine of one of embodiments E1, E3, E5, E7, E9, E11, E12, E15, E17 or E21 with an isocyanate, carboxylic acid, activated carboxylic acid, or epoxide.

E27. A surgical article or component thereof or polymeric carrier, comprising a polymer formed by reacting an isocyanate of one of embodiments E2, E4, E6, E8, E10, E14, E16, E18, E19 or E21 with an amine, alcohol, aminoalcohol, thiol or combination thereof.

E28. A surgical article or component thereof or polymeric carrier, comprising a polymer formed by reacting a carboxylic acid of one of embodiments E13 or E20 with an alcohol, amine or combination thereof.

In another embodiment, in the synthesis of isocyanates described in this patent application, the 4-nitrophenol (ortho, meta, para) can be replaced by 4-$NO_2$-phenyl-$CH_2OH$ and/or 4-$NO_2$-phenyl-$CH_2CH_2OH$. Similarly, the 4-nitrobenzoic acid (ortho, meta, para) can be replaced by 4-$NO_2$-phenyl-$CH_2CO_2H$ and/or 4-$NO_2$-phenyl-$CH_2CH_2CO_2H$. Alternatively, the 4-nitrophenol can be replaced or substituted with 4-$NO_2$-(aromatic ring)-P—OH and 4-$NO_2$-(aromatic ring)-P—OH. Similarly, the 4-nitrobenzoic acid can be replaced or substituted with 4-$NO_2$-(aromatic ring)-P—$CO_2H$ and 4-$NO_2$-(aromatic ring)-P—$CO_2H$ wherein the aromatic rings can be monocyclic, bicyclic or polycyclic. The aromatic rings can also be fused. The aromatic rings can also be heterocyclic containing non-carbon ring atoms such as oxygen, nitrogen and sulfur. P is selected from an alkylene, alkylene-arylene, and an alicyclic chain. Further, the present invention also provides hydrolysable diisocyanates derived from these molecules further functionalized with one or more groups selected from glycolic acid, lactic acid, caprolactone, and a p-dioxanone moiety. The positions of nitro to hydroxyl or carboxyl can be ortho meta or para on the aromatic ring. The present invention also provides asborbable polyurethanes derived from the above diisocyanates.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. An absorbable compound of formula F:

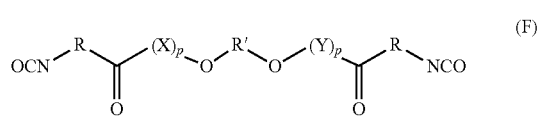
(F)

wherein:
each X is independently selected from:
—OCH$_2$C(O)—;
—OCH(CH$_3$)C(O)—;
—OCH$_2$CH$_2$OCH$_2$C(O)—;
—OCH$_2$CH$_2$CH$_2$CH$_2$CH$_2$C(O)—;
—O(CH$_2$)$_y$C(O)—; and,
—O(CH$_2$CH$_2$O)$_m$CH$_2$C(O)—;
each Y is independently selected from:
—C(O)CH$_2$O—;
—C(O)CH(CH$_3$)O;
—C(O)CH$_2$OCH$_2$CH2O—;
—C(O)CH$_2$CH$_2$CH$_2$CH$_2$CH$_2$O;
—C(O)(CH$_2$)$_y$O—; and,
—C(O)(CH$_2$CH$_2$O)$_m$CH$_2$O—;
m is integer between 2-24 inclusive;
p is independently selected from 1 and 2;
y is one of the numbers 2, 3, 4, and 6-24;
wherein the OCN—R—C(O)O and OC(O)—R—NCO moieties of Formula F (O being from an X or Y group) are an amino acid selected from: alanine, asparagine, aspartic acid, gamma amino butyric acid, glycine, glutamic acid, valine, lysine, isoleucine, leucine, and ornithine; and,
R' is selected from alkyl, aryl and arylalkyl, wherein the alkyl moiety, when present, comprises a primary chain of 2-24 carbon atoms;
optionally, in R', one or more CH$_2$ groups in the primary chain are replaced with O or S; and,
optionally, in R', the primary chain or aryl is independently substituted with lower alkyl group(s).

2. The absorbable compound of claim 1, wherein:
p is 1; and
the OCN—R—C(O)O and OC(O)—R—NCO moieties of Formula F (O being from an X or Y group) are an amino acid selected from:
alanine, asparagine, aspartic acid, gamma amino butyric acid, glycine, glutamic acid, valine, lysine, isoleucine, leucine, and ornithine.

3. The absorbable compound of claim 1, wherein the compound is selected from:

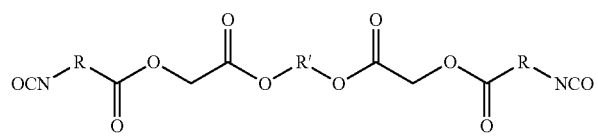
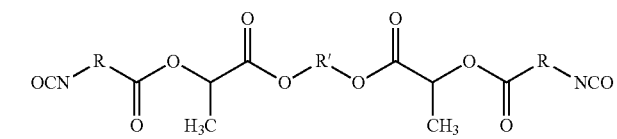

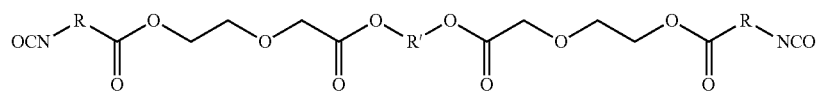

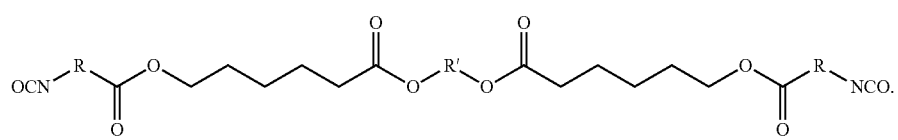

4. The absorbable compound of claim 1, wherein the compound is selected from:

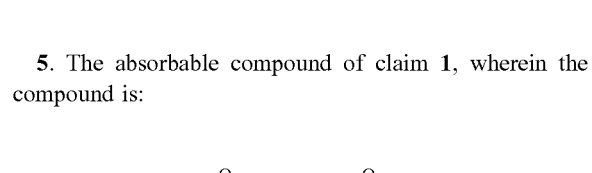

5. The absorbable compound of claim 1, wherein the compound is:

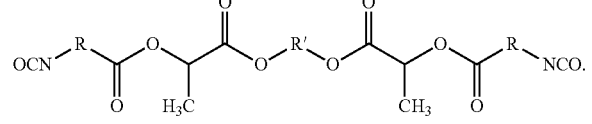

6. The absorbable compound of claim 1, wherein the compound is:

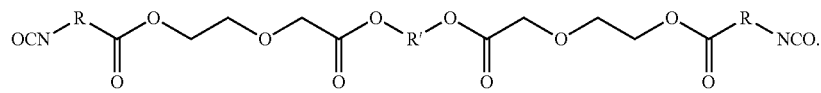

7. The absorbable compound of claim 1, wherein the compound is:

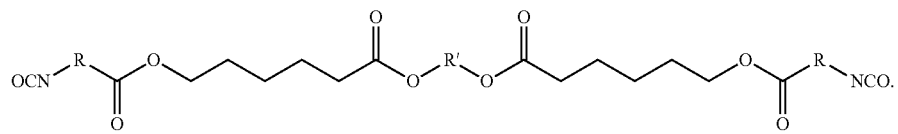

8. A surgical article or component thereof or polymeric carrier, comprising:
a polymer made from the isocyanate of claim 1,
wherein the article or component thereof or polymeric carrier is selected from: a stent, stent coating, wound covering, burn covering, foam, highly porous foams, reticulated foams, tissue engineering scaffold, film, adhesion prevention barrier, implantable medical device, controlled drug delivery system, suture, ligature, needle and suture combination, surgical clip, surgical staple, surgical prosthesis, textile structure, coupling, tube, support, screw, pin, bone wax formulation, tissue adhesive, and an adhesion prevention barrier.

9. A surgical article or component thereof of claim 8, wherein a biologically active agent is physically embedded or dispersed into the polymer matrix of the controlled delivery system.

10. A pharmaceutical composition comprising a polymeric carrier of claim 8 and a drug uniformly dispersed therein.

11. A polymer containing surgical article or component thereof or polymeric carrier selected from: a stent, stent coating, wound covering, burn covering, foam, highly porous foam, reticulated foam, tissue engineering scaffold, film, adhesion prevention barrier, implantable medical device, controlled drug delivery system, suture, ligature, needle and suture combination, surgical clip, surgical staple, surgical prosthesis, textile structure, coupling, tube, support, screw, pin, bone wax formulation, and an adhesion prevention barrier,
wherein the polymer is an absorbable polyurethane made from the isocyanate of claim 1 that is further polymerized with a lactone monomer selected from: glycolide, lactide, caprolactone, p-dioxanone, TMC, δ-valerolactone, β-butyrolactone, morpholinedione, pivalolactone, ε-decalactone, 2,5-diketomorpholine, and combinations thereof.

12. A surgical article or component thereof or polymeric carrier, comprising:
a polymer formed by reacting an isocyanate of one of claim 1 with a monomer selected from: an amine, an alcohol, an aminoalcohol, a thiol, and combination thereof.

* * * * *